(12) United States Patent
Montana et al.

(10) Patent No.: US 8,394,830 B2
(45) Date of Patent: Mar. 12, 2013

(54) QUINOLINES AND THEIR THERAPEUTIC USE

(75) Inventors: John Gary Montana, Essex (GB); Harry Finch, Essex (GB); George Hynd, Essex (GB); Michael Colin Cramp, Essex (GB); Rosa Arienzo, Essex (GB); Neville McLean, Essex (GB)

(73) Assignee: Pulmagen Therapeutics (Asthma) Limited, Slough (GB)

( * ) Notice: Subject to any disclaimer, the term of this patent is extended or adjusted under 35 U.S.C. 154(b) by 0 days.

(21) Appl. No.: 13/435,242

(22) Filed: Mar. 30, 2012

(65) Prior Publication Data

US 2012/0184579 A1    Jul. 19, 2012

Related U.S. Application Data

(63) Continuation of application No. 12/531,935, filed as application No. PCT/GB2008/001201 on Apr. 3, 2008, now Pat. No. 8,173,812.

(30) Foreign Application Priority Data

Apr. 4, 2007 (GB) .................................. 0706636.8
Dec. 14, 2007 (GB) .................................. 0724430.4

(51) Int. Cl.
    *A61K 31/04* (2006.01)
(52) U.S. Cl. ....................................... 514/312; 514/313
(58) Field of Classification Search .................. 546/153, 546/159; 514/312, 313
See application file for complete search history.

(56) References Cited

U.S. PATENT DOCUMENTS 7,858,640 B2 * 12/2010 Cramp et al. .................. 514/311
8,173,812 B2 * 5/2012 Montana et al. ............... 546/153

FOREIGN PATENT DOCUMENTS

WO    WO 2005/018529    3/2005

OTHER PUBLICATIONS

Mandhane, Internationl Immunopharmacology, 11, 1646-1662, 2011.*
Burgess, Chapter 8, pp. 119-134, Annual Reports in MEdicinal Chemistry, vol. 46, 2011.*

* cited by examiner

*Primary Examiner* — D M Seaman
(74) *Attorney, Agent, or Firm* — Saliwanchik, Lloyd & Eisenschenk

(57) ABSTRACT

Compounds of formula (I) are CRTH2 ligands, useful in the treatment of, for example, asthma and COPD wherein: $R^1$ is halogen or cyano; $R^2$ is hydrogen or methyl; $R^3$ and $R^4$ are independently —$OR^6$, $C_1$-$C_6$alkyl or $C_3$-$C_6$cycloalkyl, the latter two groups being optionally substituted by one or more halogen atoms; $R^5$ is hydrogen or halogen; $R^6$ is $C^1C^6$alkyl or $C^3$-$C^6$cycloalkyl, either of which being optionally substituted by one or more halogen atoms; X is —$CH_2$—, —S—, or —O—; one of Y and $Y^1$ is hydrogen and the other is $OR^6$, —C(=O)$R^7$, $NR^8SO_2R^6$ or a heterocyclic group selected from those referred to in the specification; and $R^6$, $R^7$ and $R^8$ are as defined in the specification.

3 Claims, No Drawings

QUINOLINES AND THEIR THERAPEUTIC USE

CROSS-REFERENCE TO A RELATED APPLICATION

This application is a continuation application of U.S. Ser. No. 12/531,935, filed Jan. 27, 2010 now U.S. Pat. No. 8,173,812 as a National Stage Application of International Application Number PCT/GB2008/001201, filed Apr. 3, 2008; which claims priority to Great Britain Application No. 0706636.8, filed Apr. 4, 2007 and Great Britain Application No. 0724430.4, filed Dec. 14, 2007, all of which are incorporated herein by reference in their entirety.

FIELD OF THE INVENTION

This invention relates to a class of quinoline compounds which are ligands of the CRTH2 receptor (Chemoattractant Receptor-homologous molecule expressed on T Helper cells type 2), and their use in the treatment of diseases responsive to modulation of CRTH2 receptor activity, principally diseases having a significant inflammatory component. The invention also relates to novel members of that class of ligands and pharmaceutical compositions containing them.

BACKGROUND TO THE INVENTION

Mast cells are known to play an important role in allergic and immune responses through the release of a number of mediators, such as histamine, leukotrienes, cytokines, prostaglandin $D_2$, etc (Boyce; Allergy Asthma Proc., 2004, 25, 27-30). Prostaglandin $D_2$ ($PGD_2$) is the major metabolite produced by the action of cyclooxygenase on arachadonic acid by mast cells in response to allergen challenge (Lewis et al; J. Immunol., 1982, 129; 1627-1631). It has been shown that $PGD_2$ production is increased in patients with systemic mastocytosis (Roberts; N. Engl. J. Med., 1980, 303, 1400-1404), allergic rhinitis (Naclerio et al; Am. Rev. Respir. Dis., 1983, 128, 597-602; Brown et al; Arch. Otolarynol. Head Neck Surg., 1987, 113, 179-183; Lebel et al; J. Allergy Clin. Immunol., 1988, 82, 869-877), bronchial asthma (Murray et al; N. Engl. J. Med., 1986, 315, 800-804; Liu et al; Am. Rev. Respir. Dis., 1990, 142, 126-132; Wenzel et al; J. Allergy Clin. Immunol., 1991, 87, 540-548), and urticaria (Heavey et al; J. Allergy Clin. Immunol., 1986, 78, 458-461). $PGD_2$ mediates it effects through two receptors, the $PGD_2$ (or DP) receptor (Bole et al; J. Biol. Chem., 1995, 270, 18910-18916) and the chemoattractant receptor-homologous molecule expressed on Th2 (or CRTH2) (Negate et al; J. Immunol., 1999, 162, 1278-1289; Powell; Prostaglandins Luekot. Essent. Fatty Acids, 2003, 69, 179-185). Therefore, it has been postulated that agents that antagonise the effects of $PGD_2$ at its receptors may have beneficial effects in number of disease states.

The CRTH2 receptor has been shown to be expressed on cell types associated with allergic inflammation, such as basophils, eosinophils, and Th2-type immune helper cells (Hirai et al; J. Exp. Med., 2001, 193, 265-261). The CRTH2 receptor has been shown to mediate $PGD_2$-mediated cell migration in these cell types (Hirai et al; J. Exp. Med., 2001, 193, 255-261), and also to play a major role in neutrophil and eosinophil cell recruitment in a model of contact dermatitis (Takeshita et al; Int. Immunol., 2004, 16, 947-959). Ramatroban {(3R)-3-[(4-fluorophenyl)sulphonyl-amino]-1,2,3,4-tetrahydro-9H-carbazole-9-propanoic acid}, a dual CRTH2 and thromboxane $A_2$ receptor antagonist, has been shown to attenuate these responses (Sugimoto et al; J. Pharmacol. Exp. Ther., 2003, 305, 347-352; Takeshita et al; op. cit.). The potential of $PGD_2$ both to enhance allergic inflammation and induce an inflammatory response has been demonstrated in mice and rats. Transgenic mice over expressing $PGD_2$ synthase exhibit an enhanced pulmonary eosinophilia and increased levels of Th2 cytokines in response to allergen challenge (Fujitani et al; J. Immuno., 2002, 168, 443-449). In addition, exogenously administered CRTH2 agonists enhance the allergic response in sensitised mice (Spik et al; J. Immunol., 2005, 174, 3703-3708). In rats exogenously applied CRTH2 agonists cause a pulmonary eosinophilia but a DP agonist (BW 245C) or a TP agonist (I-BOP) showed no effect (Shirashi et al; J. Pharmacol. Exp Ther., 2005, 312, 954-960). These observations suggest that CRTH2 antagonists may have valuable properties for the treatment of diseases mediated by $PGD_2$.

In addition to Ramatroban a number of other CRTH2 antagonists have been described. Examples include: indoleacetic acids (WO2007/065684; WO2007/045867; WO2006/034419; WO2005/094816; WO2005/044260; WO2005/040114; WO2005/040112; GB2407318; WO2005/019171; WO2004/106302; WO2004/078719; WO2004/007451; WO2003/101981; WO2003/101961; WO2003/097598; WO2003/097042; WO2003/066047; WO2003/066046; WO2003/022813), quinolines (WO2007/036743), tetrahydroquinolines (WO2006/091674; US2005/256158; WO2005/100321; WO2005/007094; WO2004/035543; WO2004/032848; EP1435356; EP1413306), phenoxyacetic acids (WO2007/062678; WO2007/062773; WO2006/125596; WO2006/125593; WO2006/056752; WO2005/115382; WO2005/105727; WO2005/018529; WO2004/089885; WO2004/089884) and phenylacetic acids (WO2004/058164).

The quinoline template is a common one in compounds proposed for use as pharmaceuticals. However the compounds with which the present invention is concerned have a substitution pattern on the quinoline template which distinguishes them from specific known quinoline-type pharmaceuticals or known generally proposed classes of quinoline-type pharmaceuticals.

DETAILED DESCRIPTION OF THE INVENTION

A compound of formula (I) or a pharmaceutically acceptable salt thereof:

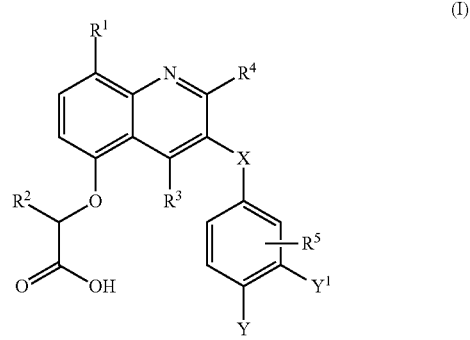

wherein:
$R^1$ is halogen or cyano;
$R^2$ is hydrogen or methyl;

$R^3$ and $R^4$ are independently —$OR^6$, $C_1$-$C_6$alkyl or $C_3$-$C_6$cycloalkyl, the latter two groups being optionally substituted by one or more halogen atoms;

$R^5$ is hydrogen or halogen;

$R^6$ is $C_1$-$C_6$alkyl or $C_3$-$C_6$cycloalkyl, either of which being optionally substituted by one or more halogen atoms;

X is —$CH_2$—, —S—, or —O—;

one of Y and $Y^1$ is hydrogen and the other is $OR^6$, —C(=O)$R^7$, $NR^8SO_2R^6$ or a heterocyclic group selected from furan, thiophene, pyrrole, oxazole, thiazole, imidazole, pyrazole, isoxazole, isothiazole, 1,2,3-oxadiazole, 1,2,4-oxadiazole, 1,3,4-oxadiazole, furazan, 1,2,3-triazole, 1,2,4-triazole, 1,2,3-thiadiazole, 1,2,5-thiadiazole, 1,3,4-thiadiazole, tetrazole, pyridine, pyridazine, pyrimidine, pyrazine, 1,2,4-triazine and 1,3,5-triazine any of which may be optionally substituted by one or more substituents selected from halogen; cyano; $C_1$-$C_6$alkyl optionally substituted by one or more halogen atoms; $C_3$-$C_6$cycloalkyl optionally substituted by one or more halogen atoms; hydroxy; $C_1$-$C_6$alkoxy optionally substituted by one or more halogen atoms; $C_1$-$C_6$alkyl-O—$CH_2$—, $C_1$-$C_6$alkyl-O—CH($R^X$)— and $C_1$-$C_6$alkyl-O—C($R^XR^Y$)— in which the $C_1$-$C_6$alkyl part is optionally substituted by one or more halogen atoms; $NH_2C$(=O)—; $R^XNHC$(=O)—; $R^XR^YNC$(=O)—; $R^XR^YNS$(=O)$_2$—; $R^XNHS$(=O)$_2$—; $NH_2S$(=O)$_2$—; $NH_2$—; $R^XNH$—; $R^XR^YN$—; $R^XS$(=O)$_2$—; $R^XC$(=O)—; $R^XS$(=O)$_2NH$—; $R^XS$(=O)$_2NR^Y$—; $R^XC$(=O)NH— and $R^XC$(=O)N($R^Y$)—; wherein $R^X$ and $R^Y$ are independently $C_1$-$C_4$alkyl or $C_3$-$C_6$cycloalkyl, either of which being optionally substituted by one or more halogen atoms; or $R^X$ and $R^Y$ when attached to the same nitrogen atom form a cyclic amino ring;

$R^7$ is $C_1$-$C_6$alkyl or $C_3$-$C_6$cycloalkyl either of which being optionally substituted by one or more halogen atoms; or phenyl or monocyclic heteroaryl having 5 or 6 ring atoms, optionally substituted by one or more substituent independently selected from halogen; cyano; $C_1$-$C_6$alkyl optionally substituted by one or more halogen atoms; $C_3$-$C_6$cycloalkyl optionally substituted by one or more halogen atoms; hydroxy; $C_1$-$C_6$alkoxy optionally substituted by one or more halogen atoms; $C_1$-$C_6$alkyl-O—$CH_2$—, $C_1$-$C_6$alkyl-O—CH($R^X$)— and $C_1$-$C_6$alkyl-O—C($R^XR^Y$)— in which the $C_1$-$C_6$alkyl part is optionally substituted by one or more halogen atoms; $NH_2C$(=)—; $R^XNHC$(=O)—; $R^XR^YNC$(=O)—; $R^XR^YNS$(=O)$_2$—; $R^XNHS$(=O)$_2$—; $NH_2S$(=O)$_2$—; $NH_2$—; $R^XNH$—; $R^XR^YN$—; $R^XS$(=O)$_2$—; $R^XC$(=O)—; $R^XS$(=O)$_2NH$—; $R^XS$(=O)$_2NR^Y$; $R^XC$(=O)NH— and $R^XC$(=O)N($R^Y$)—; wherein $R^X$ and $R^Y$ are independently $C_1$-$C_4$alkyl or $C_3$-$C_6$cycloalkyl, either of which being optionally substituted by one or more halogen atoms; or $R^X$ and $R^Y$ when attached to the same nitrogen atom form a cyclic amino ring; and $R^8$ is hydrogen, $C_1$-$C_6$alkyl or $C_3$-$C_6$cycloalkyl, the latter two groups being optionally substituted by one or more halogen atoms.

Compounds of formula (I) above may be prepared in the form of salts, N-oxides, hydrates, and solvates thereof. Any reference herein, including the claims herein, to "compounds with which the invention is concerned" or "compounds of formula (I)" and the like, includes reference to salts, particularly pharmaceutically acceptable salts, N-oxides, hydrates, and solvates of such compounds.

Compounds with which the invention is concerned are CRTH2 receptor antagonists, and are selective over the DP receptor.

A second aspect of the invention is (i) the use of a compound of formula (I) in therapy; (ii) the use of a compound of formula (I) in the manufacture of a medicament for use in the treatment of conditions responsive to modulation of CRTH2 receptor activity, and (iii) a method of treatment of conditions responsive to modulation of CRTH2 receptor activity, comprising administering to a patient suffering such disease an effective amount of a compound of formula (I) as defined above.

Examples of conditions responsive to modulation of CRTH2 receptor activity include asthma, rhinitis, allergic airway syndrome, allergic rhinobronchitis, bronchitis, chronic obstructive pulmonary disease (COPD), nasal polyposis, sarcoidosis, farmer's lung, fibroid lung, cystic fibrosis, chronic cough, conjunctivitis, atopic dermatitis, Alzheimer's disease, amyotrophic lateral sclerosis. AIDS dementia complex. Huntington's disease, frontotemporal dementia. Lewy body dementia, vascular dementia. Guillain-Barre syndrome, chronic demyelinating polyradiculoneuropathy, multifocal motor neuropathy, plexopathy, multiple sclerosis, encephalomyelitis, panencephalitis, cerebellar degeneration and encephalomyelitis. CNS trauma, migraine, stroke, rheumatoid arthritis, ankylosing spondylitis, Behçet's Disease, bursitis, carpal tunnel syndrome, inflammatory bowel disease. Crohn's disease, ulcerative colitis, dermatomyositis, Ehlers-Danlos Syndrome (EDS), fibromyalgia, myofascial pain, osteoarthritis (OA), osteonecrosis, psoriatic arthritis. Reiter's syndrome (reactive arthritis), sarcoidosis, scleroderma, Sjogren's Syndrome, soft tissue disease, Still's Disease, tendinitis, polyarteritis Nodossa, Wegener's Granulomatosis, myositis (polymyositis dermatomyositis), gout, atherosclerosis, lupus erythematosus, systemic lupus erythematosus (SLE), type I diabetes, nephritic syndrome, glomerulonephritis, acute and chronic renal failure, eosinophilia fascitis, hyper IgE syndrome, sepsis, septic shock, ischemic reperfusion injury in the heart, allograft rejection after transplantations, and graft versus host disease.

However, the compounds with which the invention is concerned are primarily of value for the treatment of asthma, chronic obstructive pulmonary disease, rhinitis, allergic airway syndrome, or allergic rhinobronchitis. Psoriasis, atopic and non-atopic dermatitis Crohn's disease, ulcerative colitis, and irritable bowel disease are other specific conditions where the present compounds may have particular utility.

A third aspect of the invention is a pharmaceutical composition comprising a compound of formula (I), in admixture with a pharmaceutically acceptable carrier or excipient.

Terminology

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "carbocyclic" refers to an optionally substituted mono-, bi- or tricyclic radical having up to 16 ring atoms, all of which are carbon, and includes aryl and cycloalkyl.

As used herein the term "cycloalkyl" refers to an optionally substituted monocyclic saturated carbocyclic radical having from 3-6 carbon atoms and includes, for example, cyclopropyl, cyclobutyl, cyclopentyl, cyclohexyl, cycloheptyl and cyclooctyl.

As used herein the unqualified term "aryl" refers to an optionally substituted mono-, bi- or tri-cyclic carbocyclic aromatic radical, and includes radicals having two monocyclic carbocyclic aromatic rings which are directly linked by a covalent bond. Aryl radicals may have, for example, from 6 to 14 ring carbon atoms, preferably from 6 to 10 carbon atoms. Illustrative of aryl radicals are phenyl, biphenyl and napthyl.

As used herein the unqualified term "heteroaryl" refers to an optionally substituted mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocycloalkyl" or "heterocyclyl" or "heterocyclic" includes "heteroaryl" as defined above, and in addition means an optionally substituted mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, quinolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, cycloalkyl, ($C_1$-$C_6$)alkoxy, hydroxy, hydroxy($C_1$-$C_6$) alkyl, mercapto, mercapto($C_1$-$C_6$)alkyl, ($C_1$-$C_6$)alkylthio, phenyl, monocyclic heteroaryl having 5 or 6 ring atoms, halo (including fluoro, bromo and chloro), trifluoromethyl, trifluoromethoxy, nitro, nitrile (—CN), oxo, —COOH, —COO$R^A$, —CO$R^A$, —SO$_2$$R^A$, —CONH$_2$, —SO$_2$NH$_2$, —CONH$R^A$, —SO$_2$NH$R^A$, —CON$R^A$$R^B$, —SO$_2$N$R^A$$R^B$, —NH$_2$, —NH$R^A$, —N$R^A$$R^B$, —OCONH$_2$, —OCONH$R^A$, —OCON$R^A$$R^B$, —NHCO$R^A$, —NHCOO$R^A$, —N$R^B$COO$R^A$, —NHSO$_2$O$R^A$, —N$R^B$SO$_2$OH, —N$R^B$SO$_2$O$R^A$, —NHCONH$_2$, —N$R^A$CONH$_2$, —NHCONH$R^B$, —N$R^A$CONH$R^B$, —NHCON$R^A$$R^B$, or —N$R^A$CON$R^A$$R^B$ wherein $R^A$ and $R^B$ are independently a ($C_1$-$C_6$)alkyl, ($C_3$-$C_6$) cycloalkyl, phenyl, or monocyclic heterocyclic group having 5 or 6 ring atoms, or $R^A$ and $R^B$ when attached to the same nitrogen atom may form a ring with that nitrogen of 5 or 6 ring atoms, optionally containing further heteroatoms selected from N, O or S (examples being morpholinyl, piperidinyl, piperizinyl, 4-methylpiperizinyl, and tetrahydropyrrolyl). An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Specific salts with bases include the benzathine, calcium, diolamine, meglumine, olamine, potassium, procaine, sodium, tromethamine and zinc salts. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. Where a compound contains a quaternary ammonium group acceptable counter-ions may be, for example, chlorides, bromides, sulfates, methanesulfonates, benzenesulfonates, toluenesulfonates (tosylates), napadisylates (naphthalene-1,5-disulfonates or naphthalene-1-(sulfonic acid)-5-sulfonates), edisylates (ethane-1,2-disulfonates or ethane-1-(sulfonic acid)-2-sulfonates), isethionates (2-hydroxyethylsulfonates), phosphates, acetates, citrates, lactates, tartrates, mesylates, maleates, malates, fumarates, succinates, xinafoates, p-acetamidobenzoates and the like; wherein the number of quaternary ammonium species balances the pharmaceutically acceptable salt such that the compound has no net charge.

Salts are discussed in the "Handbook of Pharmaceutical Salts. Properties, selection and use", P. Heinrich Stahl & Camille G. Wermuth, Wiley-VCH, 2002.

Compounds with which the invention is concerned may exist in one or more stereoisomeric form, because of the presence of asymmetric atoms or rotational restrictions, and in such cases can exist as a number of stereoisomers with R or S stereochemistry at each chiral centre or as atropisomers with R or S stereochemistry at each chiral axis. The invention includes all such enantiomers and diastereoisomers and mixtures thereof.

Compounds of the invention may, in appropriate cases be administered as prodrugs, such as esters, of compounds with which the invention is concerned. "Prodrug" means a compound which is convertible in vivo by metabolic means (e.g. by hydrolysis, reduction or oxidation) to a compound of formula (I). For example an ester prodrug of a compound of formula (I) may be convertible by hydrolysis in vivo to the parent molecule. Suitable esters of compounds of formula (I) are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates. Examples of ester prodrugs are those described by F. J. Leinweber, Drug Metab. Res., 1987, 18, 379. As used in herein, references to the compounds of formula (I) are meant to also include the prodrug forms.

The variables $R^1$-$R^5$, A, B, X, Y and $Y^1$

For use in accordance with the invention, the following structural characteristics are currently preferred, in any compatible combination, in the compounds (1) defined above:

$R^1$ is halogen, such as fluoro, chloro or bromo. Presently fluoro and chloro are preferred.

$R^2$ is hydrogen or methyl.

$R^3$ and $R^4$ are independently $C_1$-$C_6$alkyl, for example methyl, ethyl, or n- or iso-propyl; fully or partially halogenated, especially fluorinated. $C_1$-$C_6$alkyl, for example trifluoromethyl or difluoromethyl; ($C_3$-$C_6$)cycloalkyl, for example cyclopropyl, fully or partially halogenated, especially fluorinated ($C_3$-$C_6$)cycloalkyl; or a group —O$R^6$; wherein $R^6$ is $C_1$-$C_6$alkyl, for example methyl, ethyl, or n- or iso-propyl; fully or partially halogenated, especially fluorinated, $C_1$-$C_6$alkyl, for example trifluoromethyl or difluoromethyl; ($C_3$-$C_6$)cycloalkyl, for example cyclopropyl or fully or partially halogenated, especially fluorinated ($C_3$-$C_6$)cycloalkyl.

In some embodiments of the invention one of $R^3$ and $R^4$ is methyl or ethyl, and the other is difluoromethoxy. In other embodiments of the invention $R^4$ is ethyl, isopropyl, cyclopropyl, or difluoromethoxy, and $R^3$ is difluoromethoxy or, methyl.

X is —$CH_2$—, —S— or —O—.

One of Y and $Y^1$ is hydrogen and the other is —$OR^6$, —C(=O)$R^7$, $NR^8SO_2R^6$ or a heterocyclic group, all as defined in relation to formula (I). Examples of Y and $Y^1$ when not hydrogen are:

—$OR^6$, —C(=O)$R^7$, or —$NR^8SO_2R^6$ wherein $R^6$ is methyl, ethyl, n- or iso-propyl, n-, sec, or tert-butyl, cyclopropyl, difluoromethyl, trifluoromethyl; or cyclopropyl, cyclopentyl or cyclohexyl; and $R^7$ is methyl, ethyl, n- or iso-propyl, n-, sec, or tert-butyl, cyclopropyl, difluoromethyl, trifluoromethyl; or phenyl, cyclopropyl, cyclopentyl or cyclohexyl, all optionally ring-substituted by, for example, one or more of fluoro, chloro, cyano, methyl, ethyl, trifluoromethyl, difluoromethyl or cyclopropyl; and $R^8$ is hydrogen or methyl.

Heterocyclic rings selected from furan, thiophene, pyrrole, oxazole, thiazole, imidazole, pyrazole, isoxazole, isothiazole, 1,2,3-oxadiazole, 1,2,4-oxadiazole, 1,3,4-oxadiazole, furazan, 1,2,3-triazole, 1,2,4-triazole, 1,2,3-thiadiazole, 1,2,5-thiadiazole, 1,3,4-thiadiazole, tetrazole, pyridine, pyridazine, pyrimidine, pyrazine, 1,2,4-triazine and 1,3,5-triazine, any of which may be optionally substituted by one or more substituents independently selected from, for example fluoro, chloro, cyano, methyl, ethyl, trifluoromethyl, difluoromethyl, cyclopropyl, trifluoromethoxy, methoxymethyl, EtNHC(=O)—, $Et_2$NC(=O)—, $Et_2$NS(=O)$_2$—, EtNHS(=O)$_2$—, EtNH—, $Et_2$N—, MeS(=O)$_2$—, t-BuC(=O)—, EtS(=O)$_2$NH—, EtS(=O)$_2$NMe-, and MeC(=O)NH—.

One particular subclass of compounds of the invention consists of compounds of formula (I) above wherein $R^1$ is chloro or fluoro. $R^2$ is hydrogen or methyl. $R^3$ is methyl or difluoromethoxy, $R^4$ is ethyl, isopropyl or difluoromethoxy, $R^5$ is hydrogen, fluoro or chloro, one of Y and $Y^1$ is hydrogen and the other is pyrimidin-2-yl, pyrazol-1-yl, pyrazol-3-yl, pyrazol-4-yl, imidazol-1-yl, imidazol-2-yl, thiazol-2-yl, oxazol-2-yl or isoxazol-4-yl, any of which may be optionally substituted by one or more substituents selected from fluoro, chloro cyano methyl, ethyl, isopropyl, trifluoromethyl, difluoromethyl, cyclopropyl, hydroxy, methoxy, ethoxy, ispropoxy, difluoromethoxy, trifluoromethoxy, Z—O—$CH_2$—, Z—O—CH($R^X$)— and Z—O—C($R^X R^Y$)—, $NH_2$C(=O)—; $R^X$NHC(=O)—; $R^XR^Y$NC(=O)—; $R^XR^Y$NS(=O)$_2$—; $R^X$NHS(=O)$_2$—; $NH_2$S(=O)$_2$—; $NH_2$—; $R^X$NH—; $R^XR^Y$N—; $R^X$S(=O)$_2$—; $R^X$C(=O)—; $R^X$S(=O)$_2$NH—; $R^X$S(=O)$_2NR^Y$—; $R^X$C(=O)NH— and $R^X$C(=O)N($R^Y$)—; wherein Z is selected from methyl, ethyl, isopropyl, trifluoromethyl, difluoromethyl, and cyclopropyl, and $R^X$ and $R^Y$ are independently methyl, ethyl, isopropyl, trifluoromethyl, difluoromethyl, or cyclopropyl, or $R^X$ and $R^Y$ when attached to the same nitrogen atom form a morpholino, piperidinyl, or piperazinyl ring, the latter being optionally N-substituted by methyl, ethyl, isopropyl or cyclopropyl.

Specific compounds with which the invention is concerned include those of the Examples herein, and pharmaceutically acceptable salts. N-oxides, hydrates or solvates thereof.

Compositions

As mentioned above, the compounds with which the invention is concerned are CRTH2 receptor antagonists, and are useful in the treatment of diseases which benefit from such modulation. Examples of such diseases are referred to above, and include asthma. COPD, rhinitis, allergic airway syndrome, and bronchitis.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range will lie within the range of from about 0.001 mg to about 100 mg per kg body weight of a mammal, often 0.01 mg to about 50 mg per kg, for example 0.1 to 10 mg per kg, in single or divided doses. On the other hand, it may be necessary to use dosages outside these limits in some cases.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The drug may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

Other compounds may be combined with compounds of this invention of formula [I] for the prevention and treatment of prostaglandin-mediated diseases. Thus the present invention is also concerned with pharmaceutical compositions for preventing and treating $PGD_2$-mediated diseases comprising a therapeutically effective amount of a compound of the invention of formula [I] and one or more other therapeutic agents. Suitable therapeutic agents for a combination therapy with compounds of formula [1] include, but are not limited to: (1) corticosteroids, such as fluticasone, ciclesonide or budesonide; (2) β2-adrenoreceptor agonists, such as salmeterol, indacaterol or formoterol; (3) leukotriene modulators, for example leukotriene antagonists such as montelukast, zafirulast or pranlukast or leukotriene biosynthesis inhibitors such as Zileuton or BAY-1005; (4) anticholinergic agents, for example muscarinic-3 (M3) receptor antagonists such as tiotropium bromide; (5) phosphodiesterase-IV (PDE-IV) inhibitors, such as roflumilast or cilomilast; (6) antihistamines, for example selective histamine-1 (H1) receptor antagonists, such as fexofenadine, citirizine, loratidine or astemizole; (7) antitussive agents, such as codeine or dextramorphan; (8) non-selective COX-1/COX-2 inhibitors, such as ibuprofen or ketoprofen; (9) COX-2 inhibitors, such as celecoxib and rofecoxib; (10) VLA-4 antagonists, such as those described in WO97/03094 and WO97/02289; (11) TACE inhibitors and TNF-α inhibitors, for example anti-TNF monoclonal antibodies, such as Remicade and CDP-870 and TNF receptor immunoglobulin molecules, such as Enbrel; (12) inhibitors of matrix metalloprotease, for example MMP12; (13) human neutrophil elastase inhibitors, such as those described in WO2005/026124. WO2003/053930 and WO06/082412; (14) A2a agonists such as those described in EP1052264 and EP1241176 (15) A2b antagonists such as those described in WO2002/42298; (16) modulators of chemokine receptor function, for example antagonists of CCR3 and CCR8; (17) compounds which modulate the action of other prostanoid receptors, for example a DP receptor antagonist or a thromboxane $A_2$ antagonist; and (18) agents that modulate Th2 function, such as PPAR agonists The weight ratio of the compound of the invention to the second active ingredient may be varied and will depend upon the effective dose of each ingredient. Generally, an effective dose of each will be used.

Methods of Synthesis

The present invention is also concerned with processes for preparing the compounds of this invention.

The compounds of formula [I] of the present invention can be prepared according to the procedures of the following schemes and examples, using appropriate materials, and are further exemplified by the following specific examples. Moreover, by utilizing the procedures described with the disclosure contained herein, one of ordinary skill in the art can readily prepare additional compounds of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

Compounds of the invention of formula [Ia] may conveniently be prepared by the reaction between an intermediate compound of formula [II] and a suitable alkylating agent of formula [III], wherein group LG represents a suitable leaving group (for example, chloro, bromo, or methanesulfonyloxy) and $R^9$ is a hydrogen or alkyl group. Typically, the alkylation reaction is carried out in the presence of a base (for example, potassium carbonate) in an inert solvent (for example, acetone or N,N-dimethylformamide). It is to be understood that if the reaction is carried out on a protected form of [III] an appropriate deprotection step will be required to obtain the desired compound of the invention of formula [Ia](Scheme 1).

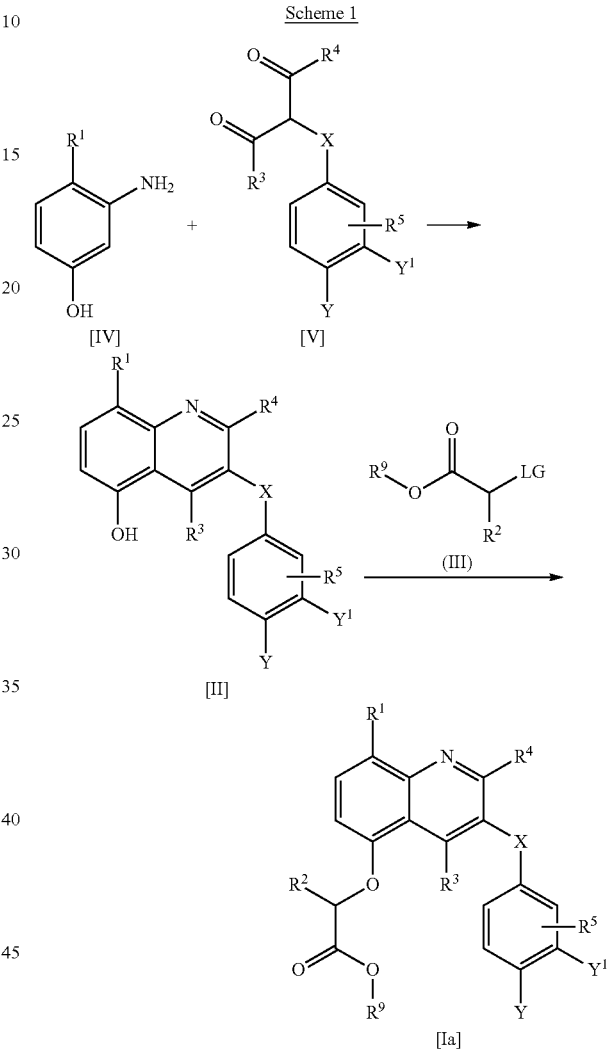

Scheme 1

Intermediate compounds of formula [II] may be prepared by the reaction between an aminophenol of formula [IV] and a 1,3-dicarbonyl compound of formula [V]. The reaction may be carried out neat or in the presence of a suitable dehydrating agent, such as polyphosphoric acid, p-toluenesulfonic acid or methanesulfonic acid. Intermediate compounds of formula [III], [IV] and [V] are commercially available or can be prepared by known methods.

Alternatively, intermediate compounds of formula [II], wherein $R^4$ is an alkyl group, such as isopropyl or cyclopropyl, may be prepared from intermediate compounds of formula [VI], wherein T is chloro, bromo or iodo atom, or a trifluoromethanesulfonyl-oxy group, by reaction with an organometallic reagent of formula [VII], wherein B is an appropriately substituted boron, zinc or tin group (Scheme 2). The reaction may conveniently be carried out in the presence of a suitable catalyst such as tetrakis(triphenylphosphine) palladium. Compounds of formula [VII] are commercially available or can be prepared by known methods.

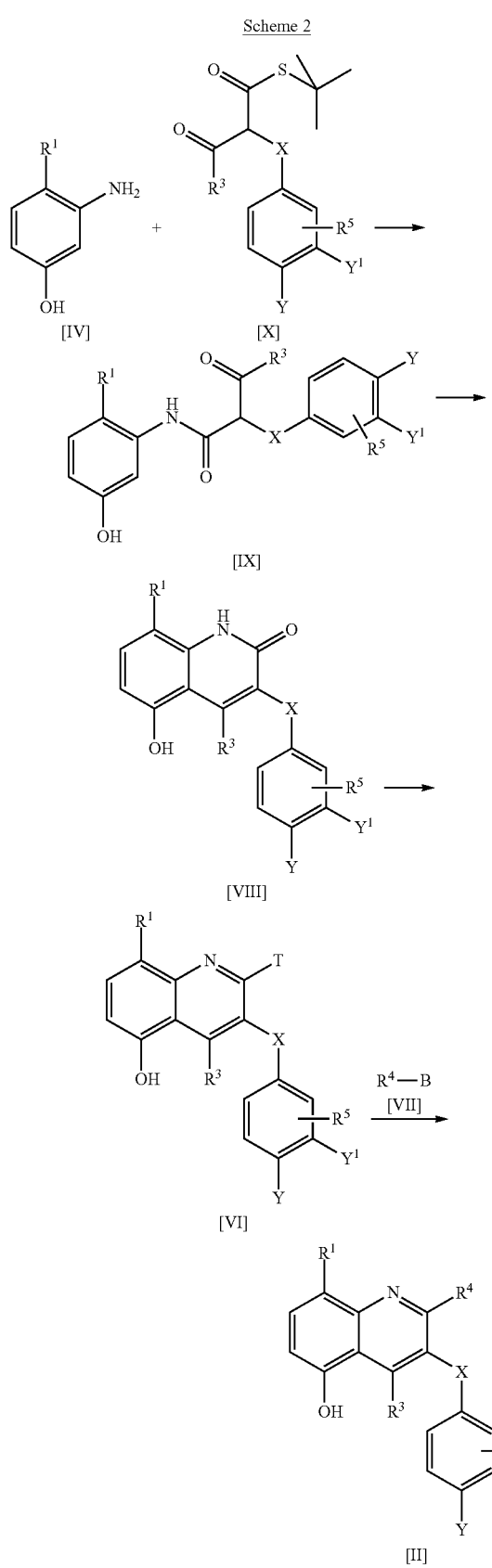

Scheme 2

Intermediate compounds of formula [VI], wherein T is chloro atom, may be prepared by treatment of compounds of formula [VIII] with phosphorus oxychloride. Intermediate compounds of formula [VIII] may be prepared from compounds of formula [IX]. The reaction may be carried in the presence of a suitable dehydrating agent, for example methanesulfonic acid or p-toluenesulfonic acid. Intermediate compounds of formula [IX] may be prepared from reaction of aminophenols of formula [IV] with β-ketothioesters of formula [X] in the presence of silver trifluoroacetate. Compounds of formula [X] are known or may be prepared from known compounds according to methods known to those skilled in the art.

Compounds of formula [Ia], wherein $R^4$ is an alkoxy group, such as difluoromethoxy, may conveniently be prepared from intermediate compounds of formula [XI] by alkylation with chlorodifluoromethane (Scheme 3). It is to be understood that if the reaction is carried out on a protected form of intermediate [XI] an appropriate deprotection step will be required to obtain the desired compound [Ia].

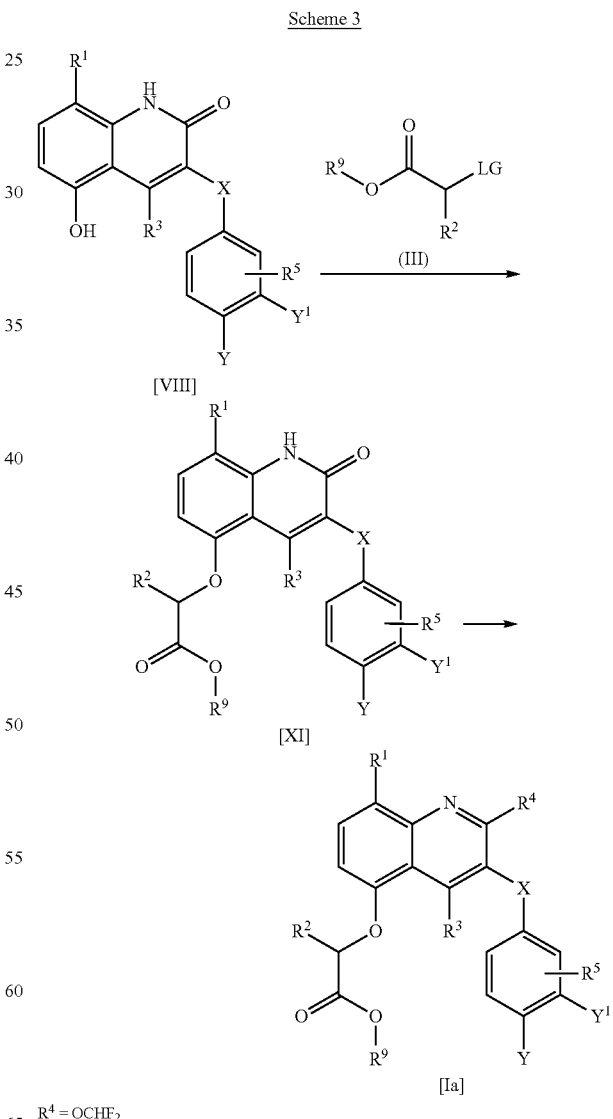

Scheme 3

Intermediate compounds of formula [XI] may be prepared from compounds of formula [III] and [VIII] using methods described above for the preparation of compounds of formula [Ia] from intermediate compounds of formula [II] (Scheme 1).

Compounds of formula [Ia], wherein R³ is an alkoxy group, such as difluoromethoxy, may conveniently be prepared from the reaction of aniline of formula [XIV] and a β-ketoester of formula [XIII], wherein R¹⁰ represents an appropriate alkyl group, such as methyl and ethyl, followed by alkylation with chlorodifluoromethane (Scheme 4). It is to be understood that if the reaction is carried out on a protected form of intermediate [XIV] an appropriate deprotection step will be required to obtain the desired compound [Ia].

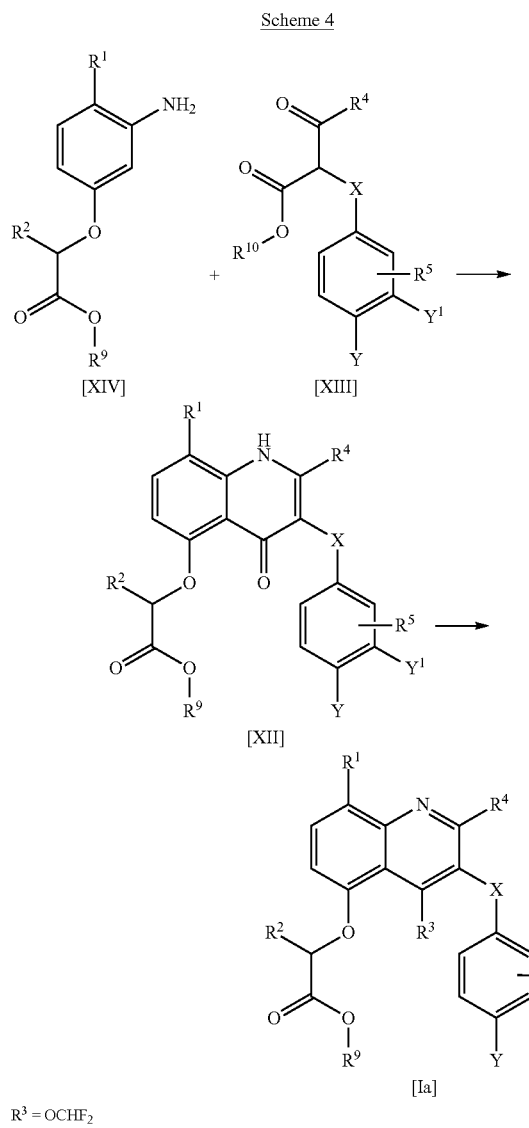

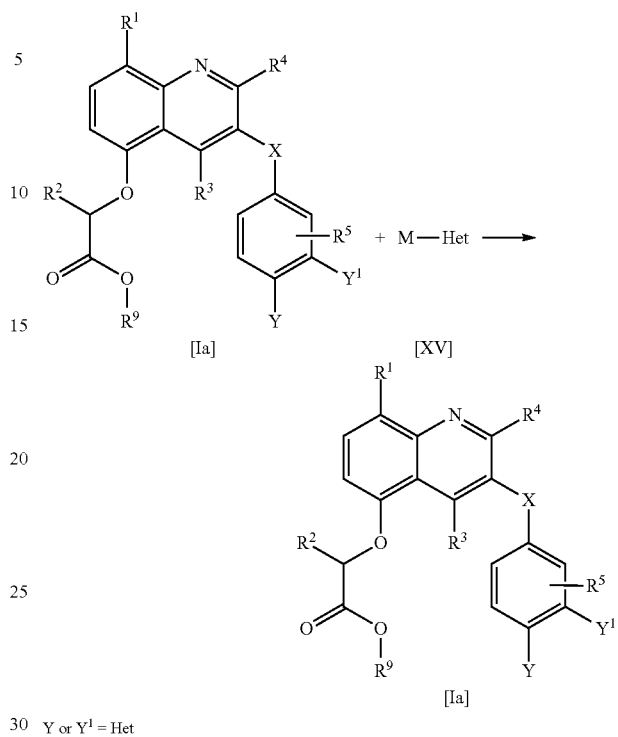

Intermediate compounds of formula [XIV] may be prepared from compounds of formula [IV] using methods described above for the preparation of compounds of formula [Ia] from intermediate compounds of formula [II] (Scheme 1). Ketoesters of formula [XIII] are known or may be prepared from known compounds according to methods known to those skilled in the art.

Alternatively, compounds of formula [Ia], wherein Y or Y¹ represents a heterocyclic group, may be conveniently prepared from compounds of formula [Ia], wherein Y or Y¹ represents chloro, bromo, or iodo atom, or a trifluoromethanesulfonyloxy group, by reaction with an organometallic reagent of formula [XV] wherein Het represents a 5- or 6-membered heteroaryl ring and M represents an appropriately substituted boron, zinc, tin, copper or silicon group (Scheme 5). The reaction may conveniently be carried out in the presence of a suitable catalyst such as a palladium compound (for example, tetrakis(triphenylphosphine)palladium or [1,1'-bis(diphenylphosphino) ferrocene]dichloropalladium).

EXAMPLES

The invention will now be described with reference to the following examples. It will be appreciated that the invention is described by way of example only and modification of detail may be made without departing from the scope of the invention.

¹H NMR spectra were recorded at ambient temperature using a Varian Unity Inova (400 MHz) spectrometer with a triple resonance 5 mm probe spectrometer. Chemical shifts are expressed in ppm relative to tetramethylsilane. The following abbreviations have been used: br s=broad singlet, s=singlet, d=doublet, dd=double doublet, t=triplet, q=quartet, m=multiplet.

Mass Spectrometry (LCMS) experiments to determine retention times and associated mass ions were performed using the following methods:

Method A: experiments were performed on a Micromass Platform LCT spectrometer with positive ion electrospray and single wavelength UV 254 nm detection using a Higgins Clipeus C18 5 μm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Method B: experiments were performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% solvent A and 5 c/0 solvent B for the first 0.50 minutes followed by a gradient up to 5% solvent A and 95% solvent B over the next 4 minutes. The final solvent system was held constant for a further 0.50 minutes Microwave experiments were carried out using a Personal Chemistry Smith Synthesizer™, which uses a single-mode resonator and dynamic field tuning, both of which give reproducibility and control. Temperatures from 40-250° C. can be achieved, and pressures of up to 20 bars can be reached. Two types of vial are available for this processor, 0.5-2.0 mL and 2.0-5.0 mL.

Reverse-phase preparative HPLC purifications were carried out using Genesis 7 micron C-18 bonded silica stationary phase in columns 10 cm in length and 2 cm internal diameter. The mobile phase used was mixtures of acetonitrile and water (both buffered with 0.1 v/v trifluoroacetic acid or formic acid) with a flow rate of 10 mL per minute and typical gradients of 40 to 90% organic modifier ramped up over 30 to 40 minutes. Fractions containing the required product (identified by LC-MS analysis) were pooled, the organic fraction removed by evaporation, and the remaining aqueous fraction lyophilised, to give the final product.

Example 1

[4-difluoromethoxy-2-ethyl-8-fluoro-3-(4-pyrazol-1-ylbenzyl)quinolin-5-yloxy]acetic acid

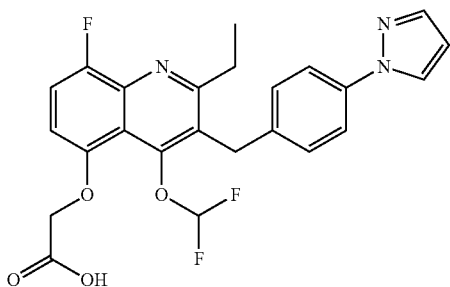 [SMILES: CCc1nc2c(F)ccc(OCC(=O)O)c2c(OC(F)F)c1Cc1ccc(-n2cccn2)cc1]

Preparation 1a (3-amino-4-fluorophenoxy)acetic acid methyl ester

3-Amino-4-fluorophenol (3.0 g) was added to a stirred suspension of sodium hydride (60% in oil, 0.94 g) in N,N-dimethylformamide (30 mL) at 0° C., and the resulting mixture was warmed to room temperature for 15 minutes. The mixture was cooled to 0° C. treated with bromoacetic acid methyl ester (3.3 g), and then stirred at room temperature for 2 hours. The mixture was treated with dilute aqueous ammonium chloride solution and extracted with ethyl acetate. The combined extracts were washed with saturated aqueous sodium chloride solution, dried over magnesium sulfate and the solvent removed under reduced pressure. Purification of the residue by column chromatography on silica gel, eluting with a mixture of toluene, dichloromethane and ethyl acetate (2:1:0, 0:1:0 to 0:20:1 by volume) gave title compound (2.7 g).

$^1$H NMR (DMSO-d6): 3.70 (s, 3H), 4.65 (s, 2H), 5.15 (br s, 2H), 6.00 (dt, J=3.1, 8.8 Hz, 1H), 6.30 (dd, J=3.1, 7.6 Hz, 1H), 6.85 (dd, J=8.8, 11.2 Hz, 1H)

MS: ESI (+ve) (Method B): 200 (M+H)$^+$, Retention time 2.5 min.

Preparation 1b 3-oxo-2-(4-pyrazol-1-ylbenzyl)pentanoic acid ethyl ester

A suspension of potassium tert-butoxide (0.57 g) in tetrahydrofuran (40 mL) at 0° C. was treated with a mixture of tert-butanol (2.0 mL) and 3-oxopentanoic acid ethyl ester (0.73 mL), and the resulting mixture was stirred at 0° C. for 45 minutes. The mixture was then treated with a solution of 1-(4-bromomethylphenyl)-1H-pyrazole (1.0 g) in tetrahydrofuran (10 mL), and stirred at 0° C. for 2 hours. The mixture was diluted with water, concentrated to low bulk under reduced pressure, and the residue extracted with ethyl acetate. The combined extracts were washed with saturated aqueous sodium chloride solution, dried over magnesium sulfate and then concentrated under reduced pressure. Purification of the residue by column chromatography on silica gel, eluting with a mixture of cyclohexane and ethyl acetate gave title compound as a pale yellow oil (0.63 g).

MS: ESI (+ve) (Method B): 301 (M+H)$^+$, Retention time 3.3 min

Preparation 1c

[2-ethyl-8-fluoro-4-oxo-3-(4-pyrazol-1-ylbenzyl)-1,4-dihydroquinolin-5-yloxy]acetic acid methyl ester A solution of (3-amino-4-fluorophenoxy)acetic acid methyl ester (0.42 g) and 3-oxo-2-(4-pyrazol-1-ylbenzyl)pentanoic acid ethyl ester (0.63 g) in 1,4-dioxane (20 mL) was added to polyphosphoric acid (3 g) at 100° C., and the resulting mixture was stirred at 120° C. for 18 hours. The mixture was cooled to room temperature, diluted with water and extracted with ethyl acetate. The combined extracts were washed with water and saturated aqueous sodium chloride solution, and then dried over magnesium sulfate. The solvent was removed under reduced pressure and the residue purified by column chromatography on silica gel, eluting with a mixture of cyclohexane and ethyl acetate to afford title compound (0.39 g).

MS: ESI (+ve) (Method B): 435 (M+H)$^+$, Retention time 2.9 min.

Preparation 1d

[4-difluoromethoxy-2-ethyl-8-fluoro-3-(4-pyrazol-1-ylbenzyl)quinolin-5-yloxy]acetic acid methyl ester A mixture of [2-ethyl-8-fluoro-4-oxo-3-(4-pyrazol-1-ylbenzyl)-1,4-dihydroquinolin-5-yloxy]acetic acid methyl ester (0.37 g), N,N-dimethylformamide (10 mL), potassium carbonate (0.18 g) and acetic acid chlorodifluoromethyl ester (0.27 mL) was stirred at 80° C. for 6 hours. The mixture was cooled to room temperature, diluted with water and extracted with ethyl acetate. The combined extracts were washed with saturated aqueous sodium chloride solution, dried over magnesium sulfate and concentrated under reduced pressure. Purification of the residue by column chromatography on silica gel, eluting with a mixture of cyclohexane and ethyl acetate gave title compound (0.19 g).

MS: ESI (+ve) (Method 8): 486 (M+H)$^+$, Retention time 3.7 min.

Preparation 1e

[4-difluoromethoxy-2-ethyl-8-fluoro-3-(4-pyrazol-1-yl-benzyl)quinolin-5-yloxy]acetic acid A solution of [4-difluoromethoxy-2-ethyl-8-fluoro-3-(4-pyrazol-1-ylbenzyl)quinolin-5-yloxy]acetic acid methyl ester (0.19 g) in tetrahydrofuran (5.0 mL) was treated with 1.0 M aqueous lithium hydroxide solution (0.78 ml), and the resulting solution was stirred at room temperature for 1 hour. The tetrahydrofuran was removed under reduced pressure and the residue acidified by the addition of 0.1M aqueous hydrochloric acid. The mixture was extracted with ethyl acetate and the combined extracts were washed with saturated aqueous sodium chloride solution, and than dried over magnesium sulfate. The solvent was removed under reduced pressure to afford title compound (0.18 g).

$^1$H NMR (CDCl$_3$): δ 1.25 (t, J=7.5 Hz, 3H), 2.90 (q, J=7.5 Hz, 2H), 4.40 (s, 2H), 4.80 (s, 2H), 6.40 (m, 1H), 6.75 (dd, J=3.5, 8.8 Hz, 1H), 6.85 (t, J=75 Hz, 1H), 7.15 (d, J=8.6 Hz, 2H), 7.25 (t, J=8.8 Hz, 1H), 7.50 (d, J=8.6 Hz, 2H), 7.70 (d, J=2.0 Hz, 1H), 7.85 (d, J=2.0 Hz, 1H)

MS: ESI (+ve) (Method A): 472 (M+H)$^+$, Retention time 11.1 min

MS: ESI (+ve) (Method B): 472 (M+H)$^+$, Retention time 3.3 min

Example 2

[4-difluoromethoxy-2-ethyl-8-fluoro-3-(4-oxazol-2-ylbenzyl)quinolin-5-yloxy]acetic acid

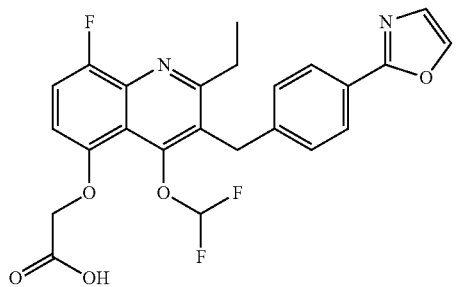

Preparation 2a 2-(4-bromobenzyl)-3-oxopentanoic acid ethyl ester

The title compound was prepared by the method of Preparation 1b using 3-oxopentanoic acid ethyl ester and 1-bromo-4-bromomethylbenzene.

$^1$H NMR (CDCl$_3$): δ 1.05 (t, J=7.3 Hz, 3H), 1.25 (t, J=7.1 Hz, 3H), 2.35 (m, 1H), 2.60 (m, 1H), 3.10 (m, 2H), 3.75 (t, J=7.6 Hz, 1H), 4.15 (m, 2H), 7.05 (d, J=8.5 Hz, 2H), 7.40 (d, J=8.5 Hz, 2H)

Preparation 2h

[3-(4-bromobenzyl)-2-ethyl-8-fluoro-4-oxo-1,4-dihydroquinolin-5-yloxy]acetic acid methyl ester The title compound was prepared by the method of Preparation 1c using (3-amino-4-fluorophenoxy)acetic acid methyl ester and 2-(4-bromobenzyl)-3-oxopentanoic acid ethyl ester.

MS: ESI (+ve) (Method B): 448 (M+Hr, Retention time 3.2 min

Preparation 2c

[3-(4-bromobenzyl)-4-difluoromethoxy-2-ethyl-8-fluoroquinolin-5-yloxy]acetic acid methyl ester The title compound was prepared by the method of Preparation 1d using [3-(4-bromobenzyl)-2-ethyl-8-fluoro-4-oxo-1,4-dihydroquinolin-5-yloxy]acetic acid methyl ester and acetic acid chlorodifluoromethyl ester.

MS: ESI (+ve) (Method B): 498 (M+H)$^+$, Retention time 4.1 min

Preparation 2d

[4-difluoromethoxy-2-ethyl-8-fluoro-3-(4-oxazol-2-ylbenzyl)quinolin-5-yloxy]acetic acid methyl ester A mixture of [3-(4-bromobenzyl)-4-difluoromethoxy-2-ethyl-8-fluoroquinolin-5-yloxy]acetic acid methyl ester (0.36 g), 2-tributylstannanyloxazole (0.46 mL), tetrakis(triphenylphosphine)palladium(0) (0.084 g) and 1,4-dioxane (3.0 mL) was heated at 100° C. for 3 hours. The mixture was cooled to room temperature, diluted with ethyl acetate, washed with water, and then dried over magnesium sulfate. The solvent was removed under reduced pressure to afford title compound as a yellow gum (1.1 g).

MS: ESI (+ve) (Method B): 487 (M+H)$^+$, Retention time 3.8 min

Preparation 2e

[4-difluoromethoxy-2-ethyl-8-fluoro-3-(4-oxazol-2-ylbenzyl)quinolin-5-yloxy]acetic acid A solution of [4-difluoromethoxy-2-ethyl-8-fluoro-3-(4-oxazol-2-ylbenzyl)quinolin-5-yloxy]acetic acid methyl ester (0.73 g) in methanol (6.0 mL) and water (0.6 mL) was treated with 5.0 M aqueous lithium hydroxide solution (0.30 mL), and the resulting mixture was stirred at room temperature for 2 hours. The mixture was acidified by the addition of glacial acetic acid, concentrated under reduced pressure, and the residue partitioned between ethyl acetate and water. The organic phase was dried over magnesium sulfate, concentrated under reduced pressure, and then diluted with acetonitrile. The resulting precipitate was removed by filtration, washed with acetonitrile, and the filtrate concentrated under reduced pressure. The residue was purified by column chromatography on silica gel, eluting with a mixture of dichloromethane, methanol and glacial acetic acid (50:1:1 to 10:1:1 by volume). Further purification by preparative reverse-phase HPLC, and then column chromatography on silica gel, eluting with a mixture of dichloromethane, methanol and glacial acetic acid (40:1:0.1 to 20:1:0.1 by volume) gave title compound as a white solid (0.082 g).

$^1$H NMR (DMSO-d6): δ 1.15 (t, J=7.5 Hz, 3H), 2.80 (q, J=7.5 Hz, 2H), 4.35 (s, 2H), 4.85 (s, 2H), 7.00 (dd, J=3.7, 5.2

Hz, 1H), 7.20 (d, J=8.5 Hz, 2H), 7.25 (t, J=75 Hz, 1H), 7.30 (s, 1H), 7.50 (dd, J=8.9, 10.1 Hz, 1H), 7.85 (d, J=8.5 Hz, 2H), 8.15 (s, 1H)

MS: ESI (+ve) (Method A): 473 (M+H)⁺, Retention time 10.9 min

MS: ESI (+ve) (Method B): 473 (M+H)⁺, Retention time 3.2 min

Example 3

[4-difluoromethoxy-2-ethyl-8-fluoro-3-(4-methoxybenzyl)quinolin-5-yloxy]acetic acid

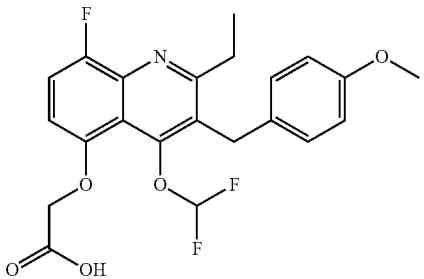 [SMILES: CCc1nc2c(F)ccc(OCC(=O)O)c2c(OC(F)F)c1Cc1ccc(OC)cc1]

Preparation 3a 2-(4-methoxybenzyl)-3-oxopentanoic acid ethyl ester

A mixture of potassium tert-butoxide (5.4 g), tetrahydrofuran (80 mL), tert-butanol (0.1 mL) and 3-oxopentanoic acid ethyl ester (5.0 g) at 0° C. was treated with a solution of 1-chloromethyl-4-mothoxybenzene (4.7 mL) in tetrahydrofuran (20 mL), and the resulting mixture was stirred at 0° C. for 30 minutes, and then at room temperature for 24 hours. The mixture was diluted with saturated aqueous ammonium chloride solution and extracted with ethyl acetate. The combined extracts were dried over sodium sulfate and the solvent removed under reduced pressure. Purification of the residue by column chromatography on silica gel, eluting with a mixture of pentane and ethyl acetate (1:0 to 0:1 by volume), followed by distillation under reduced pressure (150° C., 1 mbar) gave title compound as a colourless oil (3.0 g). ¹H NMR analysis showed that the product existed as a mixture of keto and enol isomers.

¹H NMR (CDCl₃): δ 1.00 (t, J=7.3 Hz), 1.20 (t, J=7.1 Hz), 2.25-2.35 (m), 2.50-2.60 (m), 3.10 (m), 3.75 (t, J=7.7 Hz), 3.80 (s), 4.10-4.15 (m), 4.45 (s), 6.80 (d, J=8.8 Hz), 6.90 (d, J=8.7 Hz), 7.10 (d, J=8.8 Hz), 7.25 (d, J=8.7 Hz)

Preparation 3b

[2-ethyl-8-fluoro-3-(4-methoxybenzyl)-4-oxo-1,4-dihydroquinolin-5-yloxy]acetic acid methyl ester The title compound was prepared by the method of Preparation 1c using (3-amino-4-fluorophenoxy)acetic acid methyl ester and 2-(4-methoxybenzyl)-3-oxopentanoic acid ethyl ester.

MS: ESI (+ve) (Method B): 400 (M+H)⁺, Retention time 2.9 min

Preparation 3c

[4-difluoromethoxy-2-ethyl-8-fluoro-3-(4-methoxybenzyl)quinolin-5-yloxy]acetic acid methyl ester The title compound was prepared by the method of Preparation 1d using [2-ethyl-8-fluoro-3-(4-methoxybenzyl)-4-oxo-1,4-dihydroquinolin-5-yloxy]acetic acid methyl ester and acetic acid chlorodifluoromethyl ester.

MS: ESI (+ve) (Method B): 450 (M+H)⁺, Retention time 4.1 min

Preparation 3d

[4-difluoromethoxy-2-ethyl-8-fluoro-3-(4-methoxybenzyl)quinolin-5-yloxy]acetic acid A solution of [4-difluoromethoxy-2-ethyl-8-fluoro-3-(4-methoxybenzyl)quinolin-5-yloxy]acetic acid methyl ester (0.30 g) in methanol (10 mL), and water (1.0 mL) was treated with 5.0 M aqueous sodium hydroxide solution (0.67 mL) and the resulting mixture was stirred at room temperature for 1 hour. The mixture was acidified by the addition of glacial acetic acid, concentrated under reduced pressure, and the residue purified by preparative reverse-phase HPLC to afford title compound as a pale yellow solid (0.086 g).

¹H NMR (DMSO-d6): 1.10 (t, J=7.4 Hz, 3H), 2.80 (q, J=7.4 Hz, 2H), 3.65 (s, 3H), 4.20 (s, 2H), 4.85 (s, 2H), 6.80 (d, J=8.8 Hz, 2H), 6.95 (m, 3H), 7.20 (t, J=75 Hz, 1H), 7.45 (dd, J=8.9, 10.1 Hz, 1H)

MS: ESI (+ve) (Method A): 436 (M+H)⁺, Retention time 11.2 min

Example 4

[4-difluoromethoxy-3-(4-ethanesulfonylaminobenzyl)-2-ethyl-8-fluoroduinolin-5-yloxy]acetic acid

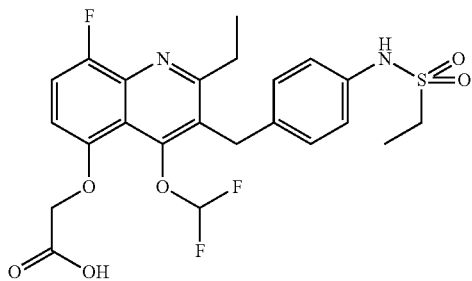 [SMILES: CCc1nc2c(F)ccc(OCC(=O)O)c2c(OC(F)F)c1Cc1ccc(NS(=O)(=O)CC)cc1]

Preparation 4a

[3-(4-tert-butoxycarbonylaminobenzyl)-4-difluoromethoxy-2-ethyl-8-fluoroquinolin-5-yloxy]acetic acid methyl ester A mixture of [3-(4-bromobenzyl)-4-difluoromethoxy-2-ethyl-8-fluoroquinolin-5-yloxy]acetic acid methyl ester (0.40 g), carbamic acid tert-butyl ester (0.19 g), tris(dibenzylideneacetone)dipalladium(0) (0.073 g), Xantphos (0.014 g), cesium carbonate (0.58 g) and 1,4-dioxane (5.0 mL) was heated at 100° C. for 10 hours. The mixture was cooled to room temperature, acidified by the addition of glacial acetic acid and partitioned between ethyl acetate and water. The organic phase was dried over magnesium sulfate and concentrated under reduced pressure. Purification of the residue by column chromatography on silica gel, eluting with a mixture of dichloromethane and ethyl acetate (1:0 to 10:1 by volume) gave title compound as a yellow gum (0.11 g).

MS: ESI (+ve) (Method B): 535 (M+H)$^+$, Retention time 4.3 min

Preparation 4b

[3-(4-aminobenzyl)-4-difluoromethoxy-2-ethyl-8-fluoroquinolin-5-yloxy]acetic acid methyl ester A solution of [3-(4-tert-butoxycarbonylaminobenzyl)-4-difluoromethoxy-2-ethyl-8-fluoroquinolin-5-yloxy]acetic acid methyl ester (0.11 g) in dichloromethane (2.5 mL) was treated with trifluoroacetic acid (0.25 mL) and the resulting mixture was allowed to stand at room temperature for 1 hour. The mixture was diluted with dichloromethane, washed with saturated aqueous sodium hydrogen carbonate solution and dried over magnesium sulfate. The solvent was removed under reduced pressure to afford title compound as a yellow gum (0.051 g).

MS: ESI (+ve) (Method B): 435 (M+H)$^+$, Retention time 2.8 min

Preparation 4c

[4-difluoromethoxy-3-(4-ethanesulfonylaminobenzyl)-2-ethyl-8-fluoroquinolin-5-yloxy]acetic acid methyl ester A mixture of [3-(4-aminobenzyl)-4-difluoromethoxy-2-ethyl-8-fluoroquinolin-5-yloxy]acetic acid methyl ester (0.051 g), pyridine (0.019 mL) and dichloromethane (0.5 mL) at 0° C. was treated with ethanesulfonyl chloride (0.013 mL) and the resulting mixture was stirred at room temperature overnight. The mixture was diluted with dichloromethane and water, and then acidified by the addition of glacial acetic acid. The organic phase was dried over magnesium sulfate, and then concentrated under reduced pressure to afford title compound as a yellow gum (0.051 g).

MS: ESI (+ve) (Method B): 527 (M+H)$^+$, Retention time 3.7 min

Preparation 4d

[4-difluoromethoxy-3-(4-ethanesulfonylaminobenzyl)-2-ethyl-8-fluoroquinolin-5-yloxy]acetic acid A solution of [4-difluoromethoxy-3-(4-ethanesulfonylaminobenzyl)-2-ethyl-8-fluoroquinolin-5-yloxy]acetic acid methyl ester (0.051 g) in methanol (5.0 mL) and water (0.5 mL) was treated with 5.0 M aqueous sodium hydroxide solution (0.25 mL), and the resulting mixture was left to stand at room temperature for 1 hour. The mixture was acidified by the addition of glacial acetic acid, concentrated under reduced pressure, and the residue partitioned between ethyl acetate and water. The organic phase was dried over magnesium sulfate, and then concentrated under reduced pressure. Purification of the residue by column chromatography on silica gel, eluting with a mixture of dichloromethane, methanol and glacial acetic acid (100:1:0.5 to 25:1:0.125 by volume) gave title compound as a cream solid (0.032 g).

$^1$H NMR (DMSO-d6): δ 1.10 (t, J=7.4 Hz, 6H), 2.80 (q, J=7.4 Hz, 2H), 3.00 (q, J=7.4 Hz, 2H), 4.25 (s, 2H), 4.85 (s, 2H), 6.95 (dd, J=3.6, 8.9 Hz, 1H), 7.00 (d, J=8.6 Hz, 2H), 7.05 (d, J=8.6 Hz, 2H), 7.25 (t, J=75 Hz, 1H), 7.50 (dd, J=8.9, 10.1 Hz, 1H), 9.60 (s, 1H)

MS: ESI (+ve) (Method A): 513 (M+H)$^+$, Retention time 9.8 min

MS: ESI (+ve) (Method B): 513 (M+H)$^+$, Retention time 3.4 min

Example 5

[3-(4-acetylbenzyl)-4-difluoromethoxy-2-ethyl-8-fluoroquinolin-5-yloxy]acetic acid

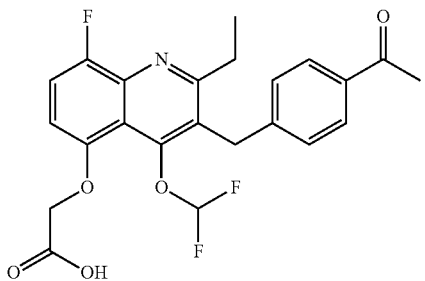 [SMILES: CCc1nc2c(F)ccc(OCC(=O)O)c2c(OC(F)F)c1Cc1ccc(C(C)=O)cc1]

Preparation 5a 2-(4-acetylbenzyl)-3-oxopentanoic acid ethyl ester

The title compound was prepared by the method of Preparation 3a using 2-(4-acetylbenzyl)-3-oxopentanoic acid ethyl ester and 1-(4-bromomethylphenyl)ethanone.

$^1$H NMR (CDCl$_3$): δ 1.00 (t, J=7.2 Hz, 3H), 1.20 (t, J=7.2 Hz, 3H), 2.35 (m, 1H), 2.55 (s, 3H), 2.60 (m, 1H), 3.20 (m, 2H), 3.80 (t, J=7.5 Hz, 1H), 4.15 (m, 2H), 7.25 (d, J=8.5 Hz, 2H), 7.85 (d, J=8.5 Hz, 2H)

Preparation 5b

[3-(4-acetylbenzyl)-2-ethyl-8-fluoro-4-oxo-1,4-dihydroquinolin-5-yloxy]acetic acid methyl ester The title compound was prepared by the method of Preparation 1c using (3-amino-4-fluorophenoxy)acetic acid methyl ester and 2-(4-acetylbenzyl)-3-oxopentanoic acid ethyl ester.

MS: ESI (+ve) (Method B): 412 (M+H)$^+$, Retention time 2.9 min

Preparation 5c

[3-(4-acetylbenzyl)-4-difluoromethoxy-2-ethyl-8-fluoroquinolin-5-yloxy]acetic acid methyl ester The title compound was prepared by the method of Preparation 1d using [3-(4-acetylbenzyl)-2-ethyl-8-fluoro-4-oxo-1,4-dihydroquinolin-5-yloxy]acetic acid methyl ester and acetic acid chlorodifluoromethyl ester.

MS: ESI (+ve) (Method B): 462 (M+H)$^+$, Retention time 4.0 min

Preparation 5d

[3-(4-acetylbenzyl)-4-difluoromethoxy-2-ethyl-8-fluoroquinolin-5-yloxy]acetic acid A solution of [3-(4-acetylbenzyl)-4-difluoromethoxy-2-ethyl-8-fluoroquinolin-5-yloxy]acetic acid methyl ester (0.13 g) in methanol (5.0 mL) was treated with 1.0M aqueous lithium hydroxide solution (0.54 mL), and the resulting mixture was stirred at room temperature for 30 minutes. The mixture was concentrated under reduced pressure, diluted with water and acidified by the addition of 0.1M aqueous hydrochloric acid. The mixture was extracted with ethyl acetate, and the combined extracts were washed with saturated aqueous sodium chloride solution and dried over magnesium sulfate. The solvent was removed under reduced pressure and the residue purified by column chromatography on C-18 column to afford title compound (0.20 g).

$^1$H NMR (CD$_3$OD): δ 1.15 (t, J=7.5 Hz, 3H), 2.50 (s, 3H), 2.85 (q, J=7.5 Hz, 2H), 4.45 (s, 2H), 4.85 (s, 2H), 6.90 (dd, J=37.8.8 Hz, 1H), 7.15 (t, J=75 Hz, 1H), 7.20 (d, J=8.3 Hz, 2H), 7.35 (dd, J=8.8, 10.0 Hz, 1H), 7.90 (d, J=8.3 Hz, 2H)

MS: ESI (+ve) (Method A): 448 (M+H)$^+$, Retention time 10.4 min

MS: ESI (+ve) (Method B): 448 (M+H)$^+$, Retention time 3.7 min

Example 6

{4-difluoromethoxy-2-ethyl-8-fluoro-3-[4-(1-methyl-1H-imidazol-2-yl)benzyl]quinolin-5-yloxy}acetic acid

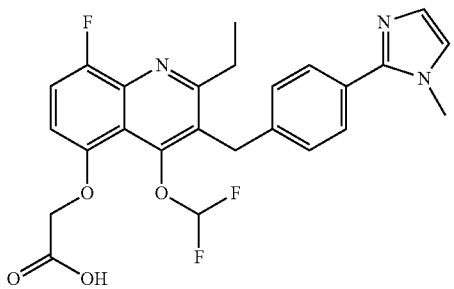 [SMILES: CCc1nc2c(F)ccc(OCC(=O)O)c2c(OC(F)F)c1Cc1ccc(-c2nccn2C)cc1]

Preparation 6a

{4-difluoromethoxy-2-ethyl-8-fluoro-3-[4-(1-methyl-1H-imidazol-2-yl)benzyl]quinolin-5-yloxy}acetic acid methyl ester A mixture of [3-(4-bromobenzyl)-4-difluoromethoxy-2-ethyl-8-fluoroquinolin-5-yloxy]acetic acid methyl ester (0.22 g), 1-methyl-2-tributylstannanyl-1H-imidazole (0.50 g), tetrakis(triphenylphosphine)palladium(0) (0.055 g) and 1,4-dioxane (4.4 mL) was heated at 100° C. for 1 hour. The mixture was cooled to room temperature and used in the next step.

MS: ESI (+ve) (Method B): 500 (M+H)$^+$, Retention time 2.5 min

Preparation 6b

{4-difluoromethoxy-2-ethyl-8-fluoro-3-[4-(1-methyl-1H-imidazol-2-yl)benzyl]quinolin-5-yloxy}acetic acid The reaction mixture of Preparation 6a was treated with methanol (0.25 mL), water (1.0 mL) and 5.0 M aqueous lithium hydroxide solution (0.25 mL), and the resulting mixture was stirred at room temperature for 30 min. The mixture was diluted with water, acidified by the addition of glacial acetic acid and then concentrated to low bulk under reduced pressure. The residue was extracted with ethyl acetate, and the combined extracts were dried over magnesium sulfate. Purification of the residue by column chromatography on silica gel, eluting with a mixture of dichloromethane, methanol and glacial acetic acid (1:0:0 to 2:1:0.01 by volume), followed by preparative reverse-phase HPLC gave title compound as a white solid (0.025 g).

$^1$H NMR (CD$_3$OD): δ 120 (t, J=7.6 Hz, 3H), 2.90 (q, J=7.6 Hz, 2H), 3.70 (s, 3H), 4.45 (s, 2H), 4.65 (s, 2H), 6.85 (dd, J=3.7, 8.8 Hz, 1H), 7.10 (d, J=1.2 Hz, 1H), 7.25 (d, J=8.3 Hz, 2H), 7.30-7.50 (m, 3H), 7.35 (t, J=75 Hz, 1H), 8.10 (s, 1H)

MS: ESI (+ve) (Method A): 486 (M+H)$^+$, Retention time 6.7 min

Example 7

[8-chloro-4-difluoromethoxy-2-ethyl-3-(4-pyrazol-1-ylbenzyl) quinolin-5-yloxy]acetic acid

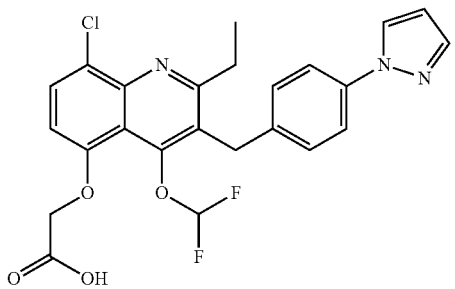 [SMILES: CCc1nc2c(Cl)ccc(OCC(=O)O)c2c(OC(F)F)c1Cc1ccc(-n2cccn2)cc1]

Preparation 7a (4-chloro-3-nitrophenoxy)acetic acid methyl ester

A mixture of 4-chloro-3-nitrophenol (25 g), N,N-dimethylformamide (200 mL), potassium carbonate (60 g) and bromoacetic acid methyl ester (15.5 mL) was stirred at room temperature for 2.5 hours. The mixture was partitioned between ethyl acetate and water, and the aqueous phase extracted with ethyl acetate. The combined extracts were dried over sodium sulfate and then concentrated under reduced pressure. The residue was washed with diethyl ether to afford title compound as a white solid (30 g).

$^1$H NMR (CDCl$_3$): δ 3.85 (s, 3H), 4.70 (s, 2H), 7.10 (dd, J=3.0, 8.9 Hz, 1H), 7.40 (dd,

Preparation 7b (3-amino-4-chlorophenoxy)acetic acid methyl ester

A solution of (4-chloro-3-nitrophenoxy)acetic acid methyl ester (30 g) in methanol (100 mL) was added to a mixture of iron (26 g), ammonium chloride (33 g) and water (400 mL) at room temperature, and the resulting mixture was heated in an ultrasonic bath at 60° C. for 4 hours. The mixture was basified by the addition of sodium hydroxide, extracted with ethyl acetate, and the combined extracts were washed with 1.0M aqueous hydrochloric acid solution. The pH of the combined aqueous phases was adjusted to 7-8 by the addition of sodium hydroxide, and the resulting precipitate was collected by filtration and then dried to afford title compound (14 g).

$^1$H NMR (DMSO-d6): δ 3.70 (s, 3H), 4.60 (s, 2H), 5.35 (br s, 2H), 6.10 (dd, J=3.0,

Preparation 7c

[8-chloro-2-ethyl-4-oxo-3-(4-pyrazol-1-ylbenzyl)-1, 4-dihydroquinolin-5-yloxy]acetic acid methyl ester The title compound was prepared by the method of Preparation 1c using (3-amino-4-chlorophenoxy)acetic acid methyl ester and 3-oxo-2-(4-pyrazol-1-ylbenzyl)pentanoic acid ethyl ester.

MS: ESI (+ve) (Method B): 452 (M+H)+, Retention time 3.2 min

Preparation 7d

[8-chloro-4-difluoromethoxy-2-ethyl-3-(4-pyrazol-1-ylbenzyl)quinolin-5-yloxy]acetic acid methyl ester The title compound was prepared by the method of Preparation 1d using [8-chloro-2-ethyl-4-oxo-3-(4-pyrazol-1-ylbenzyl)-1,4-dihydroquinolin-5-yloxy]acetic acid methyl ester and acetic acid chlorodifluoromethyl ester.

MS: ESI (+ve) (Method B): 502 (M+H)+, Retention time 4.3 min

Preparation 7e

[8-chloro-4-difluoromethoxy-2-ethyl-3-(4-pyrazol-1-ylbenzyl)quinolin-5-yloxy]acetic acid A solution of [8-chloro-4-difluoromethoxy-2-ethyl-3-(4-pyrazol-1-ylbenzyl)quinolin-5-yloxy]acetic acid methyl ester (0.56 g) in tetrahydrofuran (20 mL) was treated with 1.0M aqueous lithium hydroxide solution (2.4 mL), and the resulting mixture was stirred at room temperature for 30 minutes. The mixture was diluted with 0.1M aqueous hydrochloric acid solution, concentrated under reduced pressure and then extracted with ethyl acetate. The combined extracts were washed with saturated aqueous sodium chloride solution, dried over magnesium sulfate and then concentrated under reduced pressure. The residue was purified by trituration with a mixture of methanol and water, followed by column chromatography on C-18 column to afford title compound (0.35 g).

1H NMR (DMSO-d6): δ 1.15 (t, J=7.3 Hz, 3H), 2.85 (q, J=7.3 Hz, 2H), 4.35 (s, 2H), 4.90 (s, 2H), 6.45 (dd, J=1.7, 2.5 Hz, 1H), 7.00 (d, J=8.8 Hz, 1H), 7.15 (d, J=8.6 Hz, 2H), 7.20 (t, J=75 Hz, 1H), 7.65 (d, J=1.9 Hz, 1H), 7.70 (d, J=8.6 Hz, 2H), 7.80 (d, J=8.8 Hz, 1H), 8.35 (d, J=1.9 Hz, 1H)

MS: ESI (+ve) (Method A): 488 (M+H)+, Retention time 12.2 min

MS: ESI (+ve) (Method B): 488 (M+H)+, Retention time 4.0 min

Example 8

[4-difluoromethoxy-2-ethyl-8-fluoro-3-(4-thiazol-2-ylbenzyl)quinolin-5-yloxy]acetic acid

Preparation 8a

{4-difluoromethoxy-2-ethyl-8-fluoro-3-[4-(4,4,5,5-tetramethyl-[1,3,2]dioxaborolan-2-yl)benzyl]quinolin-5-yloxy}acetic acid methyl ester A mixture of [3-(4-bromobenzyl)-4-difluoromethoxy-2-ethyl-8-fluoroquinolin-5-yloxy]acetic acid methyl ester (0.39 g), 4,4,5,5,4',4',5',5'-octamethyl[2,2']bi[[1,3,2]dioxaborolanyl] (0.24 g), [1,1'-bis(diphenylphosphino)ferrocene]dichloropalladium (0.060 g), potassium acetate (0.23 g) and 1,4-dioxane (4.4 mL) was heated at 100° C. for 18 hours. The mixture was cooled to room temperature, diluted with ethyl acetate and dichloromethane, and then filtered. The filtrate was concentrated under reduced pressure, and the residue purified by column chromatography on silica gel, eluting with a mixture of cyclohexane and ethyl acetate to afford title compound (0.24 g).

MS: ESI (+ve) (Method B): 546 (M+H)+, Retention time 4.6 min

Preparation 8b

[4-difluoromethoxy-2-ethyl-8-fluoro-3-(4-thiazol-2-ylbenzyl)quinolin-5-yloxy]acetic acid A mixture of {4-difluoromethoxy-2-ethyl-8-fluoro-3-[4-(4,4,5,5-tetramethyl-[1,3,2]dioxaborolan-2-yl)benzyl]quinolin-5-yloxy}acetic acid methyl ester (0.052 g), 2-bromothiazole (0.076 g), [1,1'-bis(diphenylphosphino)ferrocene]dichloropalladium (0.060 g), 1,4-dioxane (2.0 mL) and 2.0M aqueous cesium carbonate solution (0.19 mL) was heated at 90° C. overnight. The mixture was cooled to room temperature, diluted with ethyl acetate and filtered. The filtrate was concentrated under reduced pressure, and the residue dissolved in tetrahydrofuran (5.0 mL) and 1.0M aqueous lithium hydroxide solution (0.19 mL), and the resulting mixture was stirred at room temperature for 1 hour. The mixture was concentrate to low bulk under reduced pressure, and the residue acidified by the addition 0.1M aqueous hydrochloric acid solution and then extracted with ethyl acetate. The combined extracts were dried over magnesium sulfate and then concentrated under reduced pressure. Purification of the residue by column chromatography on C-18 column gave title compound (0.020 g).

1H NMR (CD3OD): δ 1.15 (t, J=7.5 Hz, 3H), 2.90 (q, J=7.5 Hz, 2H), 4.45 (s, 2H), 4.85 (s, 2H), 6.90 (dd. J=3.5, 8.8 Hz, 1H), 7.15 (t, J=75 Hz, 1H), 7.20 (d, J=8.3 Hz, 2H), 7.35 (dd, J=9.0, 10.0 Hz, 1H), 7.50 (d, J=3.5 Hz, 1H), 7.80 (d, J=3.5 Hz, 1H), 7.85 (d, J=8.3 Hz, 2H)

MS: ESI (+ve) (Method A): 489 (M+H)+, Retention time 11.4 min

MS: ESI (+ve) (Method B): 489 (M+H)+, Retention time 3.8 min

Example 9

[4-difluoromethoxy-2-ethyl-8-fluoro-3-(4-pyrimidin-2-ylbenzyl)quinolin-5-yloxy]acetic acid

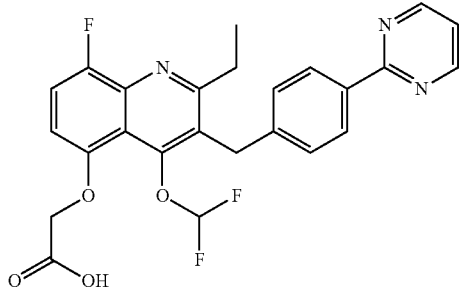 [SMILES: CCc1nc2c(F)ccc(OCC(=O)O)c2c(OC(F)F)c1Cc1ccc(-c2ncccn2)cc1]

Preparation 9a

[4-difluoromethoxy-2-ethyl-8-fluoro-3-(4-pyrimidin-2-yl-benzyl)quinolin-5-yloxy]acetic acid A mixture of {4-difluoromethoxy-2-ethyl-8-fluoro-3-[4-(4,4,5,5-tetramethyl-[1,3,2]dioxaborolan-2-yl)benzyl]quinolin-5-yloxy}acetic acid methyl ester (0.10 g), 2-bromopyrimidine (0.076 g), [1,1-bis(diphenylphosphino)ferrocene]dichloropalladium (0.016 g), 1,4-dioxane (2.0 mL) and 2.0M aqueous cesium carbonate solution (0.38 mL) was heated by microwave irradiation at 90 to 130° C. for 1 hour. The mixture was cooled to room temperature, diluted with ethyl acetate and then filtered. The filtrate was concentrated under reduced pressure and the residue dissolved in tetrahydrofuran (5.0 mL) and 1.0M aqueous lithium hydroxide solution (0.38 mL), and the resulting mixture was stirred at room temperature for 1 hour. The mixture was acidified by the addition of 0.1M aqueous hydrochloric acid solution and then concentrated under reduced pressure. Purification of the residue by preparative reverse-phase HPLC gave title compound (0.021 g).

$^1$H NMR (CD$_3$OD): δ 1.15 (t, J=7.5 Hz, 3H), 2.90 (q, J=7.5 Hz, 2H), 4.45 (s, 2H), 4.90 (s, 2H), 6.90 (dd, J=3.6, 8.8 Hz, 1H), 7.15 (t, J=75 Hz, 1H), 7.20 (d, J=8.3 Hz, 2H), 7.30 (t, J=4.8 Hz, 1H), 7.35 (m, 1H), 8.25 (d, J=8.3 Hz, 2H), 8.75 (d. J=4.8 Hz, 2H)

MS: ESI (+ve) (Method A): 484 (M+H)$^+$, Retention time 10.9 min

MS: ESI (+ve) (Method A): 484 (M+H)$^+$, Retention time 3.7 min

Example 10

{8-chloro-4-difluoromethoxy-3-[4-(2,2-dimethylpropionyl)benzyl]-2-ethylquinolin-5-yloxy}acetic acid

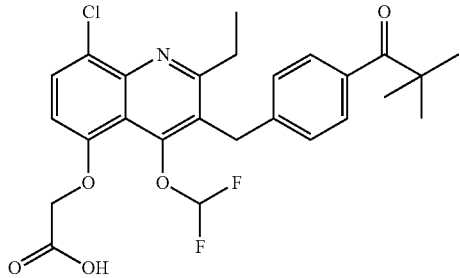 [SMILES: CCc1nc2c(Cl)ccc(OCC(=O)O)c2c(OC(F)F)c1Cc1ccc(C(=O)C(C)(C)C)cc1]

Preparation 10a

2-[4-(2,2-dimethylpropionyl)benzyl]-3-oxopentanoic acid ethyl ester

The title compound was prepared by the method of Preparation 3a using 3-oxo-pentanoic acid ethyl ester and 1-(4-bromomethylphenyl)-2,2-dimethylpropan-1-one.

Preparation 10b

{8-chloro-3-[4-(2,2-dimethylpropionyl)benzyl]-2-ethyl-4-oxo-1,4-dihydroquinolin-5-yloxy}acetic acid methyl ester The title compound was prepared by the method of Preparation 1c using (3-amino-4-chlorophenoxy)acetic acid methyl ester and 2-[4-(2,2-dimethylpropionyl)benzyl]-3-oxopentanoic acid ethyl ester.

MS: ESI (+ve) (Method B): 470 (M+H)$^+$, Retention time 3.8 min

Preparation 10c

{8-chloro-4-difluoromethoxy-3-[4-(2,2-dimethylpropionyl)benzyl]-2-ethylquinolin-5-yloxy}acetic acid methyl ester A mixture of {8-chloro-3-[4-(2,2-dimethylpropionyl)benzyl]-2-ethyl-4-oxo-1,4-dihydroquinolin-5-yloxy}acetic acid methyl ester (0.14 g), N,N-dimethylformamide (5.0 mL) and potassium carbonate (0.13 g) was stirred at 40° C. for 5 hours under an atmosphere of chlorodifluoromethane. The mixture was diluted with water, extracted with ethyl acetate, and the combined extracts washed saturated aqueous sodium chloride solution and then dried over magnesium sulfate. The solvent was removed under reduced pressure and the residue purified by column chromatography on silica gel, eluting with a mixture of cyclohexane and ethyl acetate (7:3 by volume) to afford title compound (0.071 g).

MS: ESI (+ve) (Method B): 520 (M+H)$^+$, Retention time 4.7 min

Preparation 10d

{8-chloro-4-difluoromethoxy-3-[4-(2,2-dimethylpropionyl)benzyl]-2-ethylquinolin-5-yloxy}acetic acid A solution of {8-chloro-4-difluoromethoxy-3-[4-(2,2-dimethylpropionyl)benzyl]-2-ethylquinolin-5-yloxy}acetic acid methyl ester (0.071 g) in tetrahydrofuran (5.0 mL) was treated with 1.0M aqueous lithium hydroxide solution (0.28 mL), and the resulting mixture was stirred at room temperature for 1 hour. The mixture was concentrated to low bulk under reduced pressure, acidified by the addition of 0.1M aqueous hydrochloric acid solution and extracted with ethyl acetate. The combined extracts were dried over magnesium sulfate and then concentrated under reduced pressure. Purification of the residue by preparative reverse-phase HPLC gave title compound as a yellow solid (0.040 g).

$^1$H NMR (CD$_3$OD): δ 1.25 (t, J=7.4 Hz, 3H), 1.30 (s, 9H), 2.85 (q, J=7.4 Hz, 2H), 4.40 (s, 2H), 4.90 (s, 2H), 6.95 (d, J=8.9 Hz, 1H), 7.10 (t, J=75 Hz, 1H), 7.15 (d, J=8.3 Hz, 2H), 7.60 (d, J=8.3 Hz, 2H), 7.75 (d, J=8.7 Hz, 1H)

MS: ESI (+ve) (Method A): 506 (M+H)$^+$, Retention time 13.6 min

Example 11

[8-chloro-2-methoxy-4-methyl-3-(4-pyrazol-1-yl-benzyl)quinolin-5-yloxy]acetic acid

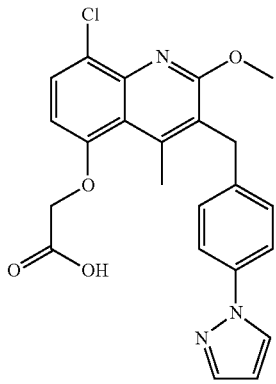 [SMILES: COc1nc2c(Cl)ccc(OCC(=O)O)c2c(C)c1Cc1ccc(-n2cccn2)cc1]

Preparation 11a 3-oxo-2-(4-pyrazol-1-ylbenzyl)thiobutyric acid S-tert-butyl ester A solution of 3-oxothiobutyric acid S-tert-butyl ester (3.7 g) in 1,2-dimethoxyethane (5.0 mL) was added to a stirred suspension of sodium hydride (60% in oil, 0.92 g) in 1,2-dimethoxyethane (25 mL) at −10° C., and the resulting mixture was warmed to 15° C. over 15 minutes, cooled to −10° C. and then treated dropwise with a mixture of 1-(4-bromomethylphenyl)-1H-pyrazole (5.0 g) in 1,2-dimethoxyethane (20 mL) over a period of 30 minutes. The resulting mixture was warmed to room temperature and then stirred at this temperature for overnight. The mixture was diluted water, pH adjusted to 5 by the addition of glacial acetic acid and then saturated with sodium chloride. The mixture was extracted ethyl acetate and the combined extracts were dried over magnesium sulfate and then concentrated under reduced pressure. Purification of the residue purified by column chromatography on silica gel, eluting with a mixture of pentane, dichloromethane and ethyl acetate (1:3:0, 0:1:0 to 0:10:1 by volume) gave title compound as a colourless gum (0.6 g).

$^1$H NMR (CDCl$_3$): δ 1.40 (s, 9H), 2.20 (s, 3H), 3.15 (m, 2H), 3.90 (t, J=7.5 Hz, 1H), 6.45 (m, 1H), 7.25 (d, J=8.5 Hz, 2H), 7.60 (d, J=8.5 Hz, 2H), 7.70 (m, 1H), 7.90 (m, 1H).

Preparation 11b

N-(2-chloro-5-hydroxyphenyl)-3-oxo-2-(4-pyrazol-1-ylbenzyl)butyramide

Silver trifluoroacetate (1.5 g) was added, over a period of 1 hour, to a stirred solution of 3-amino-4-chlorophenol (0.67 g) and 3-oxo-2-(4-pyrazol-1-ylbenzyl)thiobutyric acid S-tert-butyl ester (1.7 g) in 1,2-dimethoxyethane (10 mL) at room temperature, and the resulting mixture was stirred at room temperature for 4 hours. The mixture was concentrated under reduced pressure and the residue purified by column chromatography on silica gel, eluting with a mixture of dichloromethane and ethyl acetate (1:0 to 3:1 by volume) to afford title compound as a brown solid (1.1 g).

MS: ESI (+ve) (Method B): 384 (M+H)$^+$, Retention time 3.1 min

Preparation 11c 8-chloro-5-hydroxy-4-methyl-3-(4-pyrazol-1-ylbenzyl)-1H-quinolin-2-one A mixture of N-(2-chloro-5-hydroxyphenyl)-3-oxo-2-(4-pyrazol-1-ylbenzyl)butyramide (1.3 g) and methanesulfonic acid (7.0 mL) was heated at 100° C. for 10 minutes. The mixture was cooled to room temperature and then poured into a saturated aqueous solution of sodium acetate. The resulting precipitate was collected by filtration, washed with water and dried to afford title compound as a beige solid (0.81 g).

$^1$H NMR (DMSO-d6): δ 2.65 (s, 3H), 4.05 (s, 2H), 6.50 (dd, J=1.8, 2.5 Hz, 1H), 6.65 (d, J=8.7 Hz, 2H), 7.30 (d, J=8.7 Hz, 2H), 7.40 (d, J=8.7 Hz, 1H), 7.65-7.75 (m, 3H), 8.40 (dd, J=0.5, 2.5 Hz, 1H), 10.30 (br s, 1H)

Preparation 11d

[8-chloro-4-methyl-2-oxo-3-(4-pyrazol-1-ylbenzyl)-1,2-dihydroquinolin-5-yloxy]acetic acid methyl ester The title compound was prepared by the method of Preparation 7a using 8-chloro-5-hydroxy-4-methyl-3-(4-pyrazol-1-ylbenzyl)-1H-quinolin-2-one and bromoacetic acid methyl ester.

MS: ESI (+ve) (Method B): 438 (M+H)$^+$, Retention time 3.5 min

Preparation 11e

[8-chloro-2-methoxy-4-methyl-3-(4-pyrazol-1-yl-benzyl)quinolin-5-yloxy]acetic acid methyl ester A mixture of [8-chloro-4-methyl-2-oxo-3-(4-pyrazol-1-ylbenzyl)-1,2-dihydroquinolin-5-yloxy]acetic acid methyl ester (0.35 g), potassium carbonate (0.33 g), iodomethane (0.50 mL) and N,N-dimethylformamide (5.0 mL) was stirred at room temperature for 16 hours. The mixture was diluted with water, acidified by the addition of glacial acetic acid and extracted with ethyl acetate. The combined extracts were washed with saturated aqueous sodium chloride solution, dried over magnesium sulfate and concentrated under reduced pressure to afford title compound as a cream solid (0.37 g).

MS: ESI (+ve) (Method B): 452 (M+H)$^+$, Retention time 4.5 min

Preparation 11f

[8-chloro-2-methoxy-4-methyl-3-(4-pyrazol-1-yl-benzyl)quinolin-5-yloxy]acetic acid A solution of [8-chloro-2-methoxy-4-methyl-3-(4-pyrazol-1-yl-benzyl)quinolin-5-yloxy]acetic acid methyl ester (0.37 g) in methanol (7.0 mL) and water (0.7 mL) was treated with 5.0M aqueous sodium hydroxide solution (0.32 mL), and the resulting mixture was stirred at room temperature for 2 hours. The mixture was acidified by the addition of glacial acetic acid, diluted with water and extracted with ethyl acetate. The combined extracts were dried over magnesium sulfate and then concentrated under reduced pressure. The residue was crystallised from methanol to give title compound as a white solid (0.18 g).

$^1$H NMR (DMSO-d6): δ 2.75 (s, 3H), 4.00 (s, 3H), 4.15 (s, 2H), 4.75 (s, 2H), 6.45 (m, 1H), 6.80 (d, J=8.7 Hz, 1H), 7.15 (d, J=8.6 Hz, 2H), 7.60-7.65 (m, 4H), 8.35 (d, J=2.4 Hz, 1H)

MS: ESI (+ve) (Method A): 438 (M+H)+, Retention time 12.5 min
MS: ESI (+ve) (Method B): 438 (M+H)+, Retention time 4.1 min Example 12

[2-difluoromethoxy-8-fluoro-4-methyl-3-(4-pyrazol-1-ylbenzyl)quinolin-5-yloxy]acetic acid

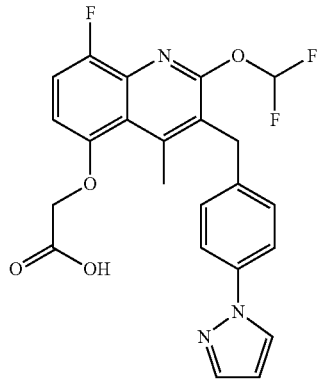

Preparation 12a

N-(2-fluoro-5-hydroxyphenyl)-3-oxo-2-(4-pyrazol-1-ylbenzyl)butyramide

The title compound was prepared by the method of Preparation 11b using 3-oxo-2-(4-pyrazol-1-ylbenzyl)thiobutyric acid S-tert-butyl ester and 3-amino-4-fluorophenol.
MS: ESI (+ve) (Method B): 368 (M+H)+, Retention time 2.9 min Preparation 12b 8-fluoro-5-hydroxy-4-methyl-3-(4-pyrazol-1-ylbenzyl)-1H-quinolin-2-one The title compound was prepared by the method of Preparation 11c using N-(2-fluoro-5-hydroxyphenyl)-3-oxo-2-(4-pyrazol-1-ylbenzyl)butyramide.
$^1$H NMR (DMSO-d6): δ 2.65 (s, 3H), 4.05 (s, 2H), 6.50-6.55 (m, 2H), 7.15 (dd, J=8.9, 10.2 Hz, 1H), 7.30 (d, J=8.6 Hz, 2H), 7.70 (m, 3H), 8.40 (dd. J=0.4, 2.5 Hz, 1H), 10.10 (s, 1H), 11.40 (s, 1H)

Preparation 12c

[8-fluoro-4-methyl-2-oxo-3-(4-pyrazol-1-ylbenzyl)-1,2-dihydroquinolin-5-yloxy]acetic acid methyl ester The title compound was prepared by the method of Preparation 7a using 8-fluoro-5-hydroxy-4-methyl-3-(4-pyrazol-1-ylbenzyl)-1H-quinolin-2-one and bromoacetic acid methyl ester.
MS: ESI (+ve) (Method B): 422 (M+H)+, Retention time 3.3 min Preparation 12d

[2-difluoromethoxy-8-fluoro-4-methyl-3-(4-pyrazol-1-ylbenzyl)quinolin-5-yloxy]acetic acid methyl ester The title compound was prepared by the method of Preparation 10c using [8-fluoro-4-methyl-2-oxo-3-(4-pyrazol-1-ylbenzyl)-1,2-dihydroquinolin-5-yloxy]acetic acid methyl ester and chlorodifluoromethane.
MS: ESI (+ve) (Method 13): 472 (M+H)+, Retention time 4.2 min Preparation 12e

[2-difluoromethoxy-8-fluoro-4-methyl-3-(4-pyrazol-1-ylbenzyl)quinolin-5-yloxy]acetic acid A solution of [2-difluoromethoxy-8-fluoro-4-methyl-3-(4-pyrazol-1-ylbenzyl)quinolin-5-yloxy]acetic acid methyl ester (0.43 g) in methanol (7.0 mL) and water (0.7 mL) was treated with 5.0M aqueous sodium hydroxide solution (0.36 mL), and the resulting mixture was stirred at room temperature for 1.5 hours. The mixture was acidified by the addition of glacial acetic acid, diluted with water and then extracted with ethyl acetate. The combined extracts were dried over magnesium sulfate and then concentrated under reduced pressure. Purification of the residue by column chromatography on silica gel gave title compound as a white solid (0.034 g).
$^1$H NMR (DMSO-d6): δ 2.85 (s, 3H), 4.20 (s, 2H), 4.80 (s, 2H), 6.45 (t, J=2.0 Hz, 1H), 6.90 (dd, J=4.0, 8.9 Hz, 1H), 7.20 (d, J=8.6 Hz, 2H), 7.45 (dd, J=8.9, 9.7 Hz, 1H), 7.65 (d, J=2.0 Hz, 1H), 7.70 (d, J=8.6 Hz, 2H), 7.85 (t, J=72 Hz, 1H), 8.35 (d, J=2.7 Hz, 1H)
MS: ESI (+ve) (Method A): 458 (M+H)+, Retention time 11.5 min
MS: ESI (+ve) (Method B): 458 (M+H)+, Retention time 3.8 min Example 13

[8-chloro-2-difluoromethoxy-4-methyl-3-(4-pyrazol-1-ylbenzyl)quinolin-5-yloxy]acetic acid

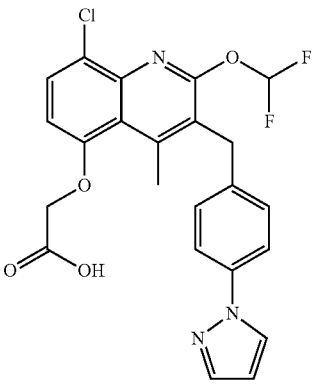 [SMILES: Cc1c(Cc2ccc(-n3cccn3)cc2)c(OC(F)F)nc2c(Cl)ccc(OCC(=O)O)c12]

Preparation 13a

[8-chloro-2-difluoromethoxy-4-methyl-3-(4-pyrazol-1-ylbenzyl)quinolin-5-yloxy]acetic acid methyl ester The title compound was prepared by the method of Preparation 10c using [8-chloro-4-methyl-2-oxo-3-(4-pyrazol-1- ylbenzyl)-1,2-dihydroquinolin-5-yloxy]acetic acid methyl ester and chlorodifluoromethane.

MS: ESI (+ve) (Method B): 488 (M+H)⁺, Retention time 4.4 min

Preparation 13b

[8-chloro-2-difluoromethoxy-4-methyl-3-(4-pyrazol-1-ylbenzyl)quinolin-5-yloxy]acetic acid A solution of [8-chloro-2-difluoromethoxy-4-methyl-3-(4-pyrazol-1-ylbenzyl)quinolin-5-yloxy]acetic acid methyl ester (0.38 g) in methanol (7.0 mL) and water (0.7 mL) was treated with 5.0M aqueous sodium hydroxide solution (0.32 mL), and the resulting mixture was stirred at room temperature for 3 hours. The mixture was acidified by the addition of glacial acetic acid, diluted with water and extracted with ethyl acetate. The combined extracts were dried over magnesium sulfate and then concentrated under reduced pressure. The residue was purified by trituration with methanol, followed by column chromatography on silica gel to afford title compound as a white solid (0.036 g).

¹H NMR (DMSO-d6): δ 2.85 (s, 3H), 4.20 (s, 2H), 4.80 (s, 2H), 6.45 (dd. J=1.7, 2.5 Hz, 1H), 6.95 (d, J=8.6 Hz, 1H), 7.20 (d, J=8.6 Hz, 2H), 7.65 (d, J=1.7 Hz, 1H), 7.70 (d, J=8.6 Hz, 2H), 7.75 (d, J=8.6 Hz, 1H), 7.85 (t, J=73 Hz, 1H), 8.35 (d, J=2.6 Hz, 1H)

MS: ESI (+ve) (Method A): 474 (M+H)⁺, Retention time 12.2 min

MS: ESI (+ve) (Method B): 474 (M+H)⁺, Retention time 4.0 min

Example 14

[8-chloro-4-difluoromethoxy-2-ethyl-3-(4-isobutyrylbenzyl) quinolin-5-yloxy]acetic acid

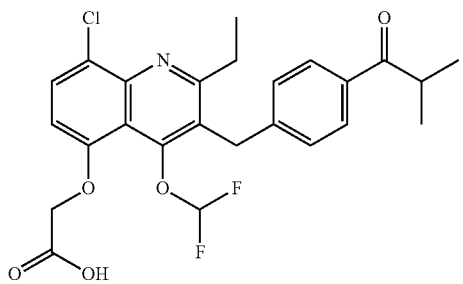 [SMILES: CCc1nc2c(Cl)ccc(OCC(=O)O)c2c(OC(F)F)c1Cc1ccc(C(=O)C(C)C)cc1]

Preparation 14a 2-(4-isobutyrylbenzyl)-3-oxopentanoic acid ethyl ester

The title compound was prepared by the method of Preparation 3a using 3-oxopentanoic acid ethyl ester and 1-(4-bromomethylphenyl)-2-methylpropan-1-one.

MS: ESI (+ve) (Method B): 305 (M−1-H)⁺, Retention time 3.8 min

Preparation 14b

[8-chloro-2-ethyl-3-(4-isobutyrylbenzyl)-4-oxo-1,4-dihydroquinolin-5-yloxy]acetic acid methyl ester The title compound was prepared by the method of Preparation 1c using (3-amino-4-chlorophenoxy)acetic acid methyl ester and 2-(4-isobutyrylbenzyl)-3-oxopentanoic acid ethyl ester.

MS: ESI (+ve) (Method B): 456 (M+H)⁺, Retention time 3.6 min

Preparation 14c

[8-chloro-4-difluoromethoxy-2-ethyl-3-(4-isobutyrylbenzyl)quinolin-5-yloxy]acetic acid methyl ester The title compound was prepared by the method of Preparation 10c using [8-chloro-2-ethyl-3-(4-isobutyrylbenzyl)-4-oxo-1,4-dihydroquinolin-5-yloxy]acetic acid methyl ester and chlorodifluoromethane.

MS: ESI (+ve) (Method B): 506 (M+H)⁺, Retention time 4.6 min

Preparation 14d

[8-chloro-4-difluoromethoxy-2-ethyl-3-(4-isobutylbenzyl)quinolin-5-yloxy]acetic acid A solution of [8-chloro-4-difluoromethoxy-2-ethyl-3-(4-isobutyrylbenzyl)quinolin-5-yloxy]acetic acid methyl ester (0.22 g) in tetrahydrofuran (5.0 mL) and water (1.0 mL) was treated with 1.0M aqueous lithium hydroxide solution (0.86 mL), and the resulting mixture was stirred at room temperature for 2 hours. The mixture was concentrated to low bulk under reduced pressure, and the pH adjusted to 4-5 by the addition of 1.0M aqueous hydrochloric acid solution. The mixture was extracted with ethyl acetate, and the combined extracts were dried over magnesium sulfate and then concentrated under reduced pressure. Purification of the residue by preparative reverse-phase HPLC gave title compound (0.18 g).

¹H NMR (CDCl₃): δ 1.15 (d, J=6.9 Hz, 6H), 1.30 (t, J=7.4 Hz, 3H), 2.85 (q, J=7.4 Hz, 2H), 3.45 (m, 1H), 4.40 (s, 2H), 4.85 (s, 2H), 6.10 (d, J=8.3 Hz, 1H), 6.80 (t, J=75 Hz, 1H), 7.15 (d, J=8.4 Hz, 2H), 7.70 (d, J=8.3 Hz, 1H), 7.80 (d, J=8.3 Hz, 2H)

MS: ESI (+ve) (Method A): 492 (M+H)⁺, Retention time 13.1 min

Example 15

[8-fluoro-2-methoxy-4-methyl-3-(4-pyrazol-1-yl-benzyl)quinolin-5-yloxy]acetic acid

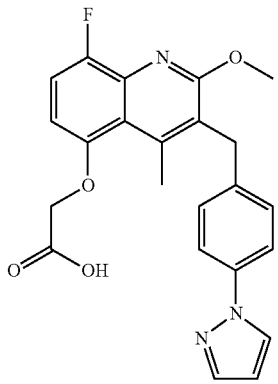 [SMILES: COc1nc2c(F)ccc(OCC(=O)O)c2c(C)c1Cc1ccc(-n2cccn2)cc1]

Preparation 15a

[8-fluoro-2-methoxy-4-methyl-3-(4-pyrazol-1-ylbenzyl)quinolin-5-yloxy]acetic acid methyl ester The title compound was prepared by the method of Preparation 11e using [8-fluoro-4-methyl-2-oxo-3-(4-pyrazol-1-ylbenzyl)-1,2-dihydroquinolin-5-yloxy]acetic acid methyl ester and iodomethane.

Preparation 15b

[8-fluoro-2-methoxy-4-methyl-3-(4-pyrazol-1-yl-benzyl)quinolin-5-yloxy]acetic acid The title compound was prepared by the method of Preparation 13b using [8-fluoro-2-methoxy-4-methyl-3-(4-pyrazol-1-ylbenzyl)quinolin-5-yloxy]acetic acid methyl ester.

$^1$H NMR (DMSO-d6): δ 2.80 (s, 3H), 3.95 (s, 3H), 4.20 (s, 2H), 4.75 (s, 2H), 6.45 (m, 1H), 6.75 (dd, J=4.0, 8.9 Hz, 1H), 7.20 (d, J=85 Hz, 2H), 7.30 (dd, J=8.9, 9.8 Hz, 1H), 7.65 (m, 3H), 8.35 (d, J=2.5 Hz, 1H)

MS: ESI (+ve) (Method A): 422 (M+H)$^+$, Retention time 11.3 min

Example 16

[4-difluoromethoxy-2-ethyl-8-fluoro-3-(4-trifluoromethoxybenzyl)quinolin-5-yloxy]acetic acid

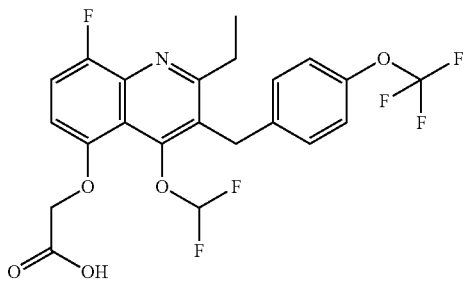 [SMILES: CCc1nc2c(F)ccc(OCC(=O)O)c2c(OC(F)F)c1Cc1ccc(OC(F)(F)F)cc1]

Preparation 16a 3-oxo-2-(4-trifluoromethoxybenzyl)pentanoic acid ethyl ester The title compound was prepared by the method of Preparation 3a using 3-oxopentanoic acid ethyl ester and 1-bromomethyl-4-trifluoromethoxybenzene.

$^1$H NMR (CDCl$_3$): δ 1.00 (t, J=7.3 Hz, 3H), 1.20 (t, J=7.1 Hz, 3H), 2.30-2.40 (m, 1H), 2.55-2.65 (m, 1H), 3.15 (m, 2H), 3.75 (t, J=7.6 Hz, 1H), 4.15 (q, J=7.1 Hz,

Preparation 16b

[2-ethyl-8-fluoro-4-oxo-3-(4-trifluoromethoxybenzyl)-1,4-dihydroquinolin-5-yloxy]acetic acid methyl ester The title compound was prepared by the method of Preparation 1c using (3-amino-4-chlorophenoxy)acetic acid methyl ester and 3-oxo-2-(4-trifluoromethoxybenzyl) pentanoic acid ethyl ester.

MS: ESI (+ve) (Method B): 454 (M+H)$^+$, Retention time 3.5 min

Preparation 16c

[4-difluoromethoxy-2-ethyl-8-fluoro-3-(4-trifluoromethoxybenzyl)quinolin-5-yloxy]acetic acid methyl ester The title compound was prepared by the method of Preparation 10c using [2-ethyl-8-fluoro-4-oxo-3-(4-trifluoromethoxybenzyl)-1,4-dihydroquinolin-5-yloxy]acetic acid methyl ester and chlorodifluoromethane.

MS: ESI (+ve) (Method B): 504 (M+H)$^+$, Retention time 4.5 min

Preparation 16d

[4-difluoromethoxy-2-ethyl-8-fluoro-3-(4-trifluoromethoxybenzyl)quinolin-5-yloxy]acetic acid A solution of [4-difluoromethoxy-2-ethyl-8-fluoro-3-(4-trifluoromethoxybenzyl)quinolin-5-yloxy]acetic acid methyl ester (0.054 g) in tetrahydrofuran (4.0 mL) was treated with 1.0M aqueous lithium hydroxide solution (0.21 mL), and the resulting mixture was stirred at room temperature for 3 hours. The mixture was acidified by the addition of 0.1M aqueous hydrochloric acid and extracted with ethyl acetate. The combined extracts were washed with saturated aqueous sodium chloride solution, dried over magnesium sulfate and then concentrated under reduced pressure. Purification of the residue by preparative reverse-phase HPLC gave title compound as a white solid (0.042 g).

$^1$H NMR (CDCl$_3$): δ 1.25 (t, J=7.5 Hz, 3H), 2.90 (q, J=7.5 Hz, 2H), 4.35 (s, 2H), 4.85 (s, 2H), 6.75 (dd, J=3.6, 8.6 Hz, 1H), 6.85 (t, J=75 Hz, 1H), 7.06 (br s, 4H), 7.25 (m, 1H)

MS: ESI (+ve) (Method A): 490 (M+H)$^+$, Retention time 12.6 min

Example 17

{8-chloro-2-difluoromethoxy-3-[4-(2,2-dimethylpropionyl)benzyl]-4-methylquinolin-5-yloxy}acetic acid

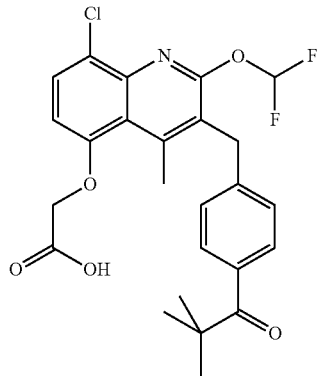 [SMILES: Cc1c(Cc2ccc(C(=O)C(C)(C)C)cc2)c(OC(F)F)nc2c(Cl)ccc(OCC(=O)O)c12]

Preparation 17a

2-[4-(2,2-dimethylpropionyl)benzyl]-3-oxothiobutyric acid S-tert-butyl ester

The title compound was prepared by the method of Preparation 11a using 1-(4-bromomethylphenyl)-2,2-dimethylpropan-1-one and 3-oxothiobutyric acid S-tert-butyl ester
MS: ESI (+ve) (Method A): 349 (M+H)⁺, Retention time 4.4 min

Preparation 17b

N-(2-chloro-5-hydroxyphenyl)-2-[4-(2,2-dimethylpropionyl)benzyl]-3-oxobutyramide The title compound was prepared by the method of Preparation 11b using 2-[4-(2,2-dimethylpropionyl)benzyl]-3-oxothiobutyric acid S-tert-butyl ester and 3-amino-4-chlorophenol.
MS: ESI (+ve) (Method B): 402 (M+H)⁺, Retention time 3.5 min

Preparation 17c 8-chloro-3-[4-(2,2-dimethylpropionyl)benzyl]-5-hydroxy-4-methyl-1H-quinolin-2-one The title compound was prepared by the method of Preparation 11c using N-(2-chloro-5-hydroxyphenyl)-2-[4-(2,2-dimethylpropionyl)benzyl]-3-oxobutyramide
MS: ESI (+ve) (Method B): 384 (M+H)⁺, Retention time 3.6 min

Preparation 17d

{8-chloro-3-[4-(2,2-dimethylpropionyl)benzyl]-4-methyl-2-oxo-1,2-dihydroquinolin-5-yloxy}acetic acid methyl ester The title compound was prepared by the method of Preparation 7a using 8-chloro-3-[4-(2,2-dimethylpropionyl)benzyl]-5-hydroxy-4-methyl-1H-quinolin-2-one and bromoacetic acid methyl ester.
MS: ESI (+ve) (Method B): 456 (M+H)⁴, Retention time 4.0 min

Preparation 17e

{8-chloro-2-difluoromethoxy-3-[4-(2,2-dimethylpropionyl)benzyl]-4-methylquinolin-5-yloxy}acetic acid methyl ester The title compound was prepared by the method of Preparation 10c using (8-chloro-3-[4-(2,2-dimethylpropionyl)benzyl]-4-methyl-2-oxo-1,2-dihydroquinolin-5-yloxy)acetic acid methyl ester and chlorodifluoromethane.
MS: ESI (+ve) (Method B): 506 (M+H)⁺, Retention time 4.7 min

Preparation 17f

{8-chloro-2-difluoromethoxy-3-[4-(2,2-dimethylpropionyl)benzyl]-4-methylquinolin-5-yloxy}acetic acid A solution of {8-chloro-2-difluoromethoxy-3-[4-(2,2-dimethylpropionyl)benzyl]-4-methylquinolin-5-yloxy}acetic acid methyl ester (0.18 g) in tetrahydrofuran (10 mL) and water (1.5 mL) was treated with 1.0M aqueous lithium hydroxide solution (0.71 mL), and the resulting mixture was stirred at room temperature for 2 hours. The mixture was concentrated under reduced pressure, diluted with water and dichloromethane and then acidified by the addition of 0.1M aqueous hydrochloric acid solution. The aqueous phase was extracted with dichloromethane and the combined organic phases dried over magnesium sulfate. The solvent was removed under reduced pressure to give title compound as a white solid (0.16 g).
¹H NMR (DMSO-d6): δ 1.20 (s, 9H), 2.85 (s, 3H), 4.25 (s, 2H), 4.80 (s, 2H), 6.95 (d, J=8.6 Hz, 1H), 7.15 (d, J=8.4 Hz, 2H), 7.60 (d, J=8.4 Hz, 2H), 7.75 (d, J=8.6 Hz, 1H), 7.85 (t, J=72 Hz, 1H)
MS: ESI (+ve) (Method B): 492 (M+H)⁺, Retention time 4.4 min

Example 18

{3-[4-(4-chloropyrazol-1-yl)benzyl]-4-difluoromethoxy-2-ethyl-8-fluoroquinolin-5-yloxy}acetic acid

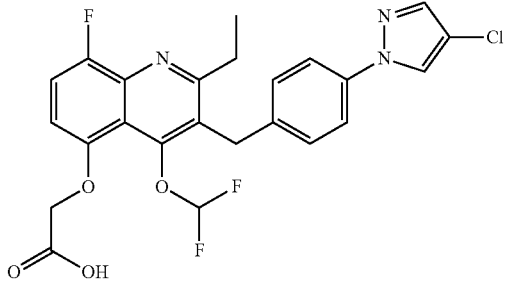 [SMILES: CCc1nc2c(F)ccc(OCC(=O)O)c2c(OC(F)F)c1Cc1ccc(-n2cc(Cl)cn2)cc1]

Preparation 18a

{3-[4-(4-chloropyrazol-1-yl)benzyl]-4-difluoromethoxy-2-ethyl-8-fluoroquinolin-5-yloxy}acetic acid methyl ester A mixture of {4-difluoromethoxy-2-ethyl-8-fluoro-3-[4-(4,4,5,5-tetramethyl[1,3,2]dioxaborolan-2-yl)benzyl]quinolin-5-yloxy}acetic acid methyl ester (0.14 g), 4-chloro-1H-pyrazole (0.053 g), cuprous acetate (0.093 g) and pyridine (3 mL) was heated at 50° C. for 116 hours. The mixture was cooled to room temperature, diluted with water (10 mL) and extracted with ethyl acetate. The combined extracts were washed with saturated aqueous sodium chloride solution, dried over magnesium sulphate and then concentrated under reduced pressure. Purification of the residue by column chromatography silica gel, eluting with a mixture of cyclohexane and ethyl acetate (1:0 to 7:3 by volume) gave title compound as a colourless oil (0.13 g).

MS: ESI (+ve) (Method B): 520 (M+H)$^+$, Retention time 4.5 min

Preparation 18b

{3-[4-(4-chloropyrazol-1-yl)benzyl]-4-difluoromethoxy-2-ethyl-8-fluoroquinolin-5-yloxy}acetic acid The title compound was prepared by the method of Preparation 1e using {3-[4-(4-chloropyrazol-1-yl)benzyl]-4-difluoromethoxy-2-ethyl-8-fluoroquinolin-5-yloxy}acetic acid methyl ester $^1$H NMR (DMSO-d6): δ 1.20 (t, J=7.4 Hz, 3H), 2.85 (q, J=7.4 Hz, 2H), 4.38 (s, 2H), 4.88 (s, 2H), 6.99 (m, 1H), 7.21 (d, J=8.6 Hz, 2H), 7.30 (t, J=75 Hz, 1H), 7.53 (t, J=9 Hz, 1H), 7.70 (d, J=8.6 Hz, 2H), 7.83 (s, 1H), 8.71 (s, 1H)

MS: ESI (+ve) (Method A): 506 (M+H)$^+$, Retention time 12.1 min

Example 19

[8-chloro-4-difluoromethoxy-2-isopropyl-3-(4-pyrazol-1-ylbenzyl) quinolin-5-yloxy]acetic acid

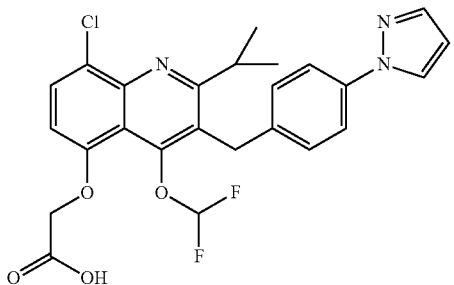 [SMILES: CC(C)c1nc2c(Cl)ccc(OCC(=O)O)c2c(OC(F)F)c1Cc1ccc(-n2cccn2)cc1]

Preparation 19a 4-methyl-3-oxo-2-(4-pyrazol-1-ylbenzyl)pentanoic acid ethyl ester The title compound was prepared by the method of Preparation 1b using 4-methyl-3-oxopentanoic acid ethyl ester and 1-(4-bromomethylphenyl)-1H-pyrazole.

MS: ESI (+ve) (Method B): 315 (M+H)$^+$, Retention time 3.8 min

Preparation 19b

[8-chloro-2-isopropyl-4-oxo-3-(4-pyrazol-1-ylbenzyl)-1,4-dihydroquinolin-5-yloxy]acetic acid methyl ester The title compound was prepared by the method of Preparation is using (3-amino-4-chlorophenoxy)acetic acid methyl ester and 4-methyl-3-oxo-2-(4-pyrazol-1-ylbenzyl)pentanoic acid ethyl ester.

MS: ESI (+ve) (Method B): 466 (M+H)$^+$, Retention time 3.8 min

Preparation 19c

[8-chloro-4-difluoromethoxy-2-isopropyl-3-(4-pyrazol-1-ylbenzyl)quinolin-5-yloxy]acetic acid methyl ester The title compound was prepared by the method of Preparation 10c using [8-chloro-2-isopropyl-4-oxo-3-(4-pyrazol-1-ylbenzyl)-1,4-dihydroquinolin-5-yloxy]acetic acid methyl ester and chlorodifluoromethane.

MS: ESI (+ve) (Method B): 516 (M±H)$^+$, Retention time 4.7 min

Preparation 19d

[8-chloro-4-difluoromethoxy-2-isopropyl-3-(4-pyrazol-1-yl-benzyl)quinolin-5-yloxy]acetic acid The title compound was prepared by the method of Preparation 1e using [8-chloro-4-difluoromethoxy-2-isopropyl-3-(4-pyrazol-1-ylbenzyl)quinolin-5-yloxy]acetic acid methyl ester.

$^1$H NMR (CDCl$_3$): δ 1.25 (d, J=6.7 Hz, 6H), 3.32 (m, 1H), 4.43 (s, 2H), 4.85 (s, 2H), 6.44 (t, J=2.1 Hz, 1H), 6.74 (d, J=8.6 Hz, 1H), 6.86 (t, J=75 Hz, 1H), 7.15 (d, J=8.3 Hz, 2H), 7.55 (d, J=8.3 Hz, 2H), 768 (d, J=8.6 Hz, 1H), 7.72 (d, J=1.6 Hz, 1H), 7.86 (d, J=2.1 Hz, 1H)

MS: ESI (+ve) (Method A): 502 (M+H)$^+$, Retention time 13.3 min

MS: ESI (+ve) (Method B): 502 (M+H)$^+$, Retention time 4.4 min

Example 20

{3-[4-(3-chloropyrazol-1-yl)benzyl]-4-difluoromethoxy-2-ethyl-8-fluoroquinolin-5-yloxy}acetic acid

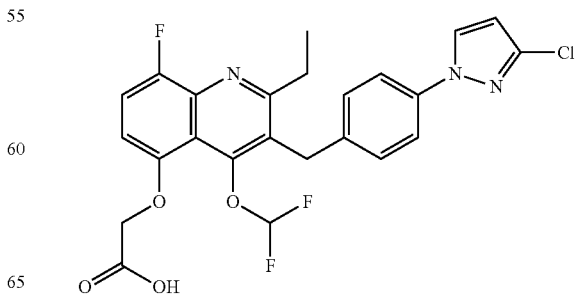

Preparation 20a

{3-[4-(3-chloropyrazol-1-yl)benzyl]-4-difluoromethoxy-2-ethyl-8-fluoroquinolin-5-yloxy}acetic acid methyl ester The title compound was prepared by the method of Preparation 18a using {4-difluoromethoxy-2-ethyl-8-fluoro-3-[4-(4,4,5,5-tetramethyl[1,3,2]dioxaborolan-2-yl)benzyl]quinolin-5-yloxy}acetic acid methyl ester and 3-chloro-1H-pyrazole.

MS: ESI (+ve) (Method B): 520 (M+H)$^+$, Retention time 4.4 min

Preparation 20b

{3-[4-(3-chloropyrazol-1-yl)benzyl]-4-difluoromethoxy-2-ethyl-8-fluoroquinolin-5-yloxy}acetic acid The title compound was prepared by the method of Preparation 1e using {3-[4-(3-chloropyrazol-1-yl)benzyl]-4-difluoromethoxy-2-ethyl-8-fluoroquinolin-5-yloxy}acetic acid methyl ester.

$^1$H NMR (DMSO-d6):δ 1.18 (t, J=7.4 Hz, 3H), 2.85 (q, J=7.4 Hz, 2H), 4.38 (s, 2H), 4.89 (s, 2H), 6.62 (d, J=2.6 Hz, 1H), 7.01 (dd, J=3.6, 9.0 Hz, 1H), 7.21 (d, J=8.6 Hz, 2H), 7.29 (t, J=75 Hz, 1H), 7.53 (m, 1H), 7.69 (d, J=8.6 Hz, 2H), 8.49 (d, J=2.6 Hz, 1H)

MS: ESI (+ve) (Method A): 506 (M+H)$^+$, Retention time 12.1 min

Example 21

[4-difluoromethoxy-8-fluoro-2-isopropyl-3-(4-pyrazol-1-ylbenzyl) quinolin-5-yloxy]acetic acid

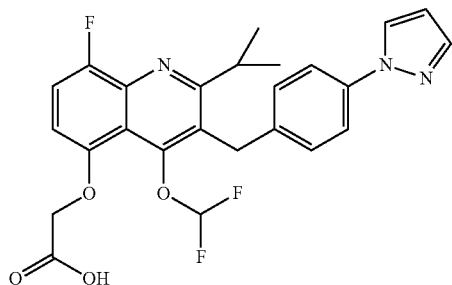 [SMILES: CC(C)c1nc2c(F)ccc(OCC(=O)O)c2c(OC(F)F)c1Cc1ccc(-n2cccn2)cc1]

Preparation 21a

[8-fluoro-2-isopropyl-4-oxo-3-(4-pyrazol-1-ylbenzyl)-1,4-dihydroquinolin-5-yloxy]acetic acid methyl ester The title compound was prepared by the method of Preparation 1c using (3-amino-4-fluorophenoxy)acetic acid methyl ester and 4-methyl-3-oxo-2-(4-pyrazol-1-ylbenzyl)pentanoic acid ethyl ester.

MS: ESI (+ve) (Method B): 450 (M+H)$^+$, Retention time 3.5 min

Preparation 21b

[4-difluoromethoxy-8-fluoro-2-isopropyl-3-(4-pyrazol-1-ylbenzyl)quinolin-5-yloxy]acetic acid methyl ester The title compound was prepared by the method of Preparation 10c using [8-fluoro-2-isopropyl-4-oxo-3-(4-pyrazol-1-ylbenzyl)-1,4-dihydroquinolin-5-yloxy]acetic acid methyl ester and chlorodifluoromethane.

MS: ESI (+ve) (Method B): 500 (M+H)$^+$, Retention time 4.3 min

Preparation 21c

[4-difluoromethoxy-8-fluoro-2-isopropyl-3-(4-pyrazol-1-ylbenzyl) quinolin-5-yloxy]acetic acid The title compound was prepared by the method of Preparation 1e using [4-difluoromethoxy-8-fluoro-2-isopropyl-3-(4-pyrazol-1-ylbenzyl)quinolin-5-yloxy]acetic acid methyl ester $^1$H NMR (CDCl$_3$): δ 1.23 (d, J=6.7 Hz, 6H), 3.32 (m, 1H), 4.43 (s, 2H), 4.82 (s, 2H), 6.44 (t, J=2.2 Hz, 1H), 6.75 (dd, J=3.3, 8.6 Hz, 1H), 6.87 (t, J=75 Hz, 1H), 7.14 (d, J=8.6 Hz, 2H), 7.26 (m, 1H), 7.56 (d, J=8.6 Hz, 2H), 7.71 (d, J=1.6 Hz, 1H), 7.86 (d, J=2.2 Hz, 1H).

MS: ESI (+ve) (Method A): 486 (M+H)$^+$, Retention time 12.2 min

MS: ESI (+ve) (Method B): 486 (M+H)$^+$, Retention time 4.2 min.

Example 22

{4-difluoromethoxy-2-ethyl-8-fluoro-3-[4-(1-isopropyl-1H-pyrazol-3-yl)benzyl]quinolin-5-yloxy}acetic acid

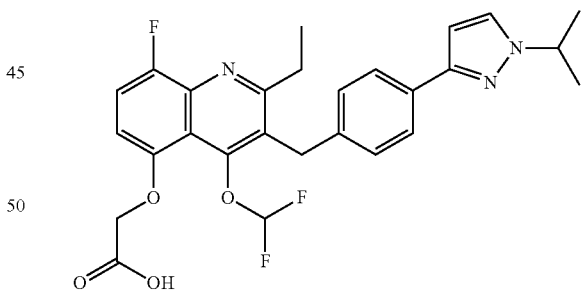

Preparation 22a 1-isopropyl-3-(4,4,5,5-tetramethyl[1,3,2]dioxaborolan-2-yl)-1H-pyrazole 3-(4,4,5,5-Tetramethyl[1,3,2]dioxaborolan-2-yl)-1H-pyrazole (0.52 g) was added to a stirred suspension of sodium hydride (60% in oil, 0.096 g) in N,N-dimethylformamide (18 mL) at 0° C., and the resulting mixture stirred at room temperature for 1 hour. The mixture was then cooled to 0° C., treated with 2-iodopropane (0.4 mL) and stirred at room temperature for 16 hours. The mixture was diluted with water (10 mL) and concentrated to low bulk under reduced pressure. The residue was extracted with ethyl acetate, and the combined extracts were washed with saturated aqueous sodium chloride solution and then dried over magnesium sulfate. The solvent was removed under reduced pressure to afford title compound (0.152 g).

Preparation 22h

{4-difluoromethoxy-2-ethyl-8-fluoro-3-[4-(1-isopropyl-1H-pyrazol-3-yl)benzyl]quinolin-5-yloxy}acetic acid A mixture of [3-(4-bromobenzyl)-4-difluoromethoxy-2-ethyl-8-fluoroquinolin-5-yloxy]acetic acid methyl ester (0.05 g), 1-isopropyl-3-(4,4,5,5-tetramethyl[1,3,2]dioxaborolan-2-yl)-1H-pyrazole (0.047 g), tetrakis(triphenylphospine)palladium (0) (0.012 g), N,N-dimethylformamide (0.3 mL) and 2.0M aqueous cesium carbonate solution (0.2 mL) was heated by microwave irradiation at 140° C. for 6 minutes. The mixture was cooled to room temperature, acidified by the addition of 1.0M aqueous hydrochloric acid solution and then extracted with ethyl acetate. The combined extracts were washed with saturated aqueous sodium chloride solution, dried over magnesium sulfate and then concentrated under reduced pressure. Purification of the residue by preparative reverse-phase HPLC gave title compound (0.014 g).

$^1$H NMR (DMSO-d6): δ 1.17 (t, J=7.5 Hz, 3H), 1.42 (d, J=6.7 Hz, 6H), 2.84 (q, J=7.5 Hz, 2H), 4.35 (s, 2H), 4.50 (m, 1H), 4.81 (s, 2H), 6.59 (d, J=2.3 Hz, 1H), 6.96 (dd, J=3.7, 8.9 Hz, 1H), 7.09 (d, J=8.3 Hz, 2H), 7.43 (t, J=75 Hz, 1H), 7.51 (dd, J=8.9, 10.0 Hz, 1H), 7.68 (d, J=8.3 Hz, 2H), 7.76 (d, J=2.3 Hz, 1H).

MS: ESI (+ve) (Method A): 514 (M+H)$^+$, Retention time 11.7 min

MS: ESI (+ve) (Method B): 514 (M+H)$^+$, Retention time 4.2 min

Example 23

{3-[4-(4-cyclopropylpyrazol-1-yl)benzyl]-4-difluoromethoxy-2-ethyl-8-fluoroquinolin-5-yloxy}acetic acid

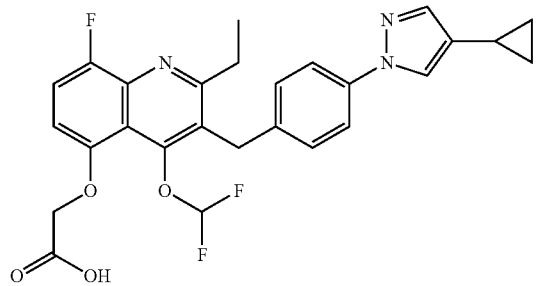 [SMILES: CCc1nc2c(F)ccc(OCC(=O)O)c2c(OC(F)F)c1Cc1ccc(-n2cc(C3CC3)cn2)cc1]

Preparation 23a (4-{[4-difluoromethoxy-2-ethyl-8-fluoro-5-(2-methoxy-2-oxoethoxy)quinolin-3-yl]methyl}phenyl)boronic acid A mixture of {4-difluoromethoxy-2-ethyl-8-fluoro-3-[4-(4,4,5,5-tetramethyl[1,3,2]dioxaborolan-2-yl)benzyl]quinolin-5-yloxy}acetic acid methyl ester (0.89 g), sodium periodate (1.7 g), ammonium acetate (0.46 g), acetone (23 mL) and water (11 mL) was stirred at room temperature for 41 hours. The mixture was concentrated to low bulk under reduced pressure, and the residue was diluted with water and then extracted with ethyl acetate. The combined extracts were washed with saturated aqueous sodium chloride solution, dried over magnesium sulphate and than concentrated under reduced pressure to afford title compound (0.70 g).

MS: ESI (+ve) (Method B): 464 (m+H)$^+$, Retention time 4.5 min

Preparation 23b

{3-[4-(4-cyclopropylpyrazol-1-yl)benzyl]-4-difluoromethoxy-2-ethyl-8-fluoroquinolin-5-yloxy}acetic acid methyl ester A mixture of (4-{[4-difluoromethoxy-2-ethyl-8-fluoro-5-(2-methoxy-2-oxoethoxy) quinolin-3-yl]methyl}phenyl)boronic acid (0.1 g), 4-cyclopropyl-1H-pyrazole (0.047 g), cuprous acetate (0.078 g) and pyridine (3 mL) was heated at 40° C. for 24 hours. The mixture was cooled to room temperature, diluted with water (10 mL) and extracted with ethyl acetate. The combined extracts were washed with saturated aqueous sodium chloride solution, dried over magnesium sulphate and then concentrated under reduced pressure. Purification of the residue by column chromatography on silica gel, eluting with a mixture of cyclohexane and ethyl acetate (1:0 to 7:3 by volume) gave title compound as pale green oil (0.09 g).

MS: ESI (+ve) (Method B): 526 (M+H)$^+$, Retention time 4.5 min

Preparation 23c

{3-[4-(4-cyclopropylpyrazol-1-yl)benzyl]-4-difluoromethoxy-2-ethyl-8-fluoroquinolin-5-yloxy}acetic acid The title compound was prepared by the method of Preparation 1e using {3-[4-(4-cyclopropylpyrazol-1-yl)benzyl]-4-difluoromethoxy-2-ethyl-8-fluoroquinolin-5-loxy}acetic acid methyl ester $^1$H NMR (DMSO-d6): δ 0.57 (m, 2H), 0.84 (m, 2H), 1.17 (t, J=7.4 Hz, 3H), 1.74 (m, 1H), 2.86 (q, J=7.4 Hz, 2H), 4.36 (s, 2H), 4.88 (s, 2H), 7.00 (dd. J=3.5, 8.7 Hz, 1H), 7.16 (d, J=8.3 Hz, 2H), 7.32 (t, J=75 Hz, 1H), 7.50 (m, 2H), 7.67 (d, J=8.3 Hz, 2H), 8.18 (s, 1H)

MS: ESI (+ve) (Method A): 512 (M+H)$^+$, Retention time 11.9 min

MS: ESI (+ve) (Method B): 512 (M+H)$^+$, Retention time 4.2 min

Example 24

{4-difluoromethoxy-2-ethyl-8-fluoro-3-[4-(2-isopropylimidazol-1-yl)benzyl]quinolin-5-yloxy}acetic acid

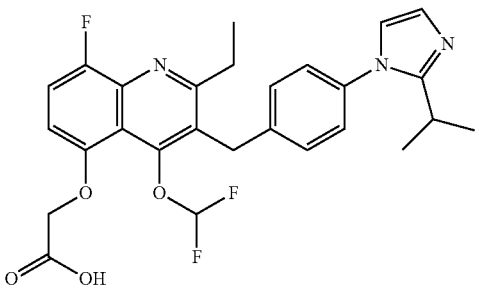 [SMILES: CCc1nc2c(F)ccc(OCC(=O)O)c2c(OC(F)F)c1Cc1ccc(-n2ccnc2C(C)C)cc1]

Preparation 24a

{4-difluoromethoxy-2-ethyl-8-fluoro-3-[4-(2-isopropylimidazol-1-yl)benzyl]quinolin-5-yloxy}acetic acid methyl ester The title compound was prepared by the method of Preparation 23b using (4-{[4-difluoromethoxy-2-ethyl-8-fluoro-5-(2-methoxy-2-oxoethoxy)quinolin-3-yl]methyl}phenyl)boronic acid and 2-isopropyl-1H-imidazole.

MS: ESI (+ve) (Method B): 528 (M+H)⁺, Retention time 2.7 min

Preparation 24b

{4-difluoromethoxy-2-ethyl-8-fluoro-3-[4-(2-isopropylimidazol-1-yl)benzyl]quinolin-5-yloxy}acetic acid The title compound was prepared by the method of Preparation 1e using {4-difluoromethoxy-2-ethyl-8-fluoro-3-[4-(2-isopropylimidazol-1-yl)benzyl]quinolin-5-yloxy}acetic acid methyl ester.

¹H NMR (DMSO-d6): δ 1.08 (d, J=6.7 Hz, 6H), 1.18 (t, J=7.3 Hz, 3H), 2.80 (m, 3H), 4.42 (s, 2H), 4.89 (s, 2H), 6.94 (br s, 1H), 7.00 (dd, J=3.7, 8.9 Hz, 1H), 7.19 (d, J=1.2 Hz, 1H), 7.25 (d, J=8.5 Hz, 2H), 7.29 (t, J=75 Hz, 1H), 7.33 (d, J=8.5 Hz, 2H), 7.54 (dd, J=8.9, 10.1 Hz, 1H)

MS: ESI (+ve) (Method A): 514 (M+H)⁺, Retention time 7.2 min

MS: ESI (+ve) (Method B): 514 (M+H)⁺, Retention time 2.6 min

Example 25

{3-[4-(3-cyclopropylpyrazol-1-yl)benzyl]-4-difluoromethoxy-2-ethyl-8-fluoroquinolin-5-yloxy}acetic acid

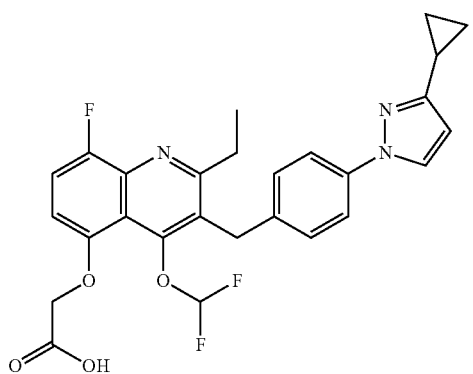 [SMILES: CCc1nc2c(F)ccc(OCC(=O)O)c2c(OC(F)F)c1Cc1ccc(-n2ccc(C3CC3)n2)cc1]

Preparation 25a

{3-[4-(3-cyclopropylpyrazol-1-yl)benzyl]-4-difluoromethoxy-2-ethyl-8-fluoroquinolin-5-yloxy}acetic acid methyl ester The title compound was prepared by the method of Preparation 23b using (4-{[4-difluoromethoxy-2-ethyl-8-fluoro-5-(2-methoxy-2-oxoethoxy)quinolin-3-yl]methyl}phenyl)boronic acid and 5-cyclopropyl-1H-pyrazole.

MS: ESI (+ve) (Method B): 526 (M+H)⁺, Retention time 4.5 min

Preparation 25b

{3-[4-(3-cyclopropylpyrazol-1-yl)benzyl]-4-difluoromethoxy-2-ethyl-8-fluoroquinolin-5-yloxy}acetic acid The title compound was prepared by the method of Preparation 1e using (3-[4-(3-cyclopropylpyrazol-1-yl)benzyl]-4-difluoromethoxy-2-ethyl-8-fluoroquinolin-5-yloxy)acetic acid methyl ester.

¹H NMR (DMSO-d6): δ 0.70 (m, 2H), 0.90 (m 2H), 1.17 (t, J=7.4 Hz, 3H), 1.95 (m, 1H), 2.86 (q, J=7.4 Hz, 2H), 4.36 (s, 2H), 4.89 (s, 2H), 6.20 (d, J=2.5 Hz, 1H), 7.01 (dd, J=3.7, 8.8 Hz, 1H), 7.16 (d, J=8.6 Hz, 2H), 7.30 (t, J=75 Hz, 1H), 7.51 (m, 1H), 7.60 (d, J=8.6 Hz, 2H), 8.24 (d, J=2.5 Hz, 1H)

MS: ESI (+ve) (Method A): 512 (M−1-Hr, Retention time 11.9 min

MS: ESI (+ve) (Method B): 512 (M+H)⁺, Retention time 4.2 min

Example 26

{3-[4-(5-cyclopropylpyrazol-1-yl)benzyl]-4-difluoromethoxy-2-ethyl-8-fluoroquinolin-5-yloxy}acetic acid

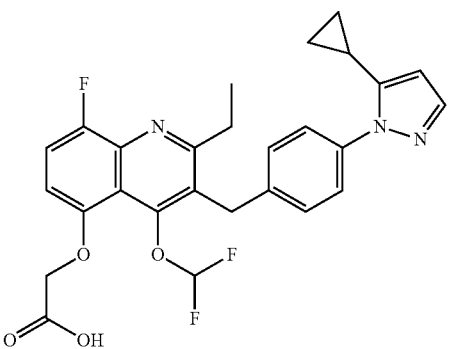 [SMILES: CCc1nc2c(F)ccc(OCC(=O)O)c2c(OC(F)F)c1Cc1ccc(-n2nccc2C2CC2)cc1]

Preparation 26a

{3-[4-(5-cyclopropylpyrazol-1-yl)benzyl]-4-difluoromethoxy-2-ethyl-8-fluoroquinolin-5-yloxy}acetic acid methyl ester The title compound was prepared by the method of Preparation 23b using (4-{[4-difluoromethoxy-2-ethyl-8-fluoro-5-(2-methoxy-2-oxoethoxy)quinolin-3-yl]methyl}phenyl)boronic acid and 5-cyclopropyl-1H-pyrazole.

MS: ESI (+ve) (Method B): 526 (M+H)⁺, Retention time 4.4 min

The title compound was prepared by the method of Preparation 1e using {3-[4-(5-cyclopropylpyrazol-1-yl)benzyl]-4-difluoromethoxy-2-ethyl-8-fluoroquinolin-5-yloxy}acetic acid methyl ester.

¹H NMR (DMSO-d6): δ 0.67 (m, 2H), 0.91 (m, 2H), 1.18 (t, J=7.4 Hz, 3H), 1.79 (m, 1H), 2.88 (q, J=7.4 Hz, 2H), 4.41 (s, 2H), 4.89 (s, 2H), 6.06 (d, J=1.6 Hz, 1H), 7.00 (dd. J=3.7, 8.9 Hz, 1H), 7.23 (d, J=8.5 Hz, 2H), 7.29 (t, J=75 Hz, 1H), 7.48 (d, J=1.6 Hz, 1H), 7.54 (m, 3H)

MS: ESI (+ve) (Method A): 512 (+H)⁺, Retention time 11.4 min

Example 27

{3-[4-(5-cyclopropylisoxazol-4-yl)benzyl]-4-difluoromethoxy-2-ethyl-8-fluoroquinolin-5-yloxy}acetic acid

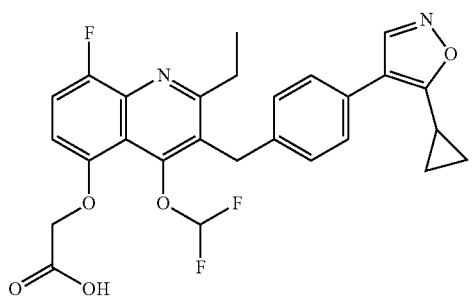 [SMILES: CCc1nc2c(F)ccc(OCC(=O)O)c2c(OC(F)F)c1Cc1ccc(-c2cnoc2C2CC2)cc1]

Preparation 27a

{3-[4-(5-cyclopropylisoxazol-4-yl)benzyl]-4-difluoromethoxy-2-ethyl-8-fluoroquinolin-5-yloxy}acetic acid methyl ester A mixture of (4-[4-difluoromethoxy-2-ethyl-8-fluoro-5-(2-methoxy-2-oxoethoxy) quinolin-3-yl]methyl)phenyl)boronic acid (0.15 g), 4-bromo-5-cyclopropylisoxazole (0.24 g), [1,1'-bis(diphenylphosphino)ferrocene]dichloropalladium (0.027 g), sodium hydrogen carbonate (0.082 g), 1,2-dimethoxyethane (1.0 mL) and water (0.4 mL) was heated at 85° C. for 2 hours. The mixture was cooled to room temperature, diluted with water (5 mL), neutralised by the addition of 1.0 M aqueous hydrochloric acid solution (1.0 mL) and extracted with ethyl acetate. The combined extracts were washed with saturated aqueous sodium chloride solution, dried over magnesium sulphate and then concentrated under reduced pressure. Purification of the residue by column chromatography on silica gel, eluting with a mixture of cyclohexane and ethyl acetate (1:0 to 7:3 by volume) gave title compound as a colourless oil (0.03 g).
MS: ESI (+ve) (Method B): 527 (M+H)$^+$, Retention time 4.5 min

Preparation 27b

{3-[4-(5-cyclopropylisoxazol-4-yl)benzyl]-4-difluoromethoxy-2-ethyl-8-fluoroquinolin-5-yloxy}acetic acid The title compound was prepared by the method of Preparation 1e using {3-[4-(5-cyclopropylisoxazol-4-yl)benzyl]-4-difluoromethoxy-2-ethyl-8-fluoroquinolin-5-yloxy}acetic acid methyl ester
$^1$H NMR (DMSO-d6): δ 0.98 (m, 2H), 1.08 (m, 2H), 1.19 (t, J=7.4 Hz, 3H), 2.26 (m, 1H), 2.87 (q, J=7.4 Hz, 2H), 4.38 (s, 2H), 4.89 (s, 2H), 7.00 (dd. J=3.8, 8.9 Hz, 1H), 7.18 (d, J=8.2 Hz, 2H), 7.29 (t, J=75 Hz, 1H), 7.51 (m, 3H), 8.77 (s, 1H)
MS: ESI (+ve) (Method A): 513 (M+H)$^+$, Retention time 12.3 min
MS: ESI (+ve) (Method B): 513 (M+H)$^+$, Retention time 4.2 min

Example 28

{2-difluoromethoxy-3-[4-(2,2-dimethylpropionyl)benzyl]-8-fluoro-4-methylquinolin-5-yloxy}acetic acid

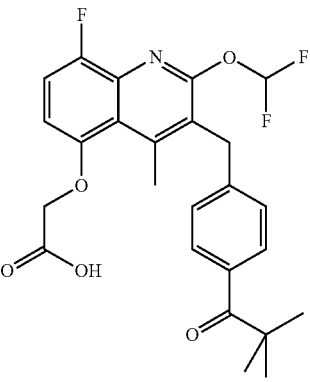 [SMILES: Cc1c(Cc2ccc(C(=O)C(C)(C)C)cc2)c(OC(F)F)nc2c(F)ccc(OCC(=O)O)c12]

Preparation 28a

2-[4-(2,2-dimethylpropionyl)benzyl]-3-oxothiobutyric acid S-tert-butyl ester

The title compound was prepared by the method of Preparation 11a using 1-(4-bromomethylphenyl)-2,2-dimethylpropan-1-one and 3-oxothiobutyric acid S-tert-butyl ester
MS: ESI (+ve) (Method B): 349 (M+H)$^+$, Retention time 4.4 min

Preparation 28b

2-[4-(2,2-dimethylpropionyl)benzyl]-N-(2-fluoro-5-hydroxyphenyl)-3-oxobutyramide The title compound was prepared by the method of Preparation 11b using 2-[4-(2,2-dimethylpropionyl)benzyl]-3-oxothiobutyric acid S-tert-butyl ester and 3-amino-4-fluorophenol.
MS: ESI (+ve) (Method B): 386 (M+H)$^+$, Retention time 3.4 min

Preparation 28c

3-[4-(2,2-dimethylpropionyl)benzyl]-8-fluoro-5-hydroxy-4-methyl-1H-quinolin-2-one The title compound was prepared by the method of Preparation 11c using 2-[4-(2,2-dimethylpropionyl)benzyl]-N-(2-fluoro-5-hydroxyphenyl)-3-oxobutyramide.
MS: ESI (+ve) (Method B): 368 (M+H)$^+$, Retention time 3.4 min

Preparation 28d

{3-[4-(2,2-dimethylpropionyl)benzyl]-8-fluoro-4-methyl-2-oxo-1,2-dihydroquinolin-5-yloxy}acetic acid methyl ester The title compound was prepared by the method of Preparation 7a using 3-[4-(2,2-dimethylpropionyl)benzyl]-8-fluoro-5-hydroxy-4-methyl-1H-quinolin-2-one and bromoacetic acid methyl ester.
MS: ESI (+ve) (Method B): 440 (M+H)$^+$, Retention time 3.7 min

Preparation 28e

{2-difluoromethoxy-3-[4-(2,2-dimethylpropionyl)benzyl]-8-fluoro-4-methylquinolin-5-yloxy}acetic acid methyl ester The title compound was prepared by the method of Preparation 10c using (3-[4-(2,2-dimethylpropionyl)benzyl]-8-fluoro-4-methyl-2-oxo-1,2-dihydroquinolin-5-yloxy)acetic acid methyl ester and chlorodifluoromethane.
MS: ESI (+ve) (Method B): 490 (M+H)$^+$, Retention time 4.6 min

Preparation 28f

{2-difluoromethoxy-3-[4-(2,2-dimethylpropionyl)benzyl]-8-fluoro-4-methylquinolin-5-yloxy}acetic acid The title compound was prepared by the method of Preparation 1e using {2-difluoromethoxy-3-[4-(2,2-dimethylpropionyl)benzyl]-8-fluoro-4-methylquinolin-5-yloxy}acetic acid methyl ester.
$^1$H NMR (DMSO-d6): 1.24 (s, 9H), 2.88 (s, 3H), 4.27 (s, 2H), 4.82 (s, 2H), 6.93 (dd, J=3.8, 8.8 Hz, 1H), 7.20 (d, J=8.4 Hz, 2H), 7.48 (dd, J=8.8, 9.9 Hz, 1H), 7.66 (d, J=8.4 Hz, 2H), 7.85 (t, J=72 Hz, 1H)
MS: ESI (+ve) (Method A): 476 (M+H)$^+$, Retention time 13.1 min
MS: ESI (+ve) (Method B): 476 (M+H)$^+$, Retention time 4.2 min

Example 29

{8-chloro-2-difluoromethoxy-4-methyl-3-[4-(1H-pyrazol-4-yl)benzyl]quinolin-5-yloxy}acetic acid

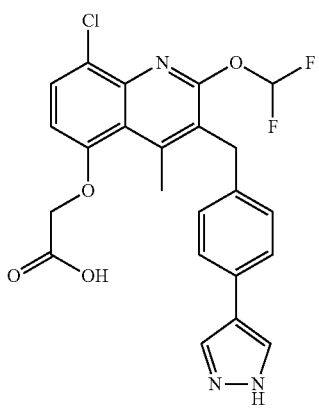 [SMILES: Cc1c(Cc2ccc(-c3cn[nH]c3)cc2)c(OC(F)F)nc2c(Cl)ccc(OCC(=O)O)c12]

Preparation 29a 2-(4-bromobenzyl)-3-oxothiobutyric acid S-tert-butyl ester

The title compound was prepared by the method of Preparation 11a using 1-bromo-4-bromomethylbenzene and 3-oxothiobutyric acid S-tert-butyl ester.
MS: ESI (+ve) (Method B): Retention time 4.4 min

Preparation 29b 2-(4-bromobenzyl)-N-(2-chloro-5-hydroxyphenyl)-3-oxobutyramide The title compound was prepared by the method of Preparation 11b using 2-(4-bromobenzyl)-3-oxothiobutyric acid S-tert-butyl ester and 3-amino-4-chlorophenol.
MS: ESI (+ve) (Method B): 397 (M+H)$^+$, Retention time 3.4 min

Preparation 29c 3-(4-bromobenzyl)-8-chloro-5-hydroxy-4-methyl-1H-quinolin-2-one The title compound was prepared by the method of Preparation 11c using 2-(4-bromobenzyl)-N-(2-chloro-5-hydroxyphenyl)-3-oxobutyramide.
MS: ESI (+ve) (Method B): 379 (M+H)$^+$, Retention time 3.6 min

Preparation 29d

[3-(4-bromobenzyl)-8-chloro-4-methyl-2-oxo-1,2-dihydroquinolin-5-yloxy]acetic acid tert-butyl ester The title compound was prepared by the method of Preparation 7a using 3-(4-bromobenzyl)-8-chloro-5-hydroxy-4-methyl-1H-quinolin-2-one and bromoacetic acid tert-butyl ester.
MS: ESI (+ve) (Method B): 493 (M+H)$^+$, Retention time 4.5 min

Preparation 29e

[3-(4-bromobenzyl)-8-chloro-2-difluoromethoxy-4-methylquinolin-5-yloxy]acetic acid tert-butyl ester The title compound was prepared by the method of Preparation 10c using [3-(4-bromobenzyl)-8-chloro-4-methyl-2-oxo-1,2-dihydroquinolin-5-yloxy]acetic acid tert-butyl ester and chlorodifluoromethane.
MS: ESI (+ve) (Method 13): 543 (M+H)$^+$, Retention time 5.1 min

Preparation 29f

{8-chloro-2-difluoromethoxy-4-methyl-3-[4-(1H-pyrazol-4-yl)benzyl]quinolin-5-yloxy}acetic acid The title compound was prepared by the method of Preparation 22b using [3-(4-bromobenzyl)-8-chloro-2-difluoromethoxy-4-methylquinolin-5-yloxy]acetic acid tert-butyl ester and pyrazole-4-boronic acid.
$^1$H NMR (DMSO-d6): 2.89 (s, 3H), 4.19 (s, 2H), 4.86 (s, 2H), 6.98 (d, J=8.5 Hz, 1H), 7.10 (d, J=8.4 Hz, 2H), 7.48 (d, J=8.4 Hz, 2H), 7.78 (d, J=8.5 Hz, 1H), 7.90 (t, J=72 Hz, 1H), 7.96 (br s, 1H), 13.01 (br s, 1H).
MS: ESI (+ve) (Method A): 474 (M+H)$^+$, Retention time 11.0 min

Example 30

{8-chloro-2-difluoromethoxy-3-[4-(1-isopropyl-1H-pyrazol-3-yl)benzyl]-4-methylquinolin-5-yloxy}acetic acid

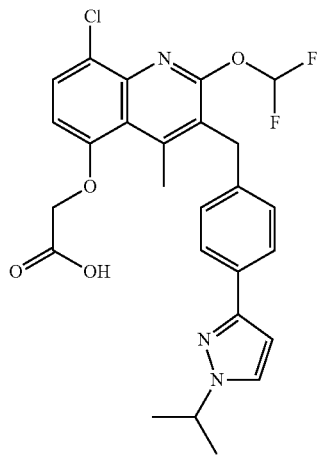 [SMILES: Cc1c(Cc2ccc(-c3ccn(C(C)C)n3)cc2)c(OC(F)F)nc2c(Cl)ccc(OCC(=O)O)c12]

Preparation 30a

{8-chloro-2-difluoromethoxy-3-[4-(1-isopropyl-1H-pyrazol-3-yl)benzyl]-4-methylquinolin-5-yloxy}acetic acid tert-butyl ester The title compound was prepared by the method of Preparation 22b using [3-(4-bromobenzyl)-8-chloro-2-difluoromethoxy-4-methylquinolin-5-yloxy]acetic acid tert-butyl ester and 1-isopropyl-3-(4,4,5,5-tetramethyl[1,3,2]dioxaborolan-2-yl)-1H-pyrazole.

MS: ESI (+ve) (Method B): 572 (M+H)$^+$, Retention time 5.0 min

Preparation 30b

{8-chloro-2-difluoromethoxy-3-[4-(1-isopropyl-1H-pyrazol-3-yl)benzyl]-4-methylquinolin-5-yloxy}acetic acid A solution of {8-chloro-2-difluoromethoxy-3-[4-(1-isopropyl-1H-pyrazol-3-yl)benzyl]-4-methylquinolin-5-yloxy}acetic acid tert-butyl ester (0.24 g) in tetrahydrofuran (5.0 mL) was treated with 1.0M aqueous sodium hydroxide solution (0.64 mL), and the resulting mixture was stirred at room temperature for 16 hour. The mixture was neutralised by the addition of 1.0M aqueous hydrochloric acid solution (0.64 mL) and then concentrated under reduced pressure. Purification of the residue by preparative reverse-phase HPLC gave the title compound as a white solid (0.051 g).

$^1$H NMR (DMSO-d6): δ 1.38 (d, J=6.6 Hz, 6H), 2.86 (s, 3H), 4.16 (s, 2H), 4.45 (m, 1H), 4.81 (s, 2H), 6.55 (d, J=2.5 Hz, 1H), 6.94 (d, J=8.7 Hz, 1H), 710 (d, J=8.4 Hz, 2H), 7.63 (d, J=8.4 Hz, 2H), 7.71 (d, J=2.5 Hz, 1H), 7.74 (d, J=8.7 Hz, 1H), 7.85 (t, J=72 Hz, 1H)

MS: ESI (+ve) (Method A): 516 (M+H)$^+$, Retention time 13.3 min

MS: ESI (+ve) (Method B): 516 (M+H)$^+$, Retention time 4.3 min

Example 31

{8-chloro-2-difluoromethoxy-3-[4-(1-isopropyl-1H-pyrazol-4-yl)benzyl]-4-methylquinolin-5-yloxy}acetic acid

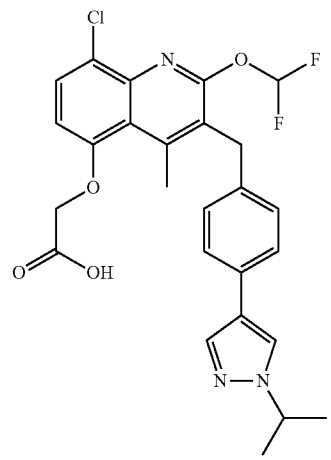 [SMILES: Cc1c(Cc2ccc(-c3cnn(C(C)C)c3)cc2)c(OC(F)F)nc2c(Cl)ccc(OCC(=O)O)c12]

Preparation 31a

{8-chloro-2-difluoromethoxy-3-[4-(1-isopropyl-1H-pyrazol-4-yl)benzyl]-4-methylquinolin-5-yloxy}acetic acid tert-butyl ester The title compound was prepared by the method of Preparation 22b using [3-(4-bromobenzyl)-8-chloro-2-difluoromethoxy-4-methylquinolin-5-yloxy]acetic acid tert-butyl ester and 1-isopropyl-4-(4,4,5,5-tetramethyl[1,3,2]dioxaborolan-2-yl)-1H-pyrazole.

MS: ESI (+ve) (Method B): 572 (M+H)$^+$, Retention time 4.9 min

Preparation 31b

{8-chloro-2-difluoromethoxy-3-[4-(1-isopropyl-1H-pyrazol-4-yl)benzyl]-4-methylquinolin-5-yloxy}acetic acid The title compound was prepared by the method of Preparation 30b using {8-chloro-2-difluoromethoxy-3-[4-(1-isopropyl-1H-pyrazol-4-yl)benzyl]-4-methylquinolin-5-yloxy}acetic acid tert-butyl ester.

$^1$H NMR (DMSO-d6): δ 1.41 (d, J=6.6 Hz, 6H), 2.89 (s, 3H), 4.19 (s, 2H), 4.46 (m, 1H), 4.84 (s, 2H), 6.97 (d, J=8.6 Hz, 1H), 7.10 (d, J=8.2 Hz, 2H), 7.46 (d, J=8.2 Hz, 2H), 7.78 (d, J=8.6 Hz, 2H), 7.89 (t, J=73 Hz, 1H), 8.12 (s, 1H)

MS: ESI (+ve) (Method A): 572 (M+H)$^+$, Retention time 12.8 min

MS: ESI (+ve) (Method B): 572 (M+H)$^+$, Retention time 4.1 min

Example 32 and 33

{8-chloro-3-[4-(3-cyclopropylpyrazol-1-yl)benzyl]-2-difluoromethoxy-4-methylquinolin-5-yloxy}acetic acid and {8-chloro-3-[4-(5-cyclopropyl-pyrazol-1-yl)benzyl]-2-difluoromethoxy-4-methylquinolin-5-yloxy}acetic acid

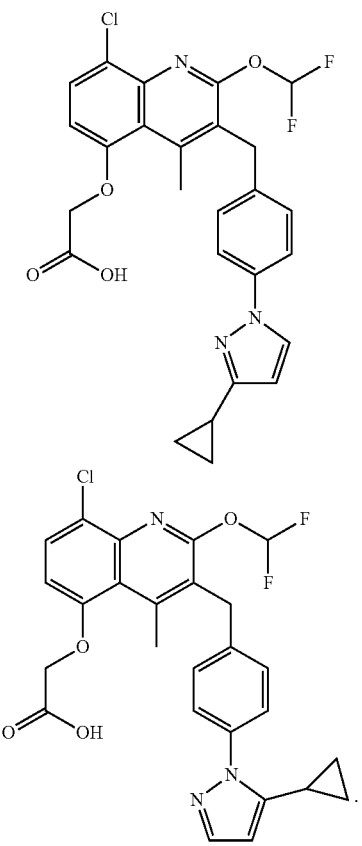

Preparation 32a and 33a

{8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester The title compound was prepared by the method of Preparation 8a using [3-(4-bromobenzyl)-8-chloro-2-difluoromethoxy-4-methylquinolin-5-yloxy]acetic acid tert-butyl ester.

MS: ESI (+ve) (Method 8): 590 (M+H)$^+$, Retention time 5.3 min

Preparation 32b and 33b

{8-chloro-3-[4-(3-cyclopropylpyrazol-1-yl)benzyl]-2-difluoromethoxy-4-methylquinolin-5-yloxy}acetic acid tert-butyl ester and {8-chloro-3-[4-(5-cyclopropylpyrazol-1-yl)benzyl]-2-difluoromethoxy-4-methylquinolin-5-yloxy}acetic add tert-butyl ester The title compounds was prepared by the method of Preparation 18a using {8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester and 3-cyclopropyl-1H-pyrazole.

{8-Chloro-3-[4-(3-cyclopropylpyrazol-1-yl)benzyl]-2-difluoromethoxy-4-methylquinolin-5-yloxy}acetic acid tert-butyl ester MS: ESI (+ve) (Method B): 570 (M+H)$^+$, Retention time 5.1 min 8-Chloro-3-[4-(5-cyclopropylpyrazol-1-yl)benzyl]-2-difluoromethoxy-4-methylquinolin-5-yloxy}acetic acid tert-butyl ester MS: ESI (+ve) (Method B): 570 (M+H)$^+$, Retention time 5.0 min

Preparation 32c

{8-chloro-3-[4-(3-cyclopropylpyrazol-1-yl)benzyl]-2-difluoromethoxy-4-methylquinolin-5-yloxy}acetic acid A solution of {8-chloro-3-[4-(3-cyclopropylpyrazol-1-yl)benzyl]-2-difluoromethoxy-4-methylquinolin-5-yloxy}acetic acid tert-butyl ester (0.11 g) in dichloromethane (8.0 mL) was treated with trifluoroacetic acid (2.0 mL), and the resulting mixture was stirred at room temperature for 5 hours. The mixture was concentrated under reduced pressure, diluted with saturated aqueous sodium acetate solution and then extracted with ethyl acetate. The combined extracts were dried over magnesium sulphate and then concentrated under reduced pressure to afford the title compound as a white solid (0.034 g).

$^1$H NMR (DMSO-d6): δ 0.70 (m, 2H), 0.89 (m, 2H), 1.94 (m, 1H), 2.90 (s, 3H), 4.22 (s, 2H), 4.61 (s, 2H), 6.19 (d, J=2.5 Hz, 1H), 6.88 (d, J=8.7 Hz, 1H), 7.19 (d, J=8.6 Hz, 2H), 7.64 (d, J=8.6 Hz, 2H), 7.73 (d, J=8.7 Hz, 1H), 7.88 (t, J=72 Hz, 1H), 8.23 (d, J=2.5 Hz, 1H)

MS: ESI (+ve) (Method A): 514 (M+H)$^+$, Retention time 13.6 min

MS: ESI (+ve) (Method B): 514 (M+H)$^+$, Retention time 4.4 min

Preparation 33c

{8-chloro-3-[4-(5-cyclopropyl-pyrazol-1-yl)benzyl]-2-difluoromethoxy-4-methylquinolin-5-yloxy}acetic acid The title compound was prepared by the method of Preparation 32c using 8-chloro-3-[4-(5-cyclopropylpyrazol-1-yl)benzyl]-2-difluoromethoxy-4-methylquinolin-5-yloxy}acetic acid tert-butyl ester.

$^1$H NMR (DMSO-d6): δ 0.69 (m, 2H), 0.93 (m, 2H), 1.80 (m, 1H), 2.93 (s, 3H), 430 (s, 2H), 4.87 (s, 2H), 6.07 (d, J=1.6 Hz, 1H), 6.99 (d, J=8.7 Hz, 1H), 7.28 (d, J=8.6 Hz, 2H), 7.49 (d, J=1.6 Hz, 1H), 7.54 (d, J=8.6 Hz, 2H), 7.80 (d, J=8.7 Hz, 1H), 7.90 (t, J=72 Hz, 1H)

MS: ESI (+ve) (Method A): 514 (M+H)$^+$, Retention time 13.0 min

MS: ESI (+ve) (Method B): 514 (M+H)$^+$, Retention time 4.3 min

Example 34

{3-[4-(5-cyclopropylpyrazol-1-yl)benzyl]-2-difluoromethoxy-8-fluoro-4-methylquinolin-5-yloxy}acetic acid

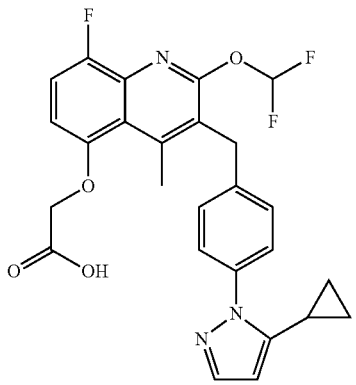 [SMILES: Cc1c(Cc2ccc(-n3nccc3C3CC3)cc2)c(OC(F)F)nc2c(F)ccc(OCC(=O)O)c12]

Preparation 34a 2-(4-bromobenzyl)-N-(2-fluoro-5-hydroxyphenyl)-3-oxobutyramide The title compound was prepared by the method of Preparation 11b using 2-(4-bromobenzyl)-3-oxothiobutyric acid S-tert-butyl ester and 3-amino-4-fluoro-phenol.

MS: ESI (+ve) (Method B): 381 (M+H)$^+$, Retention time 3.3 min

Preparation 34b 3-(4-bromobenzyl)-8-fluoro-5-hydroxy-4-methyl-1H-quinolin-2-one The title compound was prepared by the method of Preparation 11c using 2-(4-bromobenzyl)-N-(2-fluoro-5-hydroxyphenyl)-3-oxobutyramide.

MS: ESI (+ve) (Method B): 363 (M+H)$^+$, Retention time 3.4 min

Preparation 34c

[3-(4-bromobenzyl)-8-fluoro-4-methyl-2-oxo-1,2-dihydroquinolin-5-yloxy]acetic acid tert-butyl ester The title compound was prepared by the method of Preparation 7a using 3-(4-bromobenzyl)-8-fluoro-5-hydroxy-4-methyl-1H-quinolin-2-one and bromoacetic acid tert-butyl ester.

MS: ESI (+ve) (Method B): 477 (M+H)$^+$, Retention time 4.3 min

Preparation 34d

[3-(4-bromobenzyl)-2-difluoromethoxy-8-fluoro-4-methylquinolin-5-yloxy]acetic acid tert-butyl ester The title compound was prepared by the method of Preparation 10c using [3-(4-bromobenzyl)-8-fluoro-4-methyl-2-oxo-1,2-dihydroquinolin-5-yloxy]acetic acid tert-butyl ester and chlorodifluoromethane.

MS: ESI (+ve) (Method B): 527 (M+H)$^+$, Retention time 5.1 min

Preparation 34e

{2-difluoromethoxy-8-fluoro-4-methyl-3-[4-(4,4,5,5-tetramethyl[1,3,2]dioxaborolan-2-yl)benzyl]quinolin-5-yloxy}acetic acid tert-butyl ester The title compound was prepared by the method of Preparation 8a using [3-(4-bromobenzyl)-2-difluoromethoxy-8-fluoro-4-methylquinolin-5-yloxy]acetic acid tert-butyl ester.

MS: ESI (+ve) (Method B): 574 (M+H)$^+$, Retention time 5.1 min

Preparation 34f 4-(5-tert-butoxycarbonylmethoxy-2-difluoromethoxy-8-fluoro-4-methylquinolin-3-ylmethyl) boronic acid The title compound was prepared by the method of Preparation 23a using {2-difluoromethoxy-8-fluoro-4-methyl-3-[4-(4,4,5,5-tetramethyl[1,3,2]dioxaborolan-2-yl)benzyl]quinolin-5-yloxy}acetic acid tert-butyl ester.

MS: ESI (+ve) (Method B): 492 (M+H)$^+$, Retention time 4.1 min

Preparation 34g

{3-[4-(5-cyclopropylpyrazol-1-yl)benzyl]-2-difluoromethoxy-8-fluoro-4-methylquinolin-5-yloxy}acetic acid tert-butyl ester The title compound was prepared by the method of Preparation 18a using 4-(5-tert-butoxycarbonylmethoxy-2-difluoromethoxy-8-fluoro-4-methylquinolin-3-ylmethyl) boronic acid and 5-cyclopropyl-1H-pyrazole.

MS: ESI (+ve) (Method B): 554 (M+H)$^+$, Retention time 4.8 min

Preparation 34h

{3-[4-(5-cyclopropylpyrazol-1-yl)benzyl]-2-difluoromethoxy-8-fluoro-4-methylquinolin-5-yloxy}acetic acid The title compound was prepared by the method of Preparation 32c using (3-[4-(5-cyclopropylpyrazol-1-yl)benzyl]-2-difluoromethoxy-8-fluoro-4-methylquinolin-5-yloxy)acetic acid tert-butyl ester.

$^1$H NMR (DMSO-d6): δ 0.67-0.71 (m, 2H), 0.90-0.95 (m, 2H), 1.78-1.84 (m, 1H), 2.93 (s, 3H), 4.30 (s, 2H), 4.83 (s, 2H), 6.07 (d, J=1.5 Hz, 1H), 6.94 (dd, J=4.0, 8.4 Hz, 1H), 7.29 (d, J=8.4 Hz, 2H), 7.46-7.51 (m, 2H), 7.54 (d, J=8.4 Hz, 2H), 7.88 (t, J=7.2 Hz, 1H), 13.2 (br s, 1H)

MS: ESI (+ve) (Method A): 498 (M+H)$^+$, Retention time 12.9 min

MS: ESI (+ve) (Method B): 498 (M+H)$^+$, Retention time 4.1 min

Example 35

{3-[4-(4-cyclopropylpyrazol-1-yl)benzyl]-2-difluoromethoxy-8-fluoro-4-methylquinolin-5-yloxy}acetic acid

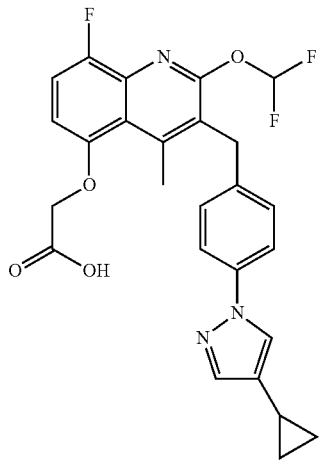 [SMILES: Cc1c(Cc2ccc(-n3cc(C4CC4)cn3)cc2)c(OC(F)F)nc2c(F)ccc(OCC(=O)O)c12]

Preparation 35a

{3-[4-(4-cyclopropylpyrazol-1-yl)benzyl]-2-difluoromethoxy-8-fluoro-4-methylquinolin-5-yloxy}acetic acid tert-butyl ester The title compound was prepared by the method of Preparation 18a using 4-(5-tert-butoxycarbonylmethoxy-2-difluoromethoxy-8-fluoro-4-methylquinolin-3-ylmethyl) boronic acid and 4-cyclopropyl-1H-pyrazole.

MS: ESI (+ve) (Method B): 554 (M+H)$^+$, Retention time 4.9 min

Preparation 35b

{3-[4-(4-cyclopropylpyrazol-1-yl)benzyl]-2-difluoromethoxy-8-fluoro-4-methylquinolin-5-yloxy}acetic acid The title compound was prepared by the method of Preparation 32c using {3-[4-(4-cyclopropylpyrazol-1-yl)benzyl]-2-difluoromethoxy-8-fluoro-4-methylquinolin-5-yloxy}acetic acid tert-butyl ester.

$^1$H NMR (DMSO-d6): δ 0.55-0.58 (m, 2H), 0.82-0.87 (m, 2H), 1.71-1.78 (m, 1H), 3.28 (s, 3H), 4.23 (s, 2H), 4.74 (s, 2H), 6.90 (dd, J=4.0, 9.0 Hz, 1H), 7.21 (d, J=(16 Hz, 2H), 7.47 (dd, J=9.0, 9.7 Hz, 1H), 7.50 (s, 1H), 7.67 (d, 8.6 Hz, 2H), 7.87 (t, J=7.2 Hz, 1H), 8.18 (s, 1H)

MS: ESI (+ve) (Method A): 498 (M+H)$^+$, Retention time 12.4 min

MS: ESI (+ve) (Method B): 498 (M+H)$^+$, Retention time 4.2 min

Example 36

{2-difluoromethoxy-8-fluoro-3-[4-(2-isopropylimidazol-1-yl)benzyl]-4-methylquinolin-5-yloxy}acetic acid

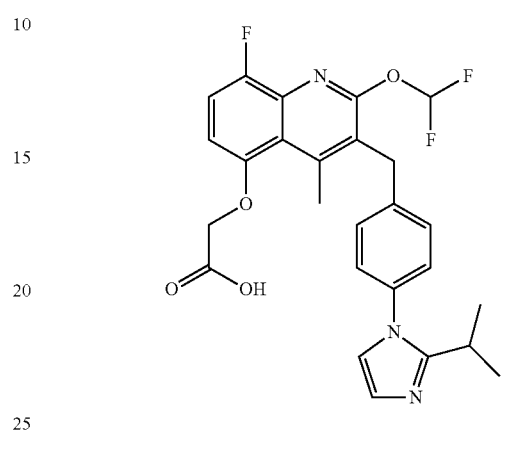

Preparation 36a

{2-difluoromethoxy-8-fluoro-3-[4-(2-isopropylimidazol-1-yl)benzyl]-4-methylquinolin-5-yloxy}acetic acid tert-butyl ester The title compound was prepared by the method of Preparation 18a using 4-(5-tert-butoxycarbonylmethoxy-2-difluoromethoxy-8-fluoro-4-methylquinolin-3-ylmethyl) boronic acid and 2-isopropyl-1H-imidazole.

MS: ESI (+ve) (Method B): 556 (M+H)$^+$, Retention time 3.1 min

Preparation 36b

{2-difluoromethoxy-8-fluoro-3-[4-(2-isopropylimidazol-1-yl)benzyl]-4-methylquinolin-5-yloxy}acetic acid The title compound was prepared by the method of Preparation 32c using {2-difluoromethoxy-8-fluoro-3-[4-(2-isopropylimidazol-1-yl)benzyl]-4-methylquinolin-5-yloxy}acetic acid tert-butyl ester.

$^1$H NMR (DMSO-d6): δ 1.10 (d, J=6.9 Hz, 6H), 2.90 (m, 1H), 2.93 (s, 3H), 4.31 (s, 2H), 4.83 (s, 2H), 6.89 (d, J=1.3 Hz, 1H), 6.94 (dd, J=4.1, 99 Hz, 1H), 7.15 (d, J=1.3 Hz, 1H), 7.28-7.33 (m, 4H), 7.44 (dd, J=8.9, 9.9 Hz, 1H), 7.88 (t, J=72 Hz, 1H)

MS: ESI (+ve) (Method A): 500 (M+H)$^+$, Retention time 8.7 min

MS: ESI (+ve) (Method B): 500 (M+H)$^+$, Retention time 2.7 min

Example 37

{8-chloro-3-[4-(4-cyclopropylpyrazol-1-yl)benzyl]-2-difluoromethoxy-4-methylquinolin-5-yloxy}acetic acid

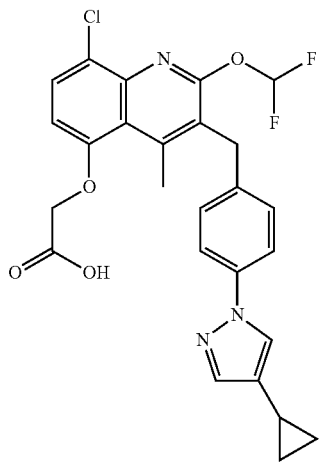 [SMILES: Cc1c(Cc2ccc(-n3cc(C4CC4)cn3)cc2)c(OC(F)F)nc2c(Cl)ccc(OCC(=O)O)c12]

Preparation 37a

{8-chloro-3-[4-(4-cyclopropylpyrazol-1-yl)benzyl]-2-difluoromethoxy-4-methylquinolin-5-yloxy}acetic acid tert-butyl ester The title compounds was prepared by the method of Preparation 18a using {8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester and 4-cyclopropyl-1H-pyrazole.

MS: ESI (+ve) (Method B): 570 (M+H)$^+$, Retention time 5.0 min

Preparation 37b

{8-chloro-3-[4-(4-cyclopropylpyrazol-1-yl)benzyl]-2-difluoromethoxy-4-methylquinolin-5-yloxy}acetic acid The title compound was prepared by the method of Preparation 32c using (8-chloro-3-[4-(4-cyclopropylpyrazol-1-yl)benzyl]-2-difluoromethoxy-4-methylquinolin-5-yloxy)acetic acid tert-butyl ester.

$^1$H NMR (DMSO-d6): δ 0.56 (m, 2H), 0.83 (m, 2H), 1.73 (s, 1H), 2.86 (s, 3H), 4.18 (s, 2H), 4.69 (s, 2H), 6.92 (d, J=8.7 Hz, 1H), 7.20 (d, J=8.7 Hz, 2H), 7.49 (s, 1H), 7.64 (d, J=8.7 Hz, 2H), 7.76 (d, J=8.7 Hz, 1H), 7.88 (t, J=72 Hz, 1H), 8.17 (s, 1H)

MS: ESI (+ve) (Method A): 514 (M+H)$^+$, Retention time 13.7 min

MS: ESI (+ve) (Method B): 514 (M+H)$^+$, Retention time 4.1 min

Example 38

{3-[4-(3-cyclopropylpyrazol-1-yl)benzyl]-2-difluoromethoxy-8-fluoro-4-methylquinolin-5-yloxy}acetic acid

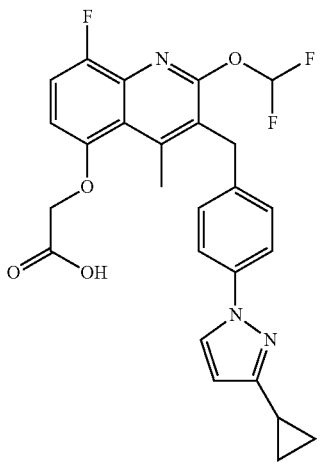 [SMILES: Cc1c(Cc2ccc(-n3ccc(C4CC4)n3)cc2)c(OC(F)F)nc2c(F)ccc(OCC(=O)O)c12]

Preparation 38a

{3-[4-(3-cyclopropylpyrazol-1-yl)benzyl]-2-difluoromethoxy-8-fluoro-4-methylquinolin-5-yloxy}acetic acid tert-butyl ester The title compound was prepared by the method of Preparation 18a using 4-(5-tert-butoxycarbonylmethoxy-2-difluoromethoxy-8-fluoro-4-methylquinolin-3-ylmethyl) boronic acid and 3-cyclopropyl-1H-pyrazole.

MS: ESI (+ve) (Method B): 554 (M+H)$^+$, Retention time 4.8 min

Preparation 38b

{3-[4-(3-cyclopropylpyrazol-1-yl)benzyl]-2-difluoromethoxy-8-fluoro-4-methylquinolin-5-yloxy}acetic acid The title compound was prepared by the method of Preparation 32c using {3-[4-(3-cyclopropylpyrazol-1-yl)benzyl]-2-difluoromethoxy-8-fluoro-4-methylquinolin-5-yloxy}acetic acid tert-butyl ester.

$^1$H NMR (DMSO-d6): δ 0.55-0.58 (m, 2H), 0.82-0.87 (m, 2H), 1.71-1.78 (m, 1H), 2.91 (s, 3H), 4.23 (s, 2H), 4.74 (s, 2H), 6.90 (dd, J=4.0, 9.0 Hz, 1H), 7.21 (d, J=8.6 Hz, 2H), 7.47 (dd, J=9.0, 9.7 Hz, 1H), 7.50 (s, 1H), 7.66 (d, J=8.6 Hz, 2H), 7.87 (t, J=72 Hz, 1H), 8.18 (s, 1H)

MS: ESI (+ve) (Method A): 498 (M+H)$^+$, Retention time 13.0 min

MS: ESI (+ve) (Method B): 498 (M+H)$^+$, Retention time 4.2 min

Example 39

{8-chloro-3-[4-(3-chloropyrazol-1-yl)benzyl]-2-difluoromethoxy-4-methylquinolin-5-yloxy}acetic acid

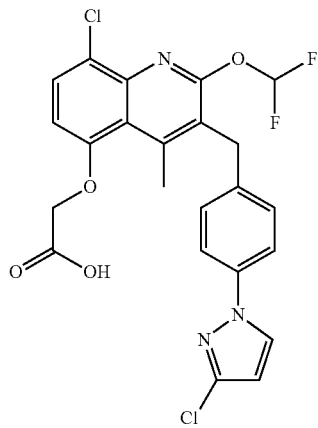 [SMILES: Cc1c(Cc2ccc(-n3ccc(Cl)n3)cc2)c(OC(F)F)nc2c(Cl)ccc(OCC(=O)O)c12]

Preparation 39a

{8-chloro-3-[4-(3-chloropyrazol-1-yl)benzyl]-2-difluoromethoxy-4-methylquinolin-5-yloxy}acetic acid tert-butyl ester The title compound was prepared by the method of Preparation 18a using {8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester and 3-chloro-1H-pyrazole.

MS: ESI (+ve) (Method B): 564 (M+H)$^+$, Retention time 5.0 min

Preparation 39b

{8-chloro-3-[4-(3-chloropyrazol-1-yl)benzyl]-2-difluoromethoxy-4-methylquinolin-5-yloxy}acetic acid The title compound was prepared by the method of Preparation 32c using {8-chloro-3-[4-(3-chloropyrazol-1-yl)benzyl]-2-difluoromethoxy-4-methylquinolin-5-yloxy}acetic acid tert-butyl ester.

$^1$H NMR (DMSO-d6): δ 2.91 (s, 3H), 4.23 (s, 2H), 4.48 (s, 2H), 6.60 (d, J=2.6 Hz, 1H), 6.83 (d, J=8.6 Hz, 1H), 7.23 (d, J=8.3 Hz, 2H), 7.68 (m, 3H), 7.88 (t, J=72 Hz, 1H), 8.48 (d, J=2.6 Hz, 1H)

MS: ESI (+ve) (Method A): 508 (M+H)$^+$, Retention time 13.1 min

MS: ESI (+ve) (Method B): 508 (M+H)$^+$, Retention time 4.4 min

Example 40

{3-[4-(5-cyclopropylisoxazol-4-yl)benzyl]-2-difluoromethoxy-8-fluoro-4-methylquinolin-5-yloxy}acetic acid

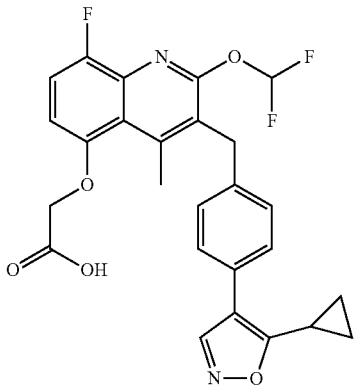 [SMILES: Cc1c(Cc2ccc(-c3cnoc3C3CC3)cc2)c(OC(F)F)nc2c(F)ccc(OCC(=O)O)c12]

Preparation 40a 4-bromo-5-cyclopropylisoxazole

The title compound was prepared by the method described in US65629651.

$^1$H NMR (CDCl$_3$): δ 1.16 (m, 4H), 2.09 (m, 1H), 8.11 (s, 1H)

Preparation 40b

{3-[4-(5-cyclopropylisoxazol-4-yl)benzyl]-2-difluoromethoxy-8-fluoro-4-methylquinolin-5-yloxy}acetic acid tert-butyl ester The title compound was prepared by the method of Preparation 27a using 4-(5-tert-butoxycarbonylmethoxy-2-difluoromethoxy-8-fluoro-4-methylquinolin-3-ylmethyl) boronic acid and 4-bromo-5-cyclopropylisoxazole.

MS: ESI (+ve) (Method B): 555 (M+H)$^+$, Retention time 4.9 min

Preparation 40c

{3-[4-(5-cyclopropylisoxazol-4-yl)benzyl]-2-difluoromethoxy-8-fluoro-4-methylquinolin-5-yloxy}acetic acid The title compound was prepared by the method of Preparation 32c using {8-chloro-3-[4-(3-chloropyrazol-1-yl)benzyl]-2-difluoromethoxy-4-methylquinolin-5-yloxy}acetic acid tert-butyl ester.

$^1$H NMR (DMSO-d6): δ 0.98 (m, 2H), 1.08 (m, 2H), 2.28 (m, 1H), 2.91 (s, 3H), 4.26 (s, 2H), 4.83 (s, 2H), 6.94 (dd, J=4.0, 8.9 Hz, 1H), 7.24 (d, J=8.2 Hz, 2H), 7.48 (dd, J=8.9, 9.7 Hz, 1H), 7.53 (d, J=8.2 Hz, 2H), 7.88 (t, J=72 Hz, 1H), 8.77 (s, 1H)

MS: ESI (+ve) (Method A): 499 (M+H)$^+$, Retention time 12.3 min

MS: ESI (+ve) (Method B): 499 (M+H)$^+$, Retention time 4.2 min

Example 41

{8-chloro-3-[4-(4-chloropyrazol-1-yl)benzyl]-2-difluoromethoxy-4-methylquinolin-5-yloxy}acetic acid

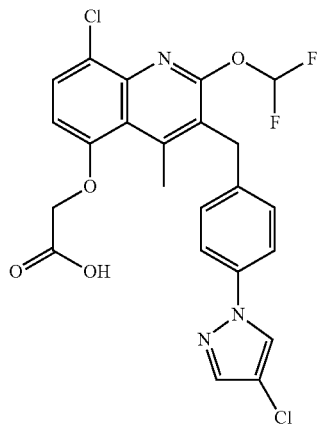 [SMILES: Cc1c(Cc2ccc(-n3cc(Cl)cn3)cc2)c(OC(F)F)nc2c(Cl)ccc(OCC(=O)O)c12]

Preparation 41a

{8-chloro-3-[4-(4-chloropyrazol-1-yl)benzyl]-2-difluoromethoxy-4-methylquinolin-5-yloxy}acetic acid tert-butyl ester The title compound was prepared by the method of Preparation 18a using {8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester and 4-chloro-1H-pyrazole.

MS: ESI (+ve) (Method B): 564 (M+H)+, Retention time 5.1 min

Preparation 41b

{8-chloro-3-[4-(4-chloropyrazol-1-yl)benzyl]-2-difluoromethoxy-4-methylquinolin-5-yloxy}acetic acid The title compound was prepared by the method of Preparation 32c using {8-chloro-3-[4-(4-chloropyrazol-1-yl)benzyl]-2-difluoromethoxy-4-methylquinolin-5-yloxy}acetic acid tert-butyl ester.

$^1$H NMR (DMSO-d6): δ 2.90 (s, 3H), 4.26 (s, 2H), 4.86 (s, 2H), 6.98 (d, J=8.7 Hz, 1H), 7.26 (d, J=8.6 Hz, 2H), 7.70 (d, J=8.6 Hz, 2H), 7.79 (d, J=8.7 Hz, 1H), 7.82 (s, 1H), 7.89 (t, J=72 Hz, 1H), 8.71 (s, 1H)

MS: ESI (+ve) (Method A): 508 (M±H)+, Retention time 13.7 min

Example 42

{8-chloro-2-difluoromethoxy-3-[4-(2-isopropylimidazol-1-yl)benzyl]-4-methylquinolin-5-yloxy}acetic acid

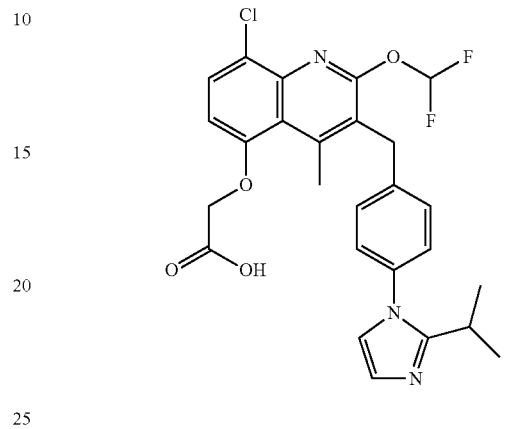

Preparation 42a

{8-chloro-2-difluoromethoxy-3-[4-(2-isopropylimidazol-1-yl)-benzyl]-4-methylquinolin-5-yloxy}acetic acid tert-butyl ester The title compound was prepared by the method of Preparation 18a using {8-chloro-2-difluoromethoxy-4-methyl-3-[4-(4,4,5,5-tetramethyl[1,3,2]dioxaborolan-2-yl)benzyl]quinolin-5-yloxy}acetic acid tert-butyl ester and 2-isopropyl-1H-imidazole.

MS: ESI (+ve) (Method B): 572 (M+H)+, Retention time 3.2 min

Preparation 42b

{8-chloro-2-difluoromethoxy-3-[4-(2-isopropylimidazol-1-yl)benzyl]-4-methylquinolin-5-yloxy}acetic acid The title compound was prepared by the method of Preparation 32c using (8-chloro-2-difluoromethoxy-3-[4-(2-isopropylimidazol-1-yl)benzyl]-4-methylquinolin-5-yloxy)acetic acid tert-butyl ester.

$^1$H NMR (DMSO-d6): δ 1.11 (d, J=6.7 Hz, 6H), 2.92 (m, 4H), 4.31 (s, 2H), 4.81 (s, 2H), 6.88 (d, J=1.3 Hz, 1H), 6.97 (s, J=8.6 Hz, 1H), 7.14 (d, J=1.3 Hz, 1H), 7.30 (s, 4H), 7.79 (d, J=8.6 Hz, 1H), 7.90 (t, J=72 Hz, 1H)

MS: ESI (+ve) (Method A): 516 (M+H)+, Retention time 8.3 min

MS: ESI (+ve) (Method B): 516 (M+H)+, Retention time 2.9 min

Example 43

[8-fluoro-2-isopropyl-4-methyl-3-(4-pyrazol-1-yl-benzyl)quinolin-5-yloxy]acetic acid

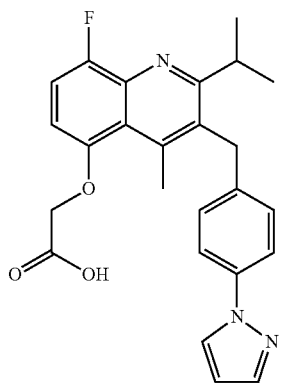 [SMILES: Cc1c(Cc2ccc(-n3cccn3)cc2)c(C(C)C)nc2c(F)ccc(OCC(=O)O)c12]

Preparation 43a phosphoric acid mono[8-fluoro-4-methyl-2-oxo-3-(4-pyrazol-1-ylbenzyl)-1,2-dihydroquinolin-5-yl] ester A mixture of 8-fluoro-5-hydroxy-4-methyl-3-(4-pyrazol-1-ylbenzyl)-1H-quinolin-2-one (1.1 g) and phosphorus oxychloride (9.1 mL) was heated by microwave irradiation at 110° C. for 1 hour. The mixture was cooled to room temperature, poured into ice/water (100 mL), and the resulting precipitate was collected by filtration, washed with water and dried to afford title compound (1.2 g).

Preparation 43b 2-chloro-8-fluoro-4-methyl-3-(4-pyrazol-1-ylbenzyl)quinolin-5-ol A mixture of phosphoric acid mono[8-fluoro-4-methyl-2-oxo-3-(4-pyrazol-1-ylbenzyl)-1,2-dihydroquinolin-5-yl]ester (0.34 g), potassium phosphate (0.88 g) and N,N-dimethylformamide (8.0 mL) was heated by microwave irradiation at 200° C. for 10 minutes. The mixture was cooled to room temperature, filtered through Celite and concentrated to under reduced pressure. Purification of the residue by column chromatography on silica gel, eluting with a mixture of cyclohexane and ethyl acetate (1:0 to 1:1 by volume) gave title compound as a yellow solid (0.11 g).

$^1$H NMR (DMSO-d6): δ 2.89 (s, 3H), 4.41 (s, 2H), 6.51 (d, J=1.8, 2.5 Hz, 1H), 6.90 (dd, J=4.4, 8.6 Hz, 1H), 7.21 (m, 2H), 7.41 (dd, J=8.6, 10.1 Hz, 1H), 7.71 (dd, J=0.5, 1.8 Hz, 1H), 7.74 (m, 2H), 8.42 (dd, J=0.8, 2.5 Hz, 1H), 10.5 (s, 1H).

MS: ESI (+ve) (Method B): 368 (M+H)$^+$, Retention time 3.7 min.

Preparation 43c 8-fluoro-2-isopropenyl-4-methyl-3-(4-pyrazol-1-ylbenzyl)quinolin-5-ol A mixture of 2-chloro-8-fluoro-4-methyl-3-(4-pyrazol-1-ylbenzyl)quinolin-5-ol (0.22 g), 2-isopropenyl-4,4,5,5-tetramethyl[1,3,2]dioxaborolane (0.23 mL), potassium phosphate monohydrate (0.68 g) and N,N-dimethylformamide (3.0 mL) was purged with argon for 20 minutes, and then treated with [1,1'-bis(diphenylphosphino)ferrocene]dichloropalladium (II) (0.048 g), and the mixture heated at 90° C. for 12 hours. The mixture was cooled to room temperature, filtered through Celite and concentrated under reduced pressure. The residue was diluted with saturated aqueous ammonium chloride solution (50 mL) and extracted with ethyl acetate (3×20 mL). The combined extracts were washed with water (5.0 mL) and saturated aqueous sodium chloride solution (5.0 mL), dried over magnesium sulfate and concentrated under reduced pressure. Purification of the residue by column chromatography on silica gel, eluting with a mixture of cyclohexane and ethyl acetate (1:0 to 1:1 by volume) gave title compound as a white solid (0.082 g).

MS: ESI (+ve) (Method B): 374 (M+H)$^+$, Retention time 3.3 min.

Preparation 43d 8-fluoro-2-isopropyl-4-methyl-3-(4-pyrazol-1-ylbenzyl)quinolin-5-ol A mixture of 8-fluoro-2-isopropenyl-4-methyl-3-(4-pyrazol-1-ylbenzyl)quinolin-5-ol (0.13 g), palladium hydroxide (0.047 g) and methanol (3.4 mL) was stirred at room temperature for 20 hours under an atmosphere of hydrogen. The mixture was filtered through Celite and concentrated under reduced pressure. Purification of the residue by column chromatography on silica gel, eluting with a mixture of cyclohexane and ethyl acetate (1:0 to 1:1 by volume) gave title compound as a white foam (0.077 g).

$^1$H NMR (DMSO-d6): δ 1.19 (s, 3H), 1.20 (s, 3H), 2.81 (s, 3H), 3.37 (m, 1H), 4.32 (s, 2H), 6.51 (dd, J=1.8, 2.5 Hz, 1H), 6.77 (dd, J=4.4, 8.5 Hz, 1H), 7.12 (m, 2H), 7.26 (dd, J=8.6, 10.3 Hz, 1H), 7.70 (dd, J=0.5, 1.7 Hz, 1H), 7.74 (m, 2H), 8.42 (dd, J=0.5, 2.5 Hz, 1H), 10.1 (s, 1H).

MS: ESI (+ve) (Method B): 376 (M+H)$^+$, Retention time 3.9 min.

Preparation 43e

[8-fluoro-2-isopropyl-4-methyl-3-(4-pyrazol-1-yl-benzyl)quinolin-5-yloxy]acetic acid methyl ester A mixture of 8-fluoro-2-isopropyl-4-methyl-3-(4-pyrazol-1-O-benzyl)quinolin-5-ol (0.066 g), potassium carbonate (0.073 g) and N,N-dimethylformamide (0.35 mL) was treated with methyl bromoacetate (0.020 mL), and the resulting mixture was stirred at room temperature for 12 hours. The mixture was diluted with saturated aqueous ammonium chloride solution (3.0 mL) and water (20 mL), and extracted with ethyl acetate (3×5 mL). The combined extracts were washed with water (2.0 mL) and saturated aqueous sodium chloride solution (2.0 mL), and dried over magnesium sulfate. Purification of the residue by column chromatography on silica gel, eluting with a mixture of cyclohexane and ethyl acetate (1:0 to 1:1 by volume) gave title compound as a colourless oil (0.079 g).

$^1$H NMR (DMSO-d6): δ 1.20 (s, 3H), 1.22 (s, 3H), 2.84 (s, 3H), 3.37 (m, 1H), 3.72 (s, 3H), 4.37 (s, 2H), 4.94 (s, 2H), 6.51 (dd, J=1.8, 2.5 Hz, 1H), 6.90 (dd, J=4.1, 8.9 Hz, 1H), 7.13 (m, 2H), 7.38 (dd, J=8.7, 10.0 Hz, 1H), 7.70 (dd, J=0.5, 1.8 Hz, 1H), 7.74 (m, 2H), 8.42 (dd, J=0.6, 2.5 Hz, 1H).

MS: ESI (+ve) (Method B): 448 (M+H)$^+$, Retention time 4.5 min.

Preparation 43f

[8-fluoro-2-isopropyl-4-methyl-3-(4-pyrazol-1-yl-benzyl)quinolin-5-yloxy]acetic acid A solution of [8-fluoro-2-isopropyl-4-methyl-3-(4-pyrazol-1-ylbenzyl)quinolin-5-yloxy]acetic acid methyl ester (0.062 g) in tetrahydrofuran (0.70 mL) and water (0.70 mL) was treated with lithium hydroxide (0.033 g), and the resulting mixture was stirred at room temperature. After 24 hours, the mixture was treated with additional lithium hydroxide (0.033 g) and stirring continued for 16 hours. The mixture was cooled to 0° C., acidified with 1.0 M aqueous hydrochloric acid and extracted with ethyl acetate (3×5.0 mL). The combined extracts were washed with saturated aqueous sodium chloride solution (2.0 mL), dried over magnesium sulfate and concentrated under reduced pressure. Purification of the residue by preparative reverse-phase HPLC, eluting with a mixture of acetonitrile and water (40:60 to 19:1 by volume) gave title compound as a yellow solid (0.015 g).

$^1$H NMR (DMSO-d6): δ 1.20 (s, 3H), 1.22 (s, 3H), 2.85 (s, 3H), 3.36 (m, 1H), 4.37 (s, 2H), 4.81 (s, 2H), 6.51 (dd, J=1.8, 2.5 Hz, 1H), 6.87 (dd, J=4.1, 8.8 Hz, 1H), 7.13 (m, 2H), 7.38 (dd, J=8.7, 10.1 Hz, 1H), 7.70 (dd, J=0.5, 1.7 Hz, 1H), 7.74 (m, 2H), 8.42 (dd, J=0.6, 2.5 Hz, 1H), 13.1 (br s, 1H).

MS: ESI (+ve) (Method A): 434 (M+H)$^+$, Retention time 11.8 min.

Example 44

[8-chloro-2-isopropyl-4-methyl-3-(4-pyrazol-1-yl-benzyl)quinolin-5-yloxy]acetic acid

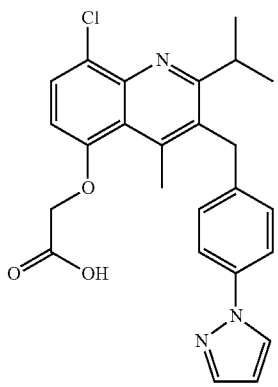 [SMILES: Cc1c(Cc2ccc(-n3cccn3)cc2)c(C(C)C)nc2c(Cl)ccc(OCC(=O)O)c12]

Preparation 44a phosphoric acid mono[2,8-dichloro-4-methyl-3-(4-pyrazol-1-ylbenzyl)quinolin-5-yl]ester A mixture of 8-chloro-5-hydroxy-4-methyl-3-(4-pyrazol-1-ylbenzyl)-1H-quinolin-2-one (1.4 g) and phosphorus oxychloride (20 mL) was heated by microwave irradiation at 110° C. for 15 minutes. The mixture was cooled to room temperature, poured into ice/water (100 mL), and the resulting precipitate was collected by filtration, washed with water and dried to afford title compound (0.92 g).

MS: ESI (+ve) (Method B): 464 (M+H)$^+$, Retention time 3.4 min.

Preparation 44b 8-chloro-2-isopropenyl-4-methyl-3-(4-pyrazol-1-ylbenzyl)quinolin-5-ol A mixture phosphoric acid mono-[2,8-dichloro-4-methyl-3-(4-pyrazol-1-yl-benzyl)quinolin-5-yl] ester (0.92 g), 2-isopropenyl-4,4,5,5-tetramethyl[1,3,2]dioxaborolane (0.75 mL), potassium phosphate monohydrate (2.3 g) and N,N-dimethylformamide (10 mL) was purged with argon for 20 minutes, and then treated with [1,1'-bis(diphenylphosphino)ferrocene]dichloropalladium (II) (0.080 g). The resulting mixture was heated at 90° C. for 12 hours, cooled to room temperature and filtered through Celite. The filtrate was concentrated under reduced pressure, diluted with saturated aqueous ammonium chloride solution (50 mL) and extracted with ethyl acetate (3×20 mL). The combined extracts were washed with saturated aqueous sodium chloride solution (50 mL), dried over magnesium sulfate and concentrated under reduced pressure. Purification of the residue by column chromatography on silica gel, eluting with a mixture of cyclohexane and ethyl acetate (1:0 to 1:1 by volume) gave title compound as a white solid (0.26 g).

MS: ESI (+ve) (Method B): 390 (M+H)$^+$, Retention time 3.9 min.

Preparation 44c 8-chloro-2-isopropyl-4-methyl-3-(4-pyrazol-1-ylbenzyl)quinolin-5-ol A mixture of 8-chloro-2-isopropenyl-4-methyl-3-(4-pyrazol-1-ylbenzyl)quinolin-5-ol (0.26 g), ethyl acetate (10 mL), methanol (5.0 mL) and palladium hydroxide (0.05 g) was stirred at room temperature for 27 hours under an atmosphere of hydrogen. The mixture was filtered through Celite and the filtrated concentrated under reduced pressure. Purification of the residue by column chromatography on silica gel, eluting with a mixture of cyclohexane and ethyl acetate (1:0 to 0:1 by volume) gave title compound as a yellow oil (0.21 g), $^1$H NMR (CDCl$_3$): δ 1.32 (d, J=6.6 Hz, 6H), 2.77 (s, 3H), 4.32 (s, 2H), 6.47 (m, 1H), 6.66 (d, J=8.2 Hz, 1H), 7.09 (d, J=8.7 Hz, 2H), 7.53 (m, 3H), 7.74 (m, 1H), 7.88 (dd, J=0.6, 2.5 Hz, 1H).

Preparation 44d

[8-chloro-2-isopropyl-4-methyl-3-(4-pyrazol-1-yl-benzyl)quinolin-5-yloxy]acetic acid methyl ester A mixture of 8-chloro-2-isopropyl-4-methyl-3-(4-pyrazol-1-ylbenzyl)quinolin-5-ol (0.10 g), acetone (3.0 mL), potassium carbonate (0.035 g) and bromoacetic acid methyl ester (0.025 mL) was stirred at room temperature for 20 hours. The mixture was concentrated under reduced pressure and the residue partitioned between ethyl acetate and water. The organic phase was dried over magnesium sulfate and concentrated under reduced pressure. Purification of the residue by column chromatography on silica gel, eluting with a mixture of cyclohexane and ethyl acetate (10:0 to 8:2 by volume) gave title compound as colourless oil (0.087 g).

MS: ESI (+ve) (Method B): 464 (M+H)$^+$, Retention time 4.63 min.

Preparation 44e

[8-chloro-2-isopropyl-4-methyl-3-(4-pyrazol-1-yl-benzyl)quinolin-5-yloxy]acetic acid A solution of [8-chloro-2-isopropyl-4-methyl-3-(4-pyrazol-1-ylbenzyl)quinolin-5-yloxy]acetic acid methyl ester (0.087 g) in tetrahydrofuran (3.0 mL) and 1.0M aqueous lithium hydroxide solution (0.5 mL) was stirred at room temperature for three hours. The mixture was concentrated under reduced pressure and the pH adjusted to 4 by the addition of 0.1M aqueous hydrochloric acid (3 mL). The mixture was extracted with ethyl acetate and the combined extracts washed with saturated aqueous sodium chloride solution and dried over magnesium sulfate. The solvent was removed under reduced pressure and the residue purified by column chromatography on silica gel, eluting with a mixture of cyclohexane, ethyl acetate and formic acid (1:0:0.001 to 0:1:0.001 by volume) to afford title compound as pale yellow solid (0.06 g).

$^1$H NMR (CDCl$_3$): δ 1.30 (d, J=6.6 Hz, 6H), 2.80 (s, 3H), 3.31 (m, 1H), 4.31 (s, 2H), 4.74 (s, 2H), 6.41 (t, J=2.1 Hz, 1H), 6.62 (d, J=8.5 Hz, 1H), 7.04 (d, J=8.5 Hz, 2H), 7.52 (d, J=8.5 Hz, 2H), 7.59 (d, J=8.5 Hz, 1H), 7.69 (d, J=1.4 Hz, 1H), 7.83 (d, J=2.4 Hz, 1H).

MS: ESI (+ve) (Method A): 450 (M+H)$^+$, Retention time 13.6 min.

Example 45

[2-cyclopropyl-8-fluoro-4-methyl-3-(4-pyrazol-1-ylbenzyl)quinolin-5-yloxy]acetic acid

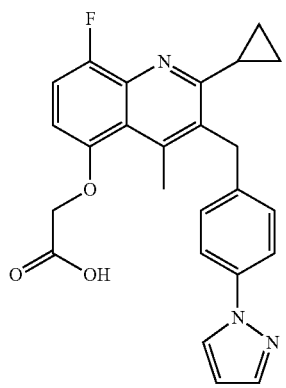 [SMILES: Cc1c(Cc2ccc(-n3cccn3)cc2)c(C2CC2)nc2c(F)ccc(OCC(=O)O)c12]

Preparation 45a 2-cyclopropyl-8-fluoro-4-methyl-3-(4-pyrazol-1-ylbenzyl)quinolin-5-ol A mixture of 2-chloro-8-fluoro-4-methyl-3-(4-pyrazol-1-ylbenzyl)quinolin-5-ol (0.26 g), cyclopropylboronic acid (0.12 g), caesium carbonate (0.92 g), dioxane (5.7 mL) and water (1.4 mL) was purged with argon, and then treated with [1,1'-bis(diphenylphosphino)ferrocene]dichloropalladium (II) (0.058 g). The mixture was heated at 90° C. for 3 hours, cooled to room temperature, neutralised with saturated aqueous ammonium chloride solution and extracted with ethyl acetate (3×20 mL). The combined extracts were washed with saturated aqueous sodium chloride solution (5.0 mL), dried over magnesium sulfate and concentrated under reduced pressure. Purification of the residue by column chromatography on silica gel, eluting with a mixture of cyclohexane and ethyl acetate (1:0 to 3:2 by volume) gave title compound as a yellow oil (0.061 g).

$^1$H NMR (DMSO-d6): δ 0.89 (m, 2H), 1.08 (m, 2H), 2.26 (m, 1H), 2.83 (s, 3H), 4.45 (s, 2H), 6.51 (dd, J=1.8, 2.5 Hz, 1H), 6.73 (dd, J=4.6, 8.6 Hz, 1H), 7.20 (m, 2H), 7.23 (d, J=8.6 Hz, 1H), 7.70 (dd, J=0.5, 1.8 Hz, 1H), 7.74 (m, 2H), 8.42 (dd, J=0.5, 2.5 Hz, 1H), 10.1 (br s, 1H).

MS: ESI (+ve) (Method B): 374 (M+H)$^+$, Retention time 3.7 min.

Preparation 45b

[2-cyclopropyl-8-fluoro-4-methyl-3-(4-pyrazol-1-ylbenzyl)quinolin-5-yloxy]acetic acid methyl ester A mixture of 2-cyclopropyl-8-fluoro-4-methyl-3-(4-pyrazol-1-ylbenzyl)quinolin-5-ol (0.040 g), potassium carbonate (0.044 g) and N,N-dimethylformamide (0.21 mL) was treated with methyl bromoacetate (0.011 mL), and the resulting mixture was stirred at room temperature for 1 hour. The mixture was diluted with water (30 mL), extracted with ethyl acetate (3×10 mL), and the combined extracts were dried over magnesium sulfate. The solvent was removed under reduced pressure and the residue purified by column chromatography on silica gel, eluting with a mixture of cyclohexane and ethyl acetate (1:0 to 3:2 by volume) to afford the title compound as a yellow oil (0.034 g).

MS: ESI (+ve) (Method B): 446 (M+H)$^+$, Retention time 4.2 min.

Preparation 45c

[2-cyclopropyl-8-fluoro-4-methyl-3-(4-pyrazol-1-ylbenzyl)quinolin-5-yloxy]acetic acid A solution of [2-cyclopropyl-8-fluoro-4-methyl-3-(4-pyrazol-1-ylbenzyl)quinolin-5-yloxy]acetic acid methyl ester (0.034 g) in tetrahydrofuran (0.19 mL) and water (0.19 mL) was treated with lithium hydroxide (0.037 g), and the resulting mixture was stirred at room temperature for 2 hours. The mixture was diluted with water, cooled to 0° C. and acidified by the addition of 1.0 M aqueous hydrochloric acid. The resulting precipitate was collected by filtration and dried to afford title compound as a pale pink solid (0.022 g).

$^1$H NMR (DMSO-d6): δ 0.87 (m, 2H), 1.05 (m, 2H), 2.25 (m, 1H), 2.82 (s, 3H), 4.45 (s, 2H), 4.72 (s, 2H), 6.46 (dd, J=1.8, 2.6 Hz, 1H), 6.77 (dd, J=4.2, 8.8 Hz, 1H), 716 (m, 2H), 7.29 (dd, J=8.8, 10.1 Hz, 1H), 7.66 (d, J=1.7 Hz, 1H), 7.70 (m, 2H),

MS: ESI (+ve) (Method A): 432 (M+H)$^+$, Retention time 11.5 min.

MS: ESI (+ve) (Method B): 432 (M+H)$^+$, Retention time 3.8 min.

Example 46

[8-chloro-2-isopropyl-4-methyl-3-(4-pyrazol-1-yl-benzyl)quinolin-5-yl]acetic acid

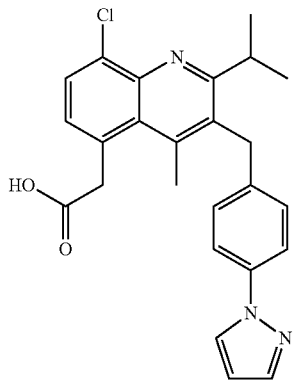 [SMILES: Cc1c(Cc2ccc(-n3cccn3)cc2)c(C(C)C)nc2c(Cl)ccc(CC(=O)O)c12]

Preparation 46a trifluoromethanesulfonic acid 8-chloro-2-isopropyl-4-methyl-3-(4-pyrazol-1-ylbenzyl)quinolin-5-yl ester A mixture of 8-chloro-2-isopropyl-4-methyl-3-(4-pyrazol-1-ylbenzyl)quinolin-5-ol (0.1 g), dichloromethane (3.0 mL) and triethylamine (0.11 mL) at 0° C. was treated with trifluoromethanesulfonic anhydride (0.064 mL), and the resulting mixture was stirred at 0° C. for 15 minutes and then at room temperature for 1 hour. The mixture was cooled to 0° C., diluted with saturated aqueous sodium hydrogen carbonate solution (5.0 mL) and extracted with dichloromethane. The combined extracts were washed with saturated aqueous sodium chloride solution, dried over magnesium sulfate and concentrated under reduced pressure to afford title compound as yellow oil (0.075 g).

MS: ESI (+ve) (Method B): 524 (M+H)$^+$, Retention time 4.9 min.

Preparation 46b

[8-chloro-2-isopropyl-4-methyl-3-(4-pyrazol-1-yl-benzyl)quinolin-5-yl]acetic acid methyl ester A mixture of trifluoromethanesulfonic acid 8-chloro-2-isopropyl-4-methyl-3-(4-pyrazol-1-ylbenzyl)quinolin-5-yl ester (0.075 g), tert-butyl-(1-methoxyvinyloxy)dimethylsilane (0.063 mL), lithium acetate (0.029 g) and tetrahydrofuran (2.0 mL) was purged with argon for 30 minutes, and then treated with tetrakis(triphenylphosphine)palladium (0) (0.017 g). The mixture was stirred at 70° C. for four days, cooled to room temperature and filtered through Celite. The filtrate was concentrated under reduced pressure and the residue purified by column chromatography on silica gel, eluting with a mixture of cyclohexane and ethyl acetate (10:0 to 2:8 by volume) to give title compound as pale yellow oil (0.042 g).

MS: ESI (+ve) (Method B): 448 (M+H)$^+$, Retention time 4.5 min.

Preparation 46c

[8-chloro-2-isopropyl-4-methyl-3-(4-pyrazol-1-yl-benzyl)quinolin-5-yl]acetic acid A solution of [8-chloro-2-isopropyl-4-methyl-3-(4-pyrazol-1-ylbenzyl)quinolin-5-yl]acetic acid methyl ester (0.04 g) in tetrahydrofuran (3.0 mL) was treated with 1.0 M aqueous lithium hydroxide solution (0.3 mL), and the resulting mixture was stirred at room temperature for six hours. The mixture was concentrated under reduced pressure and the pH adjusted to 4 by the addition of 0.1M aqueous hydrochloric acid (3.0 mL). The mixture was extracted with ethyl acetate and the combined extracts washed with saturated aqueous sodium chloride solution and dried over magnesium sulfate. The solvent was removed under reduced pressure and the residue purified by preparative reverse-phase HPLC, eluting with a mixture of acetonitrile and water (5:95 to 98:2 by volume) to afford title compound as white solid (0.024 g).

$^1$H NMR (DMSO-d6): δ 1.24 (d, J=6.4 Hz, 6H), 2.66 (s, 3H), 3.36 (m, 1H), 4.21 (s, 2H), 4.36 (s, 2H), (151 (m, 1H), 7.12 (d, J=8.6 Hz, 2H), 7.35 (d, J=7.9 Hz, 1H), 7.70 (d, J=1.7 Hz, 1H), 7.73 (m, 2H), 7.78 (d, J=7.9 Hz, 1H), 8.41 (d, J=2.4 Hz, 1H).

MS: ESI (+ve) (Method A): 434 (M+H)$^+$, Retention time 12.7 min.

Example 47

(S)-2-[2-cyclopropyl-8-fluoro-4-methyl-3-(4-pyrazol-1-ylbenzyl)quinolin-5-yloxy]propionic acid

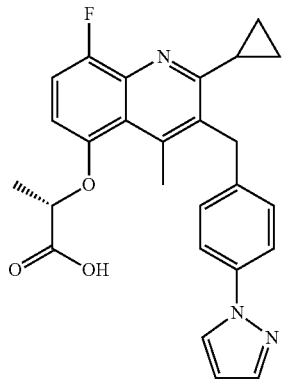 [SMILES: Cc1c(Cc2ccc(-n3cccn3)cc2)c(C2CC2)nc2c(F)ccc(O[C@@H](C)C(=O)O)c12]

Preparation 48a (S)-2-[2-cyclopropyl-8-fluoro-4-methyl-3-(4-pyrazol-1-ylbenzyl)quinolin-5-yloxy]propionic acid methyl ester A mixture of 2-cyclopropyl-8-fluoro-4-methyl-3-(4-pyrazol-1-ylbenzyl)quinolin-5-ol (0.064 g), (N-dimethylformamide (0.86 mL), potassium carbonate (0.071 g) and (R)-2-chloropropionic acid methyl ester (0.032 g) was stirred at 40° C. for 3 days. The mixture was cooled to 0° C., diluted with water (40 mL) and extracted with ethyl acetate (3×10 mL). The combined extracts were washed saturated aqueous sodium chloride solution, dried over magnesium sulfate and concentrated under reduced pressure. Purification of the residue by column chromatography on silica gel, eluting with a mixture of ethyl acetate and cyclohexane (0:1 to 4:6 by volume) gave title compound as a colourless oil (0.033 g).

MS: ESI (+ve) (Method 13): 460 (M+H)$^+$, Retention time 4.4 min.

Preparation 48b (S)-2-[2-cyclopropyl-8-fluoro-4-methyl-3-(4-pyrazol-1-ylbenzyl)quinolin-5-yloxy]propionic acid A solution of (S)-2-[2-cyclopropyl-8-fluoro-4-methyl-3-(4-pyrazol-1-ylbenzyl)quinolin-5-yloxy]propionic acid methyl ester (0.033 g) in tetrahydrofuran (0.18 mL) and water (0.18 mL) was treated with lithium hydroxide (0.018 g), and the resulting mixture was stirred at room temperature for 4 hours. The mixture was cooled to 0° C., diluted with water (10 mL) and acidified by the addition of 1.0M aqueous hydrochloric acid. The mixture was extracted with ethyl acetate and the combined extracts were dried over magnesium sulfate and concentrated under reduced pressure to afford title compound as a yellow solid (0.023 g).

$^1$H NMR (DMSO-d6): δ 0.88 (m, 2H), 1.05 (m, 2H), 1.54 (d, J=6.9 Hz, 3H), 2.26 (m, 1H), 2.80 (s, 3H), 4.45 (s, 2H), 4.93 (q, J=6.7 Hz, 1H), 6.47 (dd, J=1.8, 2.6 Hz, 1H), 6.67 (dd, J=4.1, 8.8 Hz, 1H), 7.17 (m, 2H), 7.28 (dd, J=8.8, 10.1 Hz, 1H), 7.66 (d, J=1.6 Hz, 1H), 7.71 (m, 2H), 8.37 (d, J=2.6 Hz, 1H), 13.2 (br s, 1H).

MS: ESI (+ve) (Method A): 446 (M+H)$^+$, Retention time 12.0 min.

Biological Methods

Compounds of the invention of formula (I) were tested using the following biological test methods to determine their ability to displace PGD$_2$ from the CRTH2 receptor and for their ability to antagonise the functional effects of PGD$_2$ at the CRTH2 receptor in a whole cell system.

Radioligand Binding Assay

The receptor binding assay is performed in a final volume of 200 μL binding buffer [10 mM BES (pH 7.4), 1 mM EDTA, 10 mM manganese chloride, 0.01% BSA] and 1 nM [$^3$H]-PGD$_2$ (Amersham Biosciences UK Ltd). Ligands are added in assay buffer containing a constant amount of DMSO (1% by volume). Total binding is determined using 1% by volume of DMSO in assay buffer and non-specific binding is determined using 10 μM of unlabeled PGD$_2$ (Sigma). Human embryonic kidney (HEK) cell membranes (3.5 μg) expressing the CRTH2 receptor are incubated with 1.5 mg wheatgerm agglutinin SPA beads and 1 nM [$^3$H]-PGD$_2$ (Amersham Biosciences UK Ltd) and the mixture incubated for 3 hours at room temperature. Bound [$^3$H]-PGD$_2$ is detected using a Microbeta TRILUX liquid scintillation counter (Perkin Elmer). Compound IC$_{50}$ value is determined using a 6-point dose response curve in duplicate with a semi-log compound dilution series. IC$_{50}$ calculations are performed using Excel and XLfit (Microsoft), and this value is used to determine a Ki value for the test compound using the Cheng-Prusoff equation.

GTPγS Assay

The GTPγS Assay is performed in a final volume of 200 mL assay buffer (20 mM HEPES pH 7.4, 10 mM MgCl$_2$, 100 mM NaCl, 10 μg/mL saponin). DMSO concentrations are kept constant at 1% by volume. Human embryonic kidney (HEK) cell membranes (3.5 μg) expressing the CRTH2 receptor are incubated with the compounds for 15 min at 30° C. prior to addition of PGD$_2$ (30 nM final concentration) and GTP (10 μM final concentration). The assay solutions are then incubated for 30 minutes at 30° C., followed by addition of [$^{35}$S]-GTPγS (0.1 nM final concentration). The assay plate is than shaken and incubated for 5 minutes at 30° C. Finally, SPA beads (Amersham Biosciences, UK) are added to a final concentration of 1.5 mg/well and the plate shaken and incubated for 30 minute at 30° C. The sealed plate is centrifuged at 1000 g for 10 mins at 30° C. and the bound [$^{35}$S]-GTPγS is detected on Microbeta scintillation counter (Perkin Elmer). Compound IC$_{50}$ value is determined using a 6-point dose response curve in duplicate with a semi-log compound dilution series. IC$_{50}$ calculations are performed using Excel and XLfit (Microsoft), and this value is used to determine a Ki value for the test compound using the Cheng-Prusoff equation.

Biological Results:

Compounds of the Examples above were tested in the CRTH2 radioligand binding and GTPγS functional assays described above; the compounds all have IC$_{50}$ values of less than 1 μM in both assays. For example, the compound of Example 1 had an IC$_{50}$ value of 5.4 nM in the CRTH2 radioligand binding assay, and the compound of Example 2 had an IC$_{50}$ value of 6.3 nM in that assay.

We claim:

1. A method for treating a condition responsive to modulation of CRTH2 receptor activity, comprising administering, to a patient in need of such treatment, an effective amount of [2-cyclopropyl-8-fluoro-4-methyl-3-(4-pyrazol-1-ylbenzyl) quinolin-5-yloxyl]acetic acid, or a pharmaceutically acceptable salt thereof, wherein the condition is selected from allergic airway diseases, chronic obstructive pulmonary disease, ulcerative colitis, Crohn's disease, irritable bowel disease, and atopic and non-atopic dermatitis.

2. The method as claimed in claim 1, wherein the allergic airway disease is asthma and/or rhinitis.

3. The method as claimed in claim 1, wherein the condition is selected from atopic and non-atopic dermatitis, Crohn's disease, ulcerative colitis, and irritable bowel disease.

* * * * *